US010947548B2

(12) United States Patent
Deng et al.

(10) Patent No.: US 10,947,548 B2
(45) Date of Patent: Mar. 16, 2021

(54) **PRODUCTION OF ORGANIC ACIDS FROM *ASPERGILLUS* CIS-ACONITIC ACID DECARBOXYLASE (CADA) DELETION STRAINS**

(71) Applicant: Battelle Memorial Institute, Richland, WA (US)

(72) Inventors: Shuang Deng, Richland, WA (US); Ziyu Dai, Richland, WA (US); Jon K. Magnuson, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 16/393,149

(22) Filed: Apr. 24, 2019

(65) Prior Publication Data

US 2019/0323020 A1 Oct. 24, 2019

Related U.S. Application Data

(60) Provisional application No. 62/661,804, filed on Apr. 24, 2018.

(51) Int. Cl.

| | |
|---|---|
| ***C12N 1/15*** | (2006.01) |
| ***C12N 9/88*** | (2006.01) |
| ***C12N 9/10*** | (2006.01) |
| ***C12N 9/04*** | (2006.01) |
| ***C12P 7/42*** | (2006.01) |
| ***C12P 7/52*** | (2006.01) |
| ***C12N 15/80*** | (2006.01) |
| ***C12P 7/48*** | (2006.01) |

(52) U.S. Cl.

CPC .......... *C12N 15/80* (2013.01); *C12N 9/0006* (2013.01); *C12N 9/1096* (2013.01); *C12N 9/88* (2013.01); *C12P 7/42* (2013.01); *C12P 7/48* (2013.01); *C12Y 101/01059* (2013.01); *C12Y 206/01018* (2013.01); *C12Y 401/01011* (2013.01)

(58) Field of Classification Search

None

See application file for complete search history.

(56) References Cited

U.S. PATENT DOCUMENTS

| | | | | |
|---|---|---|---|---|
| 4,740,464 A * | 4/1988 | Holdom | .................... | C12P 7/48 435/135 |
| 2008/0199926 A1* | 8/2008 | Burgard | ................. | C12N 15/52 435/141 |
| 2015/0267228 A1* | 9/2015 | Borodina | ................ | C12N 9/88 435/146 |

FOREIGN PATENT DOCUMENTS

| | | |
|---|---|---|
| CN | 110527637 A * | 12/2019 |
| WO | WO 2018/213349 A1 | 11/2018 |

OTHER PUBLICATIONS

Samson et al., Studies in Mycology 78:141-173, 2014 (Year: 2014).*

Van der Straat et al., Microb. Cell Fac. 13:11, 2014, 9 pages (Year: 2014).*

Rodrigues et al., Fung. Genet. Biol. 138 (2020) 103367, 11 pages (Year: 2020).*

Deng et al., Appl. Microbiol. Biotechnol. 104:3981-3992, 2020 (Year: 2020).*

UniProt Database Accession No. B3IUN8, Oct. 2017, 2 pages (Year: 2017).*

GenBank Database Accession No. AB326105, Aug. 2008, 2 pages (Year: 2008).*

Nielsen, J., Appl. Microbiol. Biotechnol. 55:263-283, 2001 (Year: 2001).*

Steiger et al., Frontiers Microbiol. 4:23, 2013, 5 pages (Year: 2013).*

Samson et al., Studies in Mycology 69:39-55, 2011 (Year: 2011).*

Deng et al., "Deletion Analysis of the Itaconic Acid Production Gene Cluster Components in *Aspergillus pseudoterreus* ATCC32359," Poster presented at 40th Symposium on Biotechnology for Fuels and Chemicals, Apr. 29-May 2, 2018, Clearwater, Florida.

* cited by examiner

*Primary Examiner* — David Steadman

(74) *Attorney, Agent, or Firm* — Klarquist Sparkman, LLP

(57) ABSTRACT

This application provides recombinant *Aspergillus* fungi having an endogenous cis-aconitic acid decarboxylase (cadA) gene genetically inactivated, which allows aconitic acid production by the recombinant fungi. Such recombinant fungi can further include an exogenous nucleic acid molecule encoding aspartate decarboxylase (panD), an exogenous nucleic acid molecule encoding β-alanine-pyruvate aminotransferase (BAPAT), and an exogenous nucleic acid molecule encoding 3-hydroxypropionate dehydrogenase (HPDH). Kits including these fungi, and methods of using these fungi to produce aconitic acid and 3-hydroxypropionic acid (3-HP) are also provided.

15 Claims, 10 Drawing Sheets

Specification includes a Sequence Listing.

aconitic acid (g/L)
12.00
10.00
8.00
6.00
4.00
2.00
0.00
cis-aconitic acid
trans-aconitic acid
day2
day3
day4
day5
day6
day7
day10

PRODUCTION OF ORGANIC ACIDS FROM *ASPERGILLUS* CIS-ACONITIC ACID DECARBOXYLASE (CADA) DELETION STRAINS

CROSS REFERENCE TO RELATED APPLICATION

This application claims priority to U.S. Provisional Application No. 62/661,804 filed Apr. 24, 2018, herein incorporated by reference in its entirety.

ACKNOWLEDGMENT OF GOVERNMENT SUPPORT

This disclosure was made with Government support under Contract DE-AC05-76RL0 1830 awarded by the U.S. Department of Energy. The Government has certain rights in the invention.

FIELD

Recombinant *Aspergillus* genetically inactivated for an endogenous cis-aconitic acid decarboxylase (cadA) gene are provided, as are methods of using such recombinant fungi to produce aconitic acid and 3-hydroxypropionic acid (3-HP).

BACKGROUND

Itaconic acid (IA) is utilized as a monomer or co-monomer to form polymers that are used as raw material for plastics, resins, synthetic fibers and elastomers, detergents and cleaners. *Aspergillus terreus* Thom, produces an appreciable amount of itaconic acid when grown in a glucose medium. Cell-free extracts of *Aspergillus terreus* contain cis-aconitic decarboxylase (cadA), which can decarboxylate cis-aconitic acid into equal moles of itaconic acid and carbon dioxide.

The itaconic acid gene cluster (IA cluster) includes four genes, including cis-aconitic acid decarboxylase (cadA), a predicted transcription factor (tf), mitochondrial organic acid transporter (mttA), and MFS (Major Facilitator Superfamily) type transporter (mfsA) located in plasma membranes. Expression of one or more genes of the IA gene cluster in hetereologous hosts, including *E. coli, A. niger*, and *S. cerevisiae*, can result in the production of itaconic acid in non itaconic acid host microorganisms.

Characterization and regulation of genes in the IA biosynthesis cluster through gene deletion had not been previously investigated. The inventors used protoplast transformation to delete each gene in the IA cluster in *Aspergillus terreus/Aspergillus pseudoterreus*, which allowed for the effect on cell growth and IA production to be investigated.

SUMMARY

The role of cis-aconitic acid decarboxylase (cadA), a predicted transcription factor (tf), mitochondrial organic acid transporter (mttA), and MFS (Major Facilitator Superfamily) type transporter (mfsA) in IA biosynthesis in *A. pseudoterreus* ATCC 32359 is shown herein. Expressed Sequence Tag (EST) analysis showed a similar expression pattern among those four genes distinct from neighboring genes. Systematic gene deletion analysis demonstrated that tf, cadA, mttA and mfsA genes in the cluster are essential for IA production. Interestingly, significant amounts of aconitic acid production was detected in the cadA deletion strain but not in the other deletion strains.

Based on these observations, a novel recombinant ΔcadA *Aspergillus* strain is provided, which can be used for aconitic acid and other organic acid production. Provided herein are isolated recombinant fungi (such as *Aspergillus* filamentous fungi) having a gene inactivation (also referred to herein as a gene deletion or functional deletion) of a cis-aconitic acid decarboxylase (cadA) gene (referred to herein as ΔcadA strains). In some examples, the *Aspergillus* fungi is *Aspergillus terreus* or *Aspergillus pseudoterreus*, or particular strains thereof (for example *A. pseudoterreus* ATCC32359 and *A. terreus* NRRL 1960). In particular examples, a ΔcadA strain exhibits one or more of the following characteristics: produces at least 2-fold, at least 3-fold, at least 3.5 fold, at least 5-fold, at least 8-fold, or at least 10-fold more total aconitic acid than a wild-type *Aspergillus terreus* or *Aspergillus pseudoterreus* (for example at day 3, 4, 5, 6, 7, 8, 9 or 10 of production); produces at least 2-fold more cis-aconitic acid at day 5, 6, 7, 8, 9, or 10 of culturing in Riscaldati medium than a wild-type *Aspergillus terreus* or *Aspergillus pseudoterreus*; produces at least 2-fold, at least 3-fold, at least 5-fold, or at least 10-fold more trans-aconitic acid at day 10 of culturing in Riscaldati medium than a wild-type *Aspergillus terreus* or *Aspergillus pseudoterreus*; or combinations thereof. In some examples, such increases are relative to *Aspergillus terreus* strain ATCC 32359 grown under the same conditions.

In particular examples, a ΔcadA fungi further includes an exogenous nucleic acid molecule encoding aspartate 1-decarboxylase (panD), an exogenous nucleic acid molecule encoding β-alanine-pyruvate aminotransferase (BAPAT), and an exogenous nucleic acid molecule encoding 3-hydroxypropionate dehydrogenase (HPDH). The ΔcadA fungi expressing panD, BAPAT, and HPDH can be used to produce 3-HP. Such exogenous nucleic acid molecules can be part of one or more exogenous nucleic acid molecules, such as 1, 2 or 3 exogenous nucleic acid molecules. In one example, the exogenous nucleic acid molecule encoding panD has at least 80%, at least 90%, at least 95%, at least 98%, or 100% sequence identity to SEQ ID NO: 53 or 65 and/or encodes a panD protein having at least 80%, at least 90%, at least 95%, at least 98%, or 100% sequence identity to SEQ ID NO: 54. In one example, the exogenous nucleic acid molecule encoding BAPAT has at least 80%, at least 90%, at least 95%, at least 98%, or 100% sequence identity to SEQ ID NO: 55, and/or encodes a BAPAT protein having at least 80%, at least 90%, at least 95%, at least 98%, or 100% sequence identity to SEQ ID NO: 56. In one example, the exogenous nucleic acid molecule encoding HPDH has at least 80%, at least 90%, at least 95%, at least 98%, or 100% sequence identity to SEQ ID NO: 57, and/or encodes a HPDH protein having at least 80%, at least 90%, at least 95%, at least 98%, or 100% sequence identity to SEQ ID NO: 58. Such panD, BAPAT, and HPDH nucleic acid molecules can be part of a vector. In addition, expression of the panD, BAPAT, and HPDH can be driven by one or more promoters.

The endogenous cadA gene is genetically inactivated in some examples by a deletion mutation (complete or partial) or by insertional mutation (e.g., by insertion of an antibiotic resistance gene, such as hygromycin). In some examples, prior to its genetic inactivation, the cadA gene encodes a protein having at least 80%, at least 90%, at least 95%, at least 98%, or 100% sequence identity to SEQ ID NO: 50 or 52. In some examples, prior to its genetic inactivation, the cadA gene (or a cadA coding sequence) comprises at least 80%, at least 90%, at least 95%, at least 98%, or 100% sequence identity to SEQ ID NO: 49, 51, 59 or 92.

Also provided herein are compositions (such as a culture media or fermentation broth) and kits that include a *Aspergillus* ΔcadA strain. Also provided herein are compositions (such as a culture media or fermentation broth) and kits that include an *Aspergillus* ΔcadA strain that also express panD, BAPAT, and HPDH, in some examples such genes are exogenous to the fungi. In some examples, the composition or kit includes Riscaldati medium (such as modified Riscaldati medium with 20× trace elements).

Also provided herein are methods of making aconitic acid (such as cis-aconitic acid, trans-aconitic acid, or both) using the disclosed *Aspergillus* ΔcadA strains. For example, such a method can include culturing an isolated ΔcadA *Aspergillus* under conditions that permit the fungus to make aconitic acid, thereby producing aconitic acid. For example, the ΔcadA fungus can be cultured in Riscaldati medium. In some examples, the method further includes isolating the aconitic acid produced, for example isolating it from the culture media or from the fungus.

Also provided herein are methods of making 3-hydroxypropionic acid (3-HP using the disclosed *Aspergillus* ΔcadA strains that also expresses panD, BAPAT, and HPDH (which can be exogenous). For example, such a method can include culturing an isolated ΔcadA *Aspergillus* that also expresses panD, BAPAT, and HPDH under conditions that permit the fungus to make 3-HP, thereby producing 3-HP. For example, the ΔcadA fungus that also expresses panD, BAPAT, and HPDH can be cultured in Riscaldati medium (such as one including 20× trace elements). In some examples, the method further includes isolating the 3-HP produced, for example isolating it from the culture media or from the fungus.

The foregoing and other objects and features of the disclosure will become more apparent from the following detailed description, which proceeds with reference to the accompanying figures.

SEQUENCE LISTING

Figure 1:
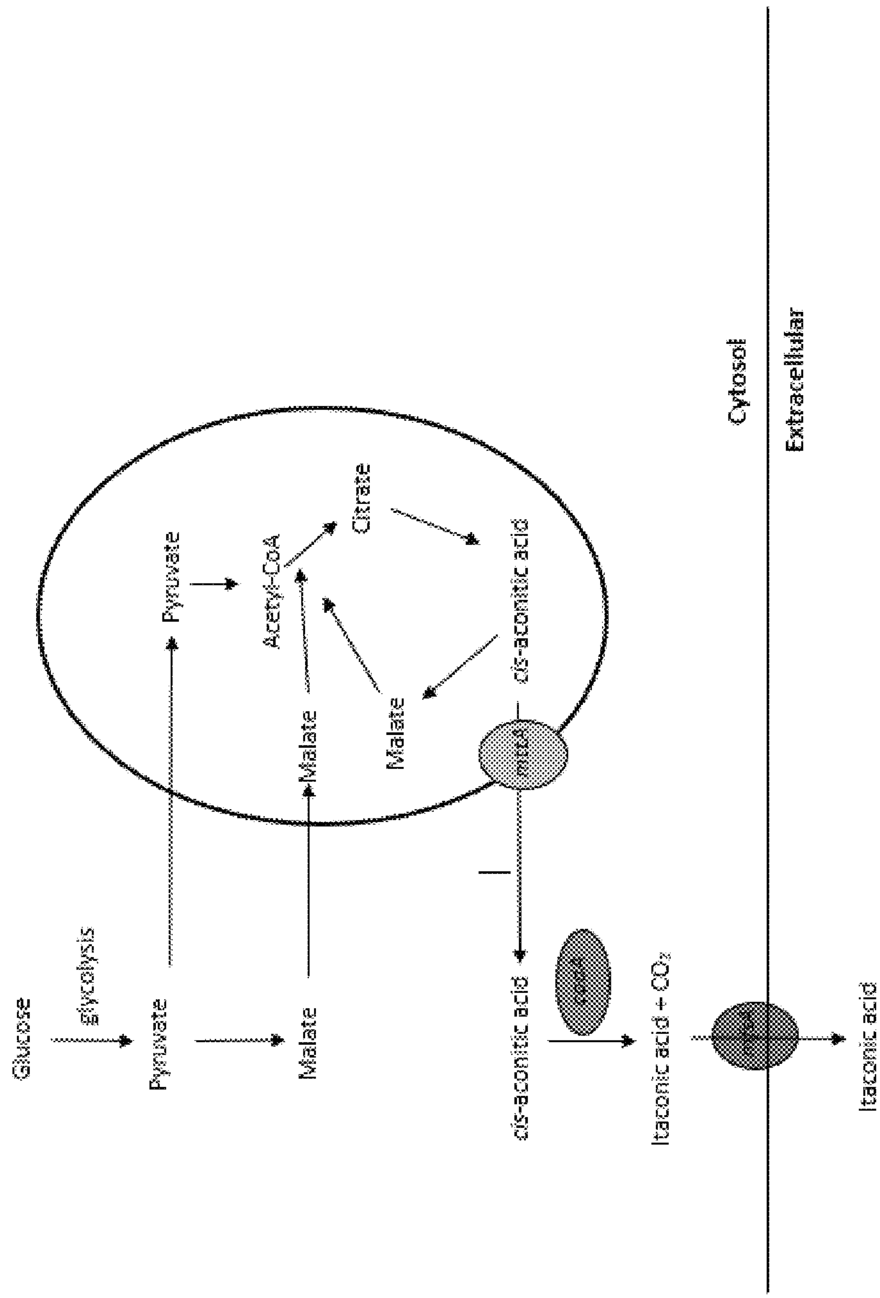
FIG. 1. Hypothesized itaconic acid (IA) production and transport pathway in *Aspergillus pseudoterreus* and *Aspergillus terreus*. Glucose is utilized by *A. terreus* and *A. pseudoterreus* to form pyruvate and is subsequently converted to citric acid for tricarboxylic acid (TCA) cycle in the mitochondria. Citric acid is dehydrated to cis-aconitic acid, which is then transported from mitochondria to cytosol through transporter mttA. In the cytosol, cis-aconitic acid is decarboxylated into itaconic acid and $CO_2$ by cis-aconitic decarboxylase. Finally, itaconic acid secreted outside of cell through transporters, for example mfsA.

The nucleic acid sequences listed in the accompanying sequence listing are shown using standard abbreviations for nucleotide bases and amino acids, as defined in 37 C.F.R. 1.822. Only one strand of each nucleic acid sequence is shown, but the complementary strand is understood as included by any reference to the displayed strand. The sequence listing submitted herewith, generated on Apr. 24, 2019, 80 kb, is herein incorporated by reference. In the accompanying sequence listing:

SEQ ID NOS: 1-8 are primers used to delete the tf gene in *A. pseudoterreus.*

SEQ ID NOS: 9-16 are primers used to delete the mttA gene in *A. pseudoterreus.*

SEQ ID NOS: 17-24 are primers used to delete the cadA gene in *A. pseudoterreus.*

SEQ ID NOS: 25-32 are primers used to delete the mfsA gene in *A. pseudoterreus.*

SEQ ID NOS: 33-40 are primers used to delete the p450 gene in *A. pseudoterreus.*

SEQ ID NOS: 41-42 are primers used to amplify mttA in *A. pseudoterreus.*

SEQ ID NOS: 43-44 are primers used to amplify cadA in *A. pseudoterreus.*

SEQ ID NOS: 45-46 are primers used to amplify mfsA in *A. pseudoterreus.*

SEQ ID NOS: 47-48 are primers used to amplify benA in *A. pseudoterreus.*

SEQ ID NOS: 49 and 50 are exemplary cadA nucleic acid and protein sequences, respectively, from *A. terreus* (GenBank Accession Nos. AB326105.1 and BAG49047.1).

SEQ ID NOS: 51 and 52 are exemplary cadA nucleic acid and protein sequences, respectively, from *A. vadensis* CBS 113365 (GenBank Accession Nos. XM_025706777.1 and XP_025563141.1).

SEQ ID NOS: 53 and 54 are exemplary aspartate 1-decarboxylase (panD) nucleic acid and protein sequences, respectively, from *Tribolium castaneum* (GenBank Accession Nos. NM_001102585.1 and NP_001096055.1). Coding sequence nt 41-1663.

SEQ ID NOS: 55 and 56 are exemplary β-alanine-pyruvate aminotransferase (BAPAT) nucleic acid and protein sequences, respectively, from *Bacillus cereus* AH1272 (GenBank Accession Nos. ACMS01000158.1 (complement (10606 . . . 11961)) and EEL86940.1).

SEQ ID NOS: 57 and 58 are exemplary 3-hydroxypropionate dehydrogenase (HPDH) nucleic acid and protein sequences (GenBank Accession No. WP_000636571), respectively.

SEQ ID NO: 59 is an *A. pseudoterreus* 5'-cadA nucleic acid sequence.

SEQ ID NOS: 60-61 are primers used to isolate an *A. pseudoterreus* 5'-cadA gene.

SEQ ID NO: 62 is an *A. niger* gpdA promoter nucleic acid sequence.

SEQ ID NOS: 63-64 are primers used to isolate an *A. niger* gpdA promoter.

SEQ ID NO: 65 is panD cDNA of *Tribolium castaneum* with codon optimization for *A. pseudoterreus.*

SEQ ID NOS: 66-67 are primers used to isolate panD cDNA of *Tribolium castaneum* with codon optimization for *A. pseudoterreus.*

SEQ ID NO: 68 is a bidirectional terminator from *A. niger* elf3/multifunctional chaperone.

SEQ ID NOS: 69-70 are primers used to isolate bidirectional terminator from *A. niger* elf3/multifunctional chaperone.

SEQ ID NO: 71 is codon optimized synthetic cDNA of β-alanine-pyruvate aminotransferase (BAPAT) of *Bacillus cereus.*

SEQ ID NOS: 72-73 are primers used to isolate a codon optimized synthetic cDNA of BAPAT of *Bacillus cereus.*

SEQ ID NO: 74 is an *A. niger* enol promoter.

SEQ ID NOS: 75-76 are primers used to isolate an *A. niger* enol promoter.

SEQ ID NO: 77 is an *A. nidulans* gpdA promoter.

SEQ ID NOS: 78-79 are primers used to isolate an *A. nidulans* gpdA promoter.

SEQ ID NO: 80 is the codon optimized synthetic cDNA of *E. coli* 3-hydroxypropionate dehydrogenase (HPDH).

SEQ ID NOS: 81-82 are primers used to isolate a codon optimized synthetic cDNA of *E. coli* HPDH.

SEQ ID NO: 83 is a trpC terminator of *A. nidulans.*

SEQ ID NOS: 84-85 are primers used to isolate the trpC terminator of *A. nidulans.*

SEQ ID NO: 86 is a trpC terminator of *A. nidulans.*

SEQ ID NOS: 87-88 are primers used to isolate a trpC terminator of *A. nidulans.*

SEQ ID NO: 89 is an *A. oryzae* ptrA selection marker gene.

SEQ ID NOS: 90-91 are primers used to isolate the *A. oryzae* ptrA selection marker gene.

SEQ ID NO: 92 is an *A. pseudoterreus* 3'-cadA gene.

SEQ ID NOS: 93-94 are primers used to isolate an *A. pseudoterreus* 3'-cadA gene fragment.

SEQ ID NO: 95 is a combination of Fragments 7 to 9 (SEQ ID NOS: 77, 80, and 83, respectively).

SEQ ID NO: 96 is a primer used to isolate Fragments 7 to 9 (in combination with SEQ ID NO: 88).

SEQ ID NO: 97 is a combination of Fragments 11 and 12 (SEQ ID NOS: 89 and 92, respectively).

SEQ ID NO: 98 is a primer used to isolate Fragments 11 to 12 (in combination with SEQ ID NO: 90).

DETAILED DESCRIPTION

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology,* published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, references and Genbank® Accession numbers (the sequence available on Apr. 24, 2019) mentioned herein are incorporated by reference in their entireties. The materials, methods, and examples are illustrative only and not intended to be limiting.

In order to facilitate review of the various embodiments of the disclosure, the following explanations of specific terms are provided:

3-hydroxypropionate dehydrogenase (HPDH): EC 1.1.1.59 An enzyme that catalyzes the chemical reaction: 3-hydroxypropanoate+$NAD^+$⇆3-oxopropanoate+NADH+$H^+$. The term HPDH includes any HPDH gene (such as a bacterial or fungal panD sequence), cDNA, mRNA, or protein, that is a HPDH that can covert 3-hydroxypropanoate and NAD into 3-oxopropanoate, NADH, and $H^+$ and vice versa. Expression or increased expression of HPDH, for example in an *Aspergillus* also expressing BAPAT and panD and having a genetically inactivated cadA gene (ΔcadA), results in a fungus that has an ability to produce more 3-HP than the parent strain (such as at least 20%, at least 30%, at least 40%, 50%, at least 60% at least 70%, at least 100%, at least 200%, at least 300%, or at least 400% more than a parent strain under the same growing conditions).

HPDH sequences are publicly available. For example, SEQ ID NO: 57 discloses an HPDH coding sequence and GenBank® Accession No: WP_000636571 discloses an HPDH protein sequence (SEQ ID NO: 58); GenBank® Accession Nos. FR729477.2 (nt 1005136 . . . 1005885) and CBY27203.1 disclose exemplary *Yersinia enterocolitica* subsp. *palearctica* Y11 HPDH nucleic acid and protein sequences, respectively; and GenBank® Accession Nos: CP004083.1 (complement (1399227 . . . 1399973) and AJQ99264.1 disclose exemplary *Enterobacteriaceae bacterium* bta3-1 HPDH nucleic acid and protein sequences, respectively. However, one skilled in the art will appreciate that in some examples, a HPDH sequence can include variant sequences (such as allelic variants and homologs) that retain HPDH activity and when expressed in an *Aspergillus* also expressing BAPAT and panD and with a genetically inactivated cadA gene (ΔcadA), results in a fungus that has an ability to produce more 3-HP than the parent strain (such as at least 20%, at least 30%, at least 40%, 50%, at least 60% at least 70%, at least 100%, at least 200%, at least 300%, or at least 400% more than a parent strain under the same growing conditions).

Aconitic acid: An organic acid with two isomers, cis- and trans-aconitic acid. The ΔcadA fungi provided herein can be used to produce cis- and trans-aconitic acid.

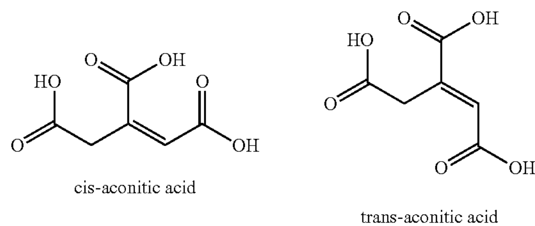 [SMILES: O=C(O)/C=C(/CC(=O)O)C(=O)O ; O=C(O)/C=C(\CC(=O)O)C(=O)O]

cis-aconitic acid trans-aconitic acid

Aspartate 1-decarboxylase (panD): EC 4.1.1.11. An enzyme that catalyzes the chemical reaction: L-aspartate⇆beta-alanine+$CO_2$. The term panD includes any panD gene (such as a bacterial or fungal panD sequence), cDNA, mRNA, or protein, that is a panD that can covert L-aspartate into beta-alanine+$CO_2$ and vice versa. Expression or increased expression of panD, for example in an *Aspergillus* also expressing BAPAT and HPDH and having a genetically inactivated cadA gene (ΔcadA), results in a fungus that has an ability to produce more 3-HP than the parent strain (such as at least 20%, at least 30%, at least 40%, 50%, at least 60% at least 70%, at least 100%, at least 200%, at least 300%, or at least 400% more than a parent strain under the same growing conditions)

panD sequences are publicly available. For example, GenBank® Accession Nos: NM_001102585.1 and NP_001096055.1 disclose *Tribolium castaneum* panD nucleic acid and protein sequences, respectively (SEQ ID NOS: 55 and 56); GenBank® Accession Nos. CP002745.1 (complement (4249351 . . . 4249824)) and AEK63458.1 disclose exemplary *Collimonas fungivorans* Ter331 panD nucleic acid and protein sequences, respectively; and GenBank® Accession Nos: CP029034.1 (nt 1201611 . . . 1201994) and AWE15802.1 disclose exemplary *Bacillus velezensis* panD nucleic acid and protein sequences, respectively. However, one skilled in the art will appreciate that in some examples, a panD sequence can include variant sequences (such as allelic variants and homologs) that retain panD activity and when expressed in an *Aspergillus* also expressing BAPAT and HPDH and with a genetically inactivated cadA gene (ΔcadA), results in a fungus that has an ability to produce more 3-HP than the parent strain (such as at least 20%, at least 30%, at least 40%, 50%, at least 60% at least 70%, at least 100%, at least 200%, at least 300%, or at least 400% more than a parent strain under the same growing conditions).

β-alanine-pyruvate aminotransferase (BAPAT): EC 2.6.1.18. An enzyme that can catalyze the reaction L-alanine+3-oxopropanoate⇆beta-alanine+pyruvate. The term BAPAT includes any BAPAT gene (such as a bacterial or fungal panD sequence), cDNA, mRNA, or protein, that is a BAPAT that can convert beta-alanine and pyuvate to L-alanine and 3-oxopropanoate [or malonic semialdehyde], and vice versa. Expression or increased expression of BAPAT, for example in an *Aspergillus* also expressing HPDH and panD and having a genetically inactivated cadA gene (ΔcadA), results in a fungus that has an ability to produce more 3-HP than the parent strain (such as at least 20%, at least 30%, at least 40%, 50%, at least 60% at least 70%, at least 100%, at least 200%, at least 300%, or at least 400% more than a parent strain under the same growing conditions).

BAPAT sequences are publicly available. For example, GenBank® Accession Nos: ACMS01000158.1 (complement (10606 . . . 11961)) and EEL86940.1 disclose *Bacillus cereus* AH1272 BAPAT nucleic acid and protein sequences, respectively (SEQ ID NOS: 55 and 56); GenBank® Accession Nos. DF820429.1 (complement (241627 . . . 242967)) and GAK28710.1 disclose exemplary *Serratia liquefaciens* FK01 BAPAT nucleic acid and protein sequences, respectively; and GenBank Accession Nos: LGUJ01000001.1 complement (92812 . . . 94140) and KOY12524.1 disclose exemplary *Bradyrhizobium diazoefficiens* BAPAT nucleic acid and protein sequences, respectively. However, one skilled in the art will appreciate that in some examples, a BAPAT sequence can include variant sequences (such as allelic variants and homologs) that retain BAPAT activity and when expressed in an *Aspergillus* also expressing HPDH and panD and with a genetically inactivated cadA gene (ΔcadA), results in a fungus that has an ability to produce more 3-HP than the parent strain (such as at least 20%, at least 30%, at least 40%, 50%, at least 60% at least 70%, at least 100%, at least 200%, at least 300%, or at least 400% more than a parent strain under the same growing conditions).

cadA (cis-aconitic acid decarboxylase): The cadA gene encodes an enzyme (EC 4.1.1.6) that catalyzes the chemical reaction cis-aconitate⇆itaconate+$CO_2$. The term cadA (or cadA) includes any cadA gene (such as a fungal cadA sequence), cDNA, mRNA, or protein, that is a cadA that can catalyze the decarboxylation of cis-aconitate to itaconate and $CO_2$ and vice versa, and when genetically inactivated results in a fungus that produces more aconitic acid than the parent strain without a genetically inactivated cadA gene (such as at least 20%, at least 30%, at least 50%, at least 60%, at least 75%, at least 100%, at least 200%, at least 500%, or 1000% more than a parent strain under the same growing conditions, for example at day 5 of production). In some examples, a parental strain containing a functional native cadA sequence does not produce detectable aconitic acid. In some examples, genetic inactivation of cadA results in a fungus that produces more trans-aconitic acid than cis-aconitic acid at day 10 of production, (such as at least 2-fold, at least 3-fold, at least 4-fold, or at least 5-fold more at day 10 of production).

cadA sequences are publicly available for many species of *Aspergillus*. For example, GenBank® Accession Nos: AB326105.1 and BAG49047.1 disclose *Aspergillus terreus* cadA nucleic acid and protein sequences, respectively (SEQ ID NOS: 49 and 50); GenBank® Accession Nos: XM_025706777.1 and XP_025563141.1 disclose *Aspergillus* vadensis CBS 113365 cadA nucleic acid and protein sequences, respectively (SEQ ID NOS: 51 and 52); and GenBank® Accession Nos: XM_025663103.1 and XP_025520527.1 disclose *Aspergillus piperis* CBS 112811 cadA nucleic acid and protein sequences, respectively. However, one skilled in the art will appreciate that in some examples, a cadA sequence can include variant sequences (such as allelic variants and homologs) that retain cadA activity but when genetically inactivated in *Aspergillus* results in a fungus that has an ability to produce more aconitic acid than the parent strain without a genetically inactivated cadA gene (such as at least 20%, at least 30%, at least 50%, at least 60%, at least 75%, at least 100%, at least 200%, at least 500%, or 1000% more than a parent strain under the same growing conditions, for example at day 5 of production).

Detectable: Capable of having an existence or presence ascertained. For example, production of aconitic acid or 3-HP is detectable if the signal generated is strong enough to be measurable.

Exogenous: The term "exogenous" as used herein with reference to nucleic acid and a particular cell refers to any nucleic acid that does not originate from that particular cell as found in nature. Thus, a non-naturally-occurring nucleic acid is considered to be exogenous to a cell once introduced into the cell. A nucleic acid that is naturally-occurring also can be exogenous to a particular cell. For example, an entire chromosome isolated from cell X is an exogenous nucleic acid with respect to cell Y once that chromosome is introduced into cell Y, even if X and Y are the same cell type.

In some examples, the panD, BAPAT, and HPDH nucleic acid or protein expressed in an *Aspergillus terreus* or *Aspergillus pseudoterreus* fungi does not naturally occur in the *Aspergillus terreus* or *Aspergillus pseudoterreus* fungi and is therefore exogenous to that fungi. For example, the panD, BAPAT, and HPDH nucleic acid molecule introduced into an *Aspergillus terreus* or *Aspergillus pseudoterreus* fungi can be from another organism, such as a bacterial panD, BAPAT, and HPDH sequence.

Genetic enhancement or up-regulation: When used in reference to the expression of a nucleic acid molecule, such as a gene, refers to any process which results in an increase in production of a gene product. A gene product can be RNA (such as mRNA, rRNA, tRNA, and structural RNA) or protein. Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene up-regulation can include inhibition of repression as well as expression above an existing level. Examples of processes that increase translation include those that increase translational initiation, those that increase translational elongation and those that increase mRNA stability. In one example, additional copies of genes are introduced into a cell in order to increase expression of that gene in the resulting transgenic cell.

Gene up-regulation includes any detectable increase in the production of a gene product. In certain examples, production of a gene product increases by at least 1.5-fold, at least 2-fold, or at least 5-fold), such as aspartate decarboxylase (panD), β-alanine-pyruvate aminotransferase (BAPAT), and 3-hydroxypropionate dehydrogenase (HPDH). For example, expression of a panD, BAPAT, and HPDH genes in *Aspergillus* (e.g., *A. terreus*) results in an *Aspergillus* strain having increased levels of the panD, BAPAT, and HPDH proteins, respectively, relative to the parent strain, which can permit the recombinant fungus to produce 3-HP. Genetic enhancement is also referred to herein as "enhancing or increasing expression."

Genetic inactivation or down-regulation: When used in reference to the expression of a nucleic acid molecule, such as a gene, refers to any process which results in a decrease in production of a gene product. A gene product can be RNA (such as mRNA, rRNA, tRNA, and structural RNA) or protein. Therefore, gene down-regulation or deactivation includes processes that decrease transcription of a gene or translation of mRNA.

For example, a mutation, such as a substitution, partial or complete deletion, insertion, or other variation, can be made to a gene sequence that significantly reduces (and in some cases eliminates) production of the gene product or renders the gene product substantially or completely non-functional. For example, a genetic inactivation of the cadA gene in *Aspergillus* (e.g., *A. pseudoterreus*) results in *Aspergillus* having a non-functional or non-existent cadA protein, which results in the recombinant fungus to produce more aconitic acid. Genetic inactivation is also referred to herein as "functional deletion".

Isolated: To be significantly separated from other agents. An "isolated" biological component (such as a nucleic acid molecule or protein) has been substantially separated, produced apart from, or purified away from other biological components in the cell of the organism in which the component occurs, for example, other chromosomal and extra-chromosomal DNA and RNA, and proteins. Nucleic acid molecules and proteins which have been "isolated" include nucleic acid molecules and proteins purified by standard purification methods. The term also embraces nucleic acid molecules and proteins prepared by recombinant expression in a host cell as well as chemically synthesized proteins and nucleic acids. Samples of isolated biological components include samples of the biological component wherein the biological component represents greater than 90% (for example, greater than 95%, such as greater than 98%) of the sample.

An "isolated" microorganism (such as a ΔcadA strain of *Aspergillus*) has been substantially separated or purified away from microorganisms of different types, strains, or species. Microorganisms can be isolated by a variety of techniques, including serial dilution and culturing and resistance to certain chemicals, such as antibiotics. In some examples, an isolated ΔcadA strain of *Aspergillus* is at least 90% (for example, at least 95%, as at least 98%, at least 99%, or at least 99.99%) pure.

Mutation: A change in a nucleic acid sequence (such as a gene sequence) or amino acid sequence, for example as compared to a nucleic acid or amino acid sequence present in a wild-type or native organism. In particular examples, a mutation is introduced into a cadA gene in *Aspergillus*. Mutations can occur spontaneously, or can be introduced, for example using molecular biology methods (e.g., thereby generating a recombinant or transformed cell or microorganism). In particular examples, a mutation includes one or more nucleotide substitutions, deletions, insertions, or combinations thereof. In particular examples, the presence of one or more mutations in a gene can significantly inactivate and reduce expression of that gene.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. In some examples, a promoter is bi-directional. Native and non-native promoters can be used to drive expression of a gene, such as panD, BAPAT, and HPDH. Exemplary promoters that can be used include but are not limited to: enol promoter from *A. niger*, and dth1 from *A. nidulans* or *A. niger.*

Examples of promoters include, but are not limited to the SV40 promoter, the CMV enhancer-promoter, and the CMV enhancer/β-actin promoter. Both constitutive and inducible promoters can be used in the methods provided herein (see e.g., Bitter et al., *Methods in Enzymology* 153:516-544, 1987). Also included are those promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Recombinant: A recombinant nucleic acid molecule or protein is one that has a sequence that is not naturally occurring or has a sequence that is made by an artificial combination of two otherwise separated segments of sequence. In particular examples, this artificial combination is accomplished by chemical synthesis or by the artificial manipulation of isolated segments of nucleic acids, for example, by genetic engineering techniques such as those described in Sambrook et al. (ed.), Molecular Cloning: A Laboratory Manual, 3d ed., vol. 1-3, Cold Spring Harbor Laboratory Press, Cold Spring Harbor, N Y, 2001. The term recombinant includes nucleic acid molecules that have been altered solely by addition, substitution, or deletion of a portion of the nucleic acid molecule. A recombinant or transformed organism or cell, such as a recombinant *Aspergillus*, is one that includes at least one exogenous nucleic acid molecule, such as one used to genetically inactivate an endogenous cadA gene, and one used to express a non-native protein, such as exogenous panD, BAPAT, and HPDH nucleic acid coding sequences.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q -1-r 2.

To compare two amino acid sequences, the options of B12seq can be set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, 80%, 85%, 90%, 95%, or 99% sequence identity.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, 70%, 80%, 90%, 95%, 98%, or 99% sequence identity determined by this method.

One of skill in the art will appreciate that these sequence identity ranges are provided for guidance only; it is possible that strongly significant homologs could be obtained that fall outside the ranges provided. Thus, a variant cadA, panD, BAPAT, or HPDH protein or nucleic acid molecule that can be used with the organisms and methods of the present disclosure can have at least 80%, at least 85%, at least 90%, at least 91%, at least 92%, at least 93%, at least 94%, at least 95%, at least 96%, at least 97%, at least 98% or at least 99% sequence identity to the SEQ ID NOs: and GenBank® Accession Nos. provided herein.

Transformed: A cell, such as a fungal cell, into which a nucleic acid molecule has been introduced, for example by molecular biology methods. As used herein, the term transformation encompasses all techniques by which a nucleic acid molecule might be introduced into such a cell, including, but not limited to chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses. In one example, the protoplast transformation provide herein, such as in Example 1, is used.

Vector: A nucleic acid molecule as introduced into a host cell, thereby producing a transformed or recombinant host cell. A vector may include nucleic acid sequences that permit it to replicate in the host cell, such as an origin of replication. A vector may also include a panD, BAPAT, or HPDH coding sequence, or a sequence used to genetically inactivate cadA for example in combination with a promoter, and/or selectable marker genes, and other genetic elements. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. In one example, a vector is a plasmid.

Overview

The filamentous fungus *Aspergillus pseudoterreus* has been used for industrial production of itaconic acid. cis-aconitic acid decarboxylase (cadA) is the key enzyme in itaconic acid production. The itaconic acid biosynthesis cluster is composed of genes tf, mttA, cadA and mfsA. As shown in FIG. 1, itaconic acid (IA) is produced from glucose. Glucose is utilized in the cell mainly by the glycolytic pathway and metabolized to pyruvate, which forms citric acid. cis-aconitic acid is derived from citric acid as a primary precursor of IA. cis-aconitic acid decarboxylase (cadA) removes carbon dioxide from cis-aconitic acid and forms itaconic acid. However, cadA is localized in the cytosol, while cis-aconitic acid is formed from the TCA cycle in the mitochondria. mttA is localized on the mitochondrial membrane and functioned to transport cis-aconitic acid from mitochondria to cytosol. Another transporter, mfsA is also an organic acid transporter that may be involved in exporting itaconic acid out of cells.

The first demonstration of genetically inactivating the cadA gene in *Aspergillus pseudoterreus* is shown herein. In the cadA deletion strain (ΔcadA), no more itaconic acid is produced. At the same time significant amount of cis-aconitic acid and trans-aconitic acid are detected. Blocking the itaconic acid production pathway permits the carbon to be diverted towards other organic acid production. The ΔcadA *Aspergillus* can be used as a host for chemical platform, and provides a new way to produce aconitic acid and other organic acids (for example by expressing other genes needed for procution of those acids, such as panD, BAPAT, and HPDH for 3-HP production). This strain works as biocatalyst that converts biomass into aconitic acid through bioproduction method at room temperature (such as about 20-35° C.) and ordinary pressure (such as about 1 atm). Current processes of aconitic acid production include chemical synthesis that require high temperatures and harmful reagents.

The EST data provided herein demonstrated that four genes, tf, cadA, mttA and mfsA show high transcription frequency after IA production starts, but not before IA production begins. The high expression of these genes persists through the production process. Genes upstream and downstream of the cluster did not show expression differences before and after production. One gene downstream next to mfsA, a p450 enzyme, also showed high expression after IA production started, however, deletion of this gene did not effect IA yield.

Correlations between the IA gene cluster and IA production were further investigated by constructing deletion strains. In a Δcad strain, no IA was detected, while trace amounts of IA were detected in an mttA knockout. IA production in an mfsA deletion strain decreased one third compared with wild type. This indicates mfsA can transport IA across the cell membrane. In the Δtf strain, IA production decreased eight fold and slowed the production rate compared to wild type. Also in the tf deletion strain, expression of cadA, mttA and mfsA significantly decreased. RT-PCR results indicated that the expression level of genes in the IA cluster was regulated by tf, which is turned on by IA production conditions.

The ΔcadA strain produced aconitc acid. During the production, cis-aconitic acid was detected first, followed by the appearance of trans-aconitic acid. cis-aconitic acid levels remained consistent from day 5 forward. The trans-aconitic acid levels continued to increase from days 4 to 10. By day 10, more than 10 g/L trans-aconitic acid was detected in the supernatant. In the ΔcadA strain, cis-aconitic acid decarboxylase is not produced, and the cis-aconitic acid cannot be converted to itaconic acid by decarboxylation and accumulates in the cell. cis-aconitic acid was transported outside the cell. cis-aconitic acid is not stable in the acid solution and is rapidly converted into trans-aconitic acid.

Aconitic acid is an unsaturated tricarcoxylic acid and is noted as a top 30 potential building block by United States Department of Energy (DOE). Trans-aconitic acid can be used to make polymers. Currently, trans-aconitc acid is produced by chemical synthesis and requires high temperature and harmful solvents. Generation of trans-aconitic acid has been achieved by metabolic engineering aconitase isomerase from *Pseudomonas* sp. WU-0701 into *E. coli*. However, the substrate for the recombinant *E. coli* to produce trans-aconitic acid is citric acid, which has to be generated first from fermentation. In contrast, the disclosed ΔcadA fungi can produce trans-aconitic acid directly from renewable biomass substrates. Also since the cadA is not functional and precursors from TAC cycle accumulate in the cell, the carbon can be rerouted to generate other organic acid since *A. pseudoterreus* is industrial filamentous fungi and tolerant to low pH.

Based on these observations, provided herein are isolated recombinant (i.e., transformed) *Aspergillus* fungi that include a genetic inactivation (also referred to as a functional deletion) of an endogenous cis-aconitic acid decarboxylase (cadA) gene. Such fungi are referred to herein as ΔcadA fungi. Exemplary *Aspergillus* species that can be used include *Aspergillus pseudoterreus* and *Aspergillus terreus*. In some examples, the endogenous cadA gene is genetically inactivated by mutation (such as a complete or partial deletion of the cadA gene) or by insertional mutation (such as by insertion of another nucleic acid molecule into the cadA gene, such as an antibiotic resistance marker).

In some examples, the cadA gene prior to its genetic inactivation encodes a protein having at least 80%, at least 90%, at least 95%, at least 98%, at least 99%, or 100% sequence identity to SEQ ID NO: 50 or 52. In some examples, the cadA gene (or its coding sequence) prior to its genetic inactivation comprises at least 80%, at least 90%, at least 95%, at least 98%, at least 99%, or 100% sequence identity to SEQ ID NO: 49, 51, 59 or 92.

The disclosed ΔcadA fungi can include other exogenous genes to express proteins needed to permit the fungi to produce other organic acids. For example, the disclosed ΔcadA fungi can further include an exogenous nucleic acid molecule encoding aspartate 1-decarboxylase (panD), an exogenous nucleic acid molecule encoding β-alanine-pyruvate aminotransferase (BAPAT), and an exogenous nucleic acid molecule encoding 3-hydroxypropionate dehydrogenase (HPDH). panD, BAPAT, and HPDH coding sequences can be part of a one or more nucleic acid molecules, such as a vector. In addition, expression of the panD, BAPAT, and HPDH coding sequences can be driven by one or more promoters, such as a bi-directional promoter. In some examples, the promoter is native to the gene it is expressing. In some examples, the promoter is from *A. niger*. In some examples, the panD, BAPAT, and/or HPDH coding sequences are inserted into the cadA gene, genetically inactivating cadA. In some examples, the exogenous nucleic acid molecule encoding panD has at least 80%, at least 90%, at least 95%, at least 98%, at least 99%, or 100% sequence identity to SEQ ID NO: 53 or 65, and/or encodes a panD protein comprising at least 80%, at least 90%, at least 95%, at least 98%, at least 99%, or 100% sequence identity to SEQ ID NO: 54. In some examples, the exogenous nucleic acid molecule encoding BAPAT has at least 80%, at least 90%, at least 95%, at least 98%, at least 99%, or 100% sequence identity to SEQ ID NO: 55, and/or encodes a BAPAT protein having at least 80%, at least 90%, at least 95%, at least 98%, at least 99%, or 100% sequence identity to SEQ ID NO: 56. In some examples, the exogenous nucleic acid molecule encoding HPDH has at least 80%, at least 90%, at least 95%, at least 98%, at least 99%, or 100% sequence identity to SEQ ID NO: 57, and/or encodes a HPDH protein having at least 80%, at least 90%, at least 95%, at least 98%, at least 99%, or 100% sequence identity to SEQ ID NO: 58.

The disclosure also provides compositions that include the ΔcadA fungi, and the ΔcadA fungi expressing other genes (such as panD, BAPAT, and HPDH). Such a composition can include a solid or liquid culture or growth media, such as complete media, minimal media, or Riscaldati medium (such as modified Riscaldati medium with 20× trace elements).

The disclosure also provides kits that include the ΔcadA fungi, and the ΔcadA fungi expressing other genes (such as panD, BAPAT, and HPDH). Such a kits can include a solid or liquid culture or growth media, such as complete media, minimal media, or Riscaldati medium (such as modified Riscaldati medium with 20× trace elements).

Also provided are methods of using the disclosed ΔcadA fungi to make aconitic acid. Such a method can include culturing the recombinant *Aspergillus* ΔcadA fungi under conditions that permit the fungus to make aconitic acid, such as growth in Riscaldati medium, thereby making aconitic acid. In some examples the aconitic acid generated is cis-aconitic acid, trans-aconitic acid, or both. In some examples, the fungi are cultured at room temperature (e.g., 20-35° C.) at normal atmospheric pressure (e.g., 1 atm). In some examples, the method includes purifying or isolating the aconitic acid, for example from the culture media or from the cultured fungus. In some examples, the aconitic acid is isolated at least 2 days, at least 3 days, at least 5 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Also provided are methods of using the disclosed ΔcadA fungi expressing panD, BAPAT, and HPDH to make 3-HP. Such a method can include culturing the recombinant *Aspergillus* ΔcadA fungi expressing panD, BAPAT, and HPDH under conditions that permit the fungus to make 3-HP, such as growth in Riscaldati medium (such as modified Riscaldati medium with 20× trace elements), thereby making 3-HP. In some examples, the fungi are cultured at room temperature (e.g., 20-35° C.) at normal atmospheric pressure (e.g., 1 atm). In some examples, the method includes purifying or isolating the 3-HP, for example from the culture media or from the cultured fungus. In some examples, the 3-HP is isolated at least 2 days, at least 3 days, at least 5 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Recombinant ΔcadA Fungi

The present disclosure provides isolated recombinant *Aspergillus* fungi having its endogenous cadA gene genetically inactivated (e.g., functional deletion) of. Such fungi are referred to herein as ΔcadA fungal strains. It is shown herein that ΔcadA *Aspergillus* strains have increased aconitic acid production as compared to *Aspergillus* having native levels of cadA expression.

Any variety or strain of *Aspergillus* can be used. In particular examples, the *Aspergillus* fungus is *A. terreus* or *A. pseudoterreus*, as well as particular strains thereof (for example *A. terreus* NRRL 1960, *A. pseudoterreus* ATCC 32359).

In addition, any method for genetic inactivation can be used, as long as the expression of the cadA gene is significantly reduced or eliminated, or the function of the cadA protein is significantly reduced or eliminated. In particular examples, the cadA gene is genetically inactivated by complete or partial deletion mutation or by insertional mutation. In some examples genetic inactivation need not be 100%. In some embodiments, genetic inactivation refers to at least 50%, at least 60%, at least 70%, at least 80%, at least 90%, or at least 95% gene or protein inactivation. The term "reduced" or "decreased" as used herein with respect to a cell and a particular gene or protein activity refers to a lower level of activity than that measured in a comparable cell of the same species. For example, a particular *A. terreus* or *A. pseudoterreus* lacking cadA activity has reduced cadA activity if a comparable *A. terreus* or *A. pseudoterreus* not having an cadA genetic inactivation has detectable cadA activity.

cadA sequences are disclosed herein and others are publicly available, for example from GenBank or EMBL. In some examples, the cadA gene functionally deleted encoded a protein having at least 80%, at least 90%, at least 95%, at least 97%, at least 98%, at least 99%, or 100% sequence identity to SEQ ID NO: 50 or 52 prior to is genetic inactivation. In some examples, the endogenous cadA gene functionally deleted comprises at least 80%, at least 90%, at least 95%, at least 97%, or at least 98% sequence identity to SEQ ID NO: 49, 51, 59, or 92 prior to is genetic inactivation.

The genetic inactivation of cadA results in many phenotypes in the recombinant ΔcadA *Aspergillus*, such as *A. terreus* or *A. pseudoterreus*. For example, ΔcadA mutants can have one or more of the following phenotypes: produces at least 2-fold, at least 3-fold, at least 3.5 fold, at least 5-fold, at least 8-fold, or at least 10-fold more total aconitic acid than a wild-type *Aspergillus terreus* or *Aspergillus pseudoterreus* (for example at day 3, 4, 5, 6, 7, 8, 9 or 10 of production); produces at least 2-fold more cis-aconitic acid at day 5, 6, 7, 8, 9, or 10 of culturing in Riscaldati medium than a wild-type *Aspergillus terreus* or *Aspergillus pseudoterreus*; produces at least 2-fold, at least 3-fold, at least 5-fold, or at least 10-fold more trans-aconitic acid at day 10 of culturing in Riscaldati medium than a wild-type *Aspergillus terreus* or *Aspergillus pseudoterreus*; or combinations thereof. In some examples, such increases are relative to *Aspergillus terreus* strain ATCC 32359 grown under the same conditions as the ΔcadA mutant. In some examples, an increased total aconitic acid production by ΔcadA fungi occurs at least 3 days (such as at least 4, 5, 6, 7, 8, 9, or 10 days) after inoculation in Riscaldati medium (such as at least 0.5 g/L aconitic acid or at least 1 g/L aconitic acid), as compared to no detectable aconitic acid produced by *Aspergillus terreus* strain ATCC 32359 at the same time point.

Additional genes can also be inactivated in the ΔcadA fungi, wherein the additional genes may or may not provide additional enhancement of aconitic acid production to the fungus. In one example, the ΔcadA fungi includes overexpressed or upregulated aconitic acid transporters.

In some examples, ΔcadA fungi include one or more additional exogenous nucleic acid molecules, for example to permit production of other organic acids by the recombinant fungi. In one example, the ΔcadA fungi includes an exogenous nucleic acid molecule encoding aspartate decarboxylase (panD), an exogenous nucleic acid molecule encoding β-alanine-pyruvate aminotransferase (BAPAT), and an exogenous nucleic acid molecule encoding 3-hydroxypropionate dehydrogenase (HPDH). Such exogenous nucleic acid molecules can be part of one or more exogenous nucleic acid molecules (such as 1, 2 or 3 exogenous nucleic acid molecules). In some examples, exogenous nucleic acid molecules can be part of a vector, such as a plasmid or viral vector. In some examples, expression of the exogenous nucleic acid molecules is driven by one or more promoters, such as a constitutive or inducible promoter, or a bi-directional promoter. In some examples, the promoter used to drive expression of panD, BAPAT, and HPDH is a native promoter (e.g., native to the panD, BAPAT, and HPDH gene expressed). In other examples, the promoter used to drive expression of panD, BAPAT, and HPDH is a non-native promoter (e.g., exogenous to the panD, BAPAT, and HPDH gene expressed). In some examples, such a ΔcadA fungi expressing panD, BAPAT, and HPDH are used to produce 3-HP.

A. Methods of Functionally Deleting cadA

As used herein, an "inactivated" or "functionally deleted" cadA gene means that the cadA gene has been mutated, for example by insertion, deletion, or substitution (or combinations thereof) of one or more nucleotides such that the mutation substantially reduces (and in some cases abolishes) expression or biological activity of the encoded cadA gene product. The mutation can act through affecting transcription or translation of the cadA gene or its mRNA, or the mutation can affect the cadA polypeptide product itself in such a way as to render it substantially inactive.

In one example, a strain of *Aspergillus* is transformed with a vector which has the effect of down-regulating or otherwise inactivating a cadA gene. This can be done by mutating control elements such as promoters and the like which control gene expression, by mutating the coding region of the gene so that any protein expressed is substantially inactive, or by deleting the cadA gene entirely. For example, a cadA gene can be functionally deleted by complete or partial deletion mutation (for example by deleting a portion of the coding region of the gene) or by insertional mutation (for example by inserting a sequence of nucleotides into the coding region of the gene, such as a sequence of about 1-5000 nucleotides). In one example, the cadA gene is genetically inactivated by inserting coding sequences for panD, BAPAT, and/or HPDH. Thus, the disclosure provides transformed fungi that include at least one exogenous nucleic acid molecule which genetically inactivates a cadA gene. In one example, such a transformed cell produces more aconitic acid, for example relative to a comparable fungus with a native or wild-type cadA sequence.

In particular examples, an insertional mutation includes introduction of a sequence that is in multiples of three bases (e.g., a sequence of 3, 9, 12, or 15 nucleotides) to reduce the possibility that the insertion will be polar on downstream genes. For example, insertion or deletion of even a single nucleotide that causes a frame shift in the open reading frame, which in turn can cause premature termination of the encoded cadA polypeptide or expression of a substantially inactive polypeptide. Mutations can also be generated through insertion of foreign gene sequences, for example the insertion of a gene encoding antibiotic resistance (such as hygromycin or bleomycin), or panD, BAPAT, and/or HPDH coding sequences.

In one example, genetic inactivation is achieved by deletion of a portion of the coding region of the cadA gene. For example, some, most (such as at least 50%) or virtually the entire coding region can be deleted. In particular examples, about 5% to about 100% of the gene is deleted, such as at least 20% of the gene, at least 40% of the gene, at least 75% of the gene, or at least 90% of the cadA gene.

Deletion mutants can be constructed using any of a number of techniques. In one example, homologous double crossover with fusion PCR products is employed to genetically inactivate one or more genes in *Aspergillus*. A specific example of such a method is described in Example 1 below.

In one example, a strategy using counterselectable markers can be employed which has been utilized to delete genes. For a review, see Reyrat et al. (*Infec. Immun.* 66:4011-4017, 1998). In this technique, a double selection strategy is employed wherein a plasmid is constructed encoding both a selectable and counterselectable marker, with flanking DNA sequences derived from both sides of the desired deletion. The selectable marker is used to select for fungi in which the plasmid has integrated into the genome in the appropriate location and manner. The counterselectable marker is used to select for the very small percentage of fungi that have spontaneously eliminated the integrated plasmid. A fraction of these fungi will then contain only the desired deletion with no other foreign DNA present.

In another technique, the cre-lox system is used for site specific recombination of DNA (for example see Steiger et al., *Appl. Environ. Microbiol.* 77(1):114, 2011). The system includes 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, the targeted gene of interest (e.g., cadA) can be deleted in the *Aspergillus* genome and to replace it with a selectable marker (for example a gene coding for kanamycin resistance) that is flanked by the lox sites. Transient expression (by electroporation of a suicide plasmid containing the cre gene under control of a promoter that functions in *Aspergillus*) of the cre recombinase should result in efficient elimination of the lox flanked marker. This process will produce a mutant containing the desired deletion mutation and one copy of the lox sequence.

In another method, a cadA gene sequence in the *Aspergillus* genome is replaced with a marker gene, such as green fluorescent protein, β-galactosidase, or luciferase. In this technique, DNA segments flanking a desired deletion are prepared by PCR and cloned into a suicide (non-replicating) vector for *Aspergillus*. An expression cassette, containing a promoter active in *Aspergillus* and the appropriate marker gene, is cloned between the flanking sequences. The plasmid is introduced into wild-type *Aspergillus*. Fungi that incorporate and express the marker gene are isolated and examined for the appropriate recombination event (replacement of the wild type cadA gene with the marker gene).

Thus, for example, a fungal cell can be engineered to have a disrupted cadA gene using common mutagenesis or knockout technology. (Methods in Yeast Genetics (1997 edition), Adams, Gottschling, Kaiser, and Sterns, Cold Spring Harbor Press, 1998; Datsenko and Wanner, *Proc. Natl. Acad. Sci. USA* 97: 6640-5, 2000; and Dai et al., *Appl. Environ. Microbiol.* 70(4):2474-85, 2004). Alternatively, antisense technology can be used to reduce or eliminate the activity of cadA. For example, a fungal cell can be engineered to contain a cDNA that encodes an antisense molecule that prevents cadA from being translated. The term "antisense molecule" encompasses any nucleic acid molecule or nucleic acid analog (e.g., peptide nucleic acids) that contains a sequence that corresponds to the coding strand of an endogenous cadA gene. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axehead structures, provided the molecule cleaves RNA. Further, gene silencing can be used to reduce the activity of cadA.

In one example, to genetically inactivate cadA in *A. pseudoterreus* or *A. terreus*, protoplast transformation is used, for example as described in Example 1. For example, conidia of *A. pseudoterreus* or *A. terreus* are grown in liquid complete medium at room temperature (e.g., about 20-35° C., such as 30° C.) and grown for at least 12 hours (such as at least 16 hours, or at least 18 hours, such as 12-24 hours, or 16-18 hours), at least 100 rpm, such as at least 150 rpm, for example 100 to 200 rpm. The resulting mycelia are subsequently harvested, for example by filtration. Protoplasts are prepared, for example by treating the harvested mycelia with a lysing enzyme (for example in an osmotic wash buffer for at least 30 min, at least 60 min, at least 120 min, or at leave 240 min, such as 2 h). The resulting protoplasts are collected (e.g., by filtering). Protoplasts can be washed, for example with a Washing Solution (0.6M KCl, 0.1M Tris/HCl, pH 7.0) and Conditioning Solution (0.6M KCl, 50 mM $CaCl_2$, 10 mM Tris/HCl, pH 7.5). The protoplasts are transformed, for example in the conditioning solution. In some examples, at least 0.5 ug, at least 1 ug, or at least 2 ug of DNA (such as 1-2 ug DNA) is added to at least $10^6$ protoplasts (such as at least $10^7$ or $2\times10^7$ protoplasts). Polyethylene glycol (PEG), such as PEG8000 is added (such as 25% PEG8000, 0.6M KCl, 50 mM $CaCl_2$, 10 mM Tris/HCl, and pH 7.5) and the reaction incubated for at least 5 min (such as at least 10 min, at least 20 min, or at least 30 min, such as 10-30 min, 15-20 min, or 20 min) on ice. Additional PEG solution can be added and the reaction incubated for at least 1 min, at least 3 min, or at least 5 min, on ice. Conditioning Solution is added to the reaction, and the protoplast suspension mixed with warm selection agar (Minimal media+0.6M KCl+1.5% Agar+100 ug/ml hygromycin) (such as at 50° C.), and poured directly onto petri dish plates and allowed to solidify. Solidified plates can be inverted and incubated overnight at room temperature (e.g., about 20-35° C., such as 30° C.). The following day, the plates can be overlaid with Minimal Medium containing a selection antibiotic, such as hygromycin. Colonies appear after 3-4 days. Transformants can be excised and transferred to MM plate containing the selection antibiotic.

B. Measuring Gene Inactivation

A fungus having an inactivated cadA gene can be identified using known methods. For example, PCR and nucleic acid hybridization techniques, such as Northern and Southern analysis, can be used to confirm that a fungus has a genetically inactivated cadA gene. In one example, real-time reverse transcription PCR (qRT-PCR) is used for detection and quantification of targeted messenger RNA, such as mRNA of cadA gene in the parent and mutant strains as grown at the same culture conditions. Immunohisto-chemical and biochemical techniques can also be used to determine if a cell expresses cadA by detecting the expression of the cadA peptide encoded by cadA. For example, an antibody having specificity for cadA can be used to determine whether or not a particular fungus contains a functional nucleic acid encoding cadA protein. Further, biochemical techniques can be used to determine if a cell contains a cadA gene inactivation by detecting a product produced as a result of the lack of expression of the peptide. For example, production of aconitic acid by *A. terreus* or *A. pseudoterreus* can indicate that such a fungus contains an inactivated cadA gene.

C. Measuring Aconitic Acid Production

Methods of determining whether a genetic inactivation of cadA in *Aspergillus*, such as *A. terreus* or *A. pseudoterreus*. increases aconitic acid production, for example relative to the same strain of *A. terreus* or *A. pseudoterreus* with a native cadA sequence (such as a parental strain), are provided herein. Although particular examples are disclosed herein, the methods are not limiting.

For example, production of aconitic acid by *Aspergillus* (such as a ΔcadA strain) can be measured using a spectrophotometric assay, by liquid chromatography (LC), or high-pressure liquid chromatography (HPLC) methods. In some examples, the supernatant of the fungus is analyzed for the presence of aconitic acid. In some examples, the culture media containing the ΔcadA strain is filtered prior to measuring aconitic acid in the culture media (supernatant).

D. cadA Sequences cadA protein and nucleic acid sequences are publicly available and specific examples are provided herein. In addition, cadA sequences can be identified using molecular biology methods.

Examples of cadA nucleic acid sequences are shown in SEQ ID NOS: 49, 51, 59 and 92. However, the disclosure also encompasses variants of SEQ ID NOS: 49, 51, 59 and 92 which encode a functional cadA protein. One skilled in the art will understand variants of the cadA nucleic acid sequences provided herein can be genetically inactivated. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. Such variant cadA nucleic acid molecules can share at least 80%, at least 85%, at least 90%, at least 95%, at least 97%, at least 98%, or at least 99% sequence identity to any cadA nucleic acid sequence, such as SEQ ID NO: 49, 51, 59 or 92.

Examples of cadA protein sequences are shown in SEQ ID NOS: 50 and 52. However, the disclosure also encompasses variants SEQ ID NOS: 50 and 52 which retain cadA activity. One skilled in the art will understand that variants of these cadA enzyme sequences can be inactivated. Variant sequences can be identified, for example by aligning known cadA sequences. Variant sequences may contain a single insertion, a single deletion, a single substitution, multiple insertions, multiple deletions, multiple substitutions, or any combination thereof (e.g., single deletion together with multiple insertions). Such cadA peptides share at least 80%, at least 85%, at least 90%, at least 95%, at least 97%, at least 98%, or at least 99% sequence identity to a cadA protein sequence, such as SEQ ID NO: 50 or 52.

In some examples, a cadA sequence that is to be genetically inactivated encodes or includes one or more conservative amino acid substitutions. A conservative amino acid substitution is a substitution of one amino acid (such as one found in a native sequence) for another amino acid having similar biochemical properties. Typically, conservative substitutions have little to no impact on the activity of a resulting peptide. In one example, a cadA sequence (such as SEQ ID NO: 50 or 52) includes one or more amino acid substitutions, such as conservative substitutions (for example at 1, 2, 5 or 10 residues). Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Be; Ile or Val for Leu; Arg or Gln for Lys; Leu or Be for Met; Met, Leu or Tyr for Phe; Thr for Ser; Ser for Thr; Tyr for Trp; Trp or Phe for Tyr; and Ile or Leu for Val. Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

The cadA gene inactivated in a fungus, in particular examples, includes a sequence that encodes a cadA protein having at least at least 80%, at least 85%, at least 90%, at least 95%, at least 97%, at least 98%, at least 99%, or 100% sequence identity to a cadA protein sequence, such as SEQ ID NO: 50 or 52, wherein the protein can catalyze the decarboxylation of cis-aconitate to itaconate and $CO_2$ and vice versa. In a specific example, the cadA gene inactivated in a fungus encodes a cadA protein shown in SEQ NO: 50 or 52.

The cadA gene that is to be inactivated in a fungus, in particular examples, includes a sequence (such as a coding sequence) having at least at least 80%, at least 85%, at least 90%, at least 95%, at least 97%, at least 98%, at least 99%, or 100% sequence identity to a cadA nucleic acid sequence, such as SEQ ID NO: 49, 51, 59, or 92, and encodes a cadA protein that can catalyze the decarboxylation of cis-aconitate to itaconate and $CO_2$ and vice versa. In a specific example, cadA gene inactivated in a fungus is the sequence of SEQ ID NO: 2 or 4.

One skilled in the art will appreciate that additional cadA sequences can be identified. For example, cadA nucleic acid molecules that encode a cadA protein can be identified and obtained using molecular cloning or chemical nucleic acid synthesis procedures and techniques, including PCR. In addition, nucleic acid sequencing techniques and software programs that translate nucleic acid sequences into amino acid sequences based on the genetic code can be used to determine whether or not a particular nucleic acid has any sequence homology with known cadA sequences. Sequence alignment software such as MEGALIGN (DNASTAR, Madison, Wis., 1997) can be used to compare various sequences.

In addition, nucleic acid hybridization techniques can be used to identify and obtain a nucleic acid molecule that encodes a cadA protein. Briefly, any known cadA nucleic acid molecule, or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is a cadA protein.

E. panD, BAPAT, and HPDH Sequences panD, BAPAT, and HPDH protein and nucleic acid sequences are publicly available and specific examples are provided herein. In addition, panD, BAPAT, and HPDH sequences can be identified using molecular biology methods.

Exemplary of panD coding sequences are shown in SEQ ID NO: 53 and 65. However, the disclosure also encompasses variants of SEQ ID NO: 53 and 65 which encode a functional panD protein. Exemplary of BAPAT coding sequences are shown in SEQ ID NO: 55 and 71. However, the disclosure also encompasses variants of SEQ ID NO: 55 and 71 which encode a functional BAPAT protein. Exemplary of HPDH coding sequences are shown in SEQ ID NO: 57 and 80. However, the disclosure also encompasses variants of SEQ ID NO: 57 and 80 which encode a functional HPDH protein.

One skilled in the art will understand variants of the panD, BAPAT, and HPDH nucleic acid sequences provided herein can be introduced into an *Aspergillus* fungus, such as one that is ΔcadA, such as inserting panD, BAPAT, and HPDH expression sequences into the native cadA gene to inactivate it. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. In some examples, a panD, BAPAT, and HPDH sequence that is to be expressed in an *Aspergillus* fungus is codon optimized for expression in *Aspergillus*, such as *Aspergillus terreus* or *pseudoterreus*. Such variant panD, BAPAT, and HPDH nucleic acid molecules in some examples share at least 80%, at least 85%, at least 90%, at least 95%, at least 97%, at least 98%, or at least 99% sequence identity to any panD, BAPAT, and HPDH nucleic acid sequence, such as SEQ ID NO: 53, 55, or 57, respectively, or SEQ ID NO: 65, 71, or 80, respectively.

Exemplary panD, BAPAT, and HPDH protein sequences are shown in SEQ ID NOS: 54, 56, and 58, respectively. However, the disclosure also encompasses variants SEQ ID NOS: 54, 56, and 58 which retain panD, BAPAT, and HPDH activity, respectively. One skilled in the art will understand that variants of these panD, BAPAT, and HPDH sequences can be expressed in an *Aspergillus* fungus, such as one that is ΔcadA, Variant sequences can be identified, for example by aligning known panD, BAPAT, and HPDH sequences. Variant sequences may contain a single insertion, a single deletion, a single substitution, multiple insertions, multiple deletions, multiple substitutions, or any combination thereof (e.g., single deletion together with multiple insertions). Such panD, BAPAT, and HPDH peptides expressed in aΔcadA fungus in some examples share at least 80%, at least 85%, at least 90%, at least 95%, at least 97%, at least 98%, or at least 99% sequence identity to a panD, BAPAT, and HPDH protein sequence, such as SEQ ID NO: 54, 56, or 58, respectively.

In some examples, a panD, BAPAT, and HPDH sequence that is to be expressed in an *Aspergillus* fungus encodes or includes one or more conservative amino acid substitutions. In one example, a panD, BAPAT, or HPDH sequence (such as SEQ ID NO: 54, 56, or 58, respectively) includes one or more amino acid substitutions, such as conservative substitutions (for example at 1, 2, 5, or 10 residues). Examples of conservative substitutions are provided elsewhere herein.

The panD, BAPAT, and HPDH gene expressed in a fungus, in particular examples, includes a sequence that encodes a panD, BAPAT, and HPDH protein having at least at least 80%, at least 85%, at least 90%, at least 95%, at least 97%, at least 98%, at least 99%, or 100% sequence identity to a panD, BAPAT, and HPDH protein sequence, such as SEQ ID NO: 54, 56, or 58, respectively, wherein the variant protein has the biological activity of panD, BAPAT, or HPDH, respectively. In a specific example, the panD, BAPAT, and HPDH gene expressed in a ΔcadA fungus encodes the protein shown in SEQ ID NO: 54, 56, and 58, respectively.

One skilled in the art will appreciate that additional panD, BAPAT, and HPDH sequences can be identified. For example, panD, BAPAT, and HPDH nucleic acid molecules that encode a panD, BAPAT, and HPDH protein, respectively can be identified and obtained using molecular cloning or chemical nucleic acid synthesis procedures and techniques, including PCR. In addition, nucleic acid sequencing techniques and software programs that translate nucleic acid sequences into amino acid sequences based on the genetic code can be used to determine whether or not a particular nucleic acid has any sequence homology with panD, BAPAT, or HPDH sequences. Sequence alignment software such as MEGALIGN (DNASTAR, Madison, Wis., 1997) can be used to compare various sequences.

In addition, nucleic acid hybridization techniques can be used to identify and obtain a nucleic acid molecule that encodes a panD, BAPAT, or HPDH protein. Briefly, any known panD, BAPAT, or HPDH nucleic acid molecule, or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is a panD, BAPAT, or HPDH protein.

In one example, exogenous panD, BAPAT, and/or HPDH nucleic acid sequences are introduced into *A. pseudoterreus* or *A. terreus* using protoplast transformation, for example as described in Example 1 (and described above).

F. Methods of Increasing panD, BAPAT, and HPDH Expression

In some examples, a native *A. pseudoterreus* or *A. terreus* fungi does not have or express panD, BAPAT, and/or HPDH nucleic acid sequences. Thus, in some examples, expression of these genes is increased by introducing panD, BAPAT, and/or HPDH nucleic acid coding sequences (such may be codon optimized) into the *A. pseudoterreus* or *A. terreus* fungi.

In some examples, a native *A. pseudoterreus* or *A. terreus* fungi does express native panD, BAPAT, and/or HPDH nucleic acid sequences. Thus, in some examples, expression of these genes is upregulated by introducing additional copies of panD, BAPAT, and/or HPDH nucleic acid coding sequences (such may be codon optimized) into the *A. pseudoterreus* or *A. terreus* fungi. As used herein, "up-regulated" gene means that expression of the gene or gene product (e.g., protein) has been up-regulated, for example by introduction of additional copies of the appropriate gene or coding sequence into the fungus (or other molecular biology methods), such that the introduced nucleic acid sequence is expressed, resulting in increased expression or biological activity of the encoded gene product. In some embodiments, introduction of one or more transgenes including panD, BAPAT, and/or HPDH coding sequences into a native *A. pseudoterreus* or *A. terreus* fungi increases expression of panD, BAPAT, and/or HPDH by at least 20%, at least 40%, at least 50%, at least 100%, at least 150%, at least 200%, at least 300%, or at least 500%, for example relative to the parental fungal strain without the introduced panD, BAPAT, and/or HPDH coding sequences. The term "increased" or "up-regulated" as used herein with respect to a cell and a particular gene or protein activity refers to a higher level of activity than that measured in a comparable cell of the same species. For example, a particular fungi having increased or up-regulated panD, BAPAT, and/or HPDH activity has increased panD, BAPAT, and/or HPDH activity if a comparable fungi having native panD, BAPAT, and/or HPDH activity has less detectable panD, BAPAT, and/or HPDH activity (for example as measured by gene or protein expression).

In one example, a strain of *Aspergillus* is transformed with a vector which has the effect of up-regulating a panD, BAPAT, and/or HPDH gene (such as a native or non-native panD, BAPAT, and/or HPDH gene). This can be done by introducing one or more panD, BAPAT, and/or HPDH coding sequences (such as a gene sequence), whose expression is controlled by elements such as promoters and the like which control gene expression, by introducing a nucleic acid sequence which itself (or its encoded protein) can increase panD, BAPAT, and/or HPDH protein activity in the fungus, or by introducing another molecule (such as a protein or antibody) increases panD, BAPAT, and/or HPDH protein activity in the fungus. For example, a panD, BAPAT, and/or HPDH gene can be up-regulated by introduction of a vector that includes one or more panD, BAPAT, and/or HPDH sequences (such as 1, 2, 3, 4, 5, 6, 7, 8, 9 or 10 panD, BAPAT, and/or HPDH sequences or copies of such sequences) into the desired fungus. In some examples, such panD, BAPAT, and/or HPDH sequences are from different fungal species, can be multiple copies from a single species, or combinations thereof, such as panD, BAPAT, and/or HPDH sequences from at least 2, 3, 4, 5, 6, 7, 8, 9, or 10 different fungal species. In some examples, the panD, BAPAT, and/or HPDH sequence(s) introduced into the fungus is optimized for codon usage. Thus, the disclosure in some examples provides transformed fungi that include at least one exogenous nucleic acid molecule which includes a panD, BAPAT, and/or HPDH gene or coding sequence (such as a nucleic acid sequence encoding SEQ ID NO: 54, 56, or 58, respectively), for example in combination with ΔcadA. In one example, such transformed cells produce more 3HP, for example relative to a comparable fungus with a native cadA.

In one example, the cre-lox system is used for site specific recombination of DNA (for example see Steiger et al., *Appl. Environ. Microbiol.* 77(1):114, 2011). Using recombination techniques, the targeted gene of interest (e.g., cadA) can be deleted in the *Aspergillus* genome and replaced with one or more copies of a non-native panD, BAPAT, and/or HPDH sequence (for example in *A. terreus*, replacing one or both *A. terreus* cadA sequences with panD, BAPAT, and/or HPDH sequences from *A. nidulans* or *A. flavus*) flanked by the lox sites. Transient expression (by electroporation of a suicide plasmid containing the cre gene under control of a promoter that functions in *Aspergillus*) of the cre recombinase should result in efficient elimination of the lox flanked marker. This process will produce a fungus containing the desired insertion mutation and one copy of the lox sequence.

In one example, a transgene is generated and expressed in the desired fungal cell, such as an ΔcadA fungal cell, to increase panD, BAPAT, and HPDH expression. For example, one or more transgenes can include a panD, BAPAT, and HPDH genomic or cDNA sequence (such as one having at least 80%, at least 85%, at least 90%, at least 95%, at least 97%, at least 98%, or at least 99% sequence identity to any panD, BAPAT, and HPDH sequence provided herein), for example operably linked to one or more promoters, such as gpdA and enol. In one example, the promoter has at least 80%, at least 85%, at least 90%, at least 95%, at least 97%, at least 98%, or at least 99% sequence identity to SEQ ID NO: 74 and/or 77. In some examples, the transgene further includes a trpC transcriptional terminator sequence of *A. nidulans*, for example downstream of the panD, BAPAT, and/or HPDH sequence. As an alternative to trpC, other transcriptional terminators can be used, such as promoters which include a transcriptional terminators (e.g., ArsA7, Arsa-37, polyubiquitin (ubi4)). In one example, the trpC transcriptional terminator has at least 80%, at least 85%, at least 90%, at least 95%, at least 97%, at least 98%, or at least 99% sequence identity to SEQ ID NO: 83 or 86. In one example, the trpC transcriptional terminator comprises or consists of the sequence shown in SEQ ID NO: 83 or 86. In some examples, the transgene further includes a ptrA sequence, for example downstream of the trpC transcriptional terminator sequence. As an alternative to ptrA, the bleomycin gene or bar gene can be used. In one example, the ptrA sequence has at least 80%, at least 85%, at least 90%, at least 95%, at least 97%, at least 98%, or at least 99% sequence identity to SEQ ID NO: 89. In one example, the ptrA sequence comprises or consists of the sequence shown in SEQ ID NO: 89

In one example, the transgene comprises a sequence having at least 80%, at least 85%, at least 90%, at least 95%, at least 97%, at least 98%, or at least 99% sequence identity to SEQ ID NO: 59, 62, 65, 68, 71, and/or 74. In one example, the transgene comprises or consists of the sequence shown in SEQ ID NO: 59, 62, 65, 68, 71, and/or 74.

In one example, the transgene comprises a sequence having at least 80%, at least 85%, at least 90%, at least 95%, at least 97%, at least 98%, or at least 99% sequence identity to SEQ ID NO: 77, 80, and/or 83. In one example, the transgene comprises or consists of the sequence shown in SEQ ID NO: 77, 80, and/or 83.

In one example, the transgene comprises a sequence having at least 80%, at least 85%, at least 90%, at least 95%, at least 97%, at least 98%, or at least 99% sequence identity to SEQ ID NO: 86, 89, and/or 92. In one example, the transgene comprises or consists of the sequence shown in SEQ ID NO: 86, 89, and/or 92.

In one example, the transgene comprises a sequence having at least 80%, at least 85%, at least 90%, at least 95%, at least 97%, at least 98%, or at least 99% sequence identity to SEQ ID NO: 89 and/or 92. In one example, the transgene comprises or consists of the sequence shown in SEQ ID NO: 89 and/or 92.

In one example, the transgene comprises a sequence having at least 80%, at least 85%, at least 90%, at least 95%, at least 97%, at least 98%, or at least 99% sequence identity to SEQ ID NO: 95 and/or 97. In one example, the transgene comprises or consists of the sequence shown in SEQ ID NO: 95 and/or 97.

In one example, the transgene comprises a sequence having at least 80%, at least 85%, at least 90%, at least 95%, at least 97%, at least 98%, or at least 99% sequence identity to SEQ ID NO: 59, 62, 65, 68, 71, 74, 77, 80, 83, 86, 89, and/or 92. In one example, the transgene comprises or consists of the sequence shown in SEQ ID NO: 59, 62, 65, 68, 71, 74, 77, 80, 83, 86, 89, and/or 92.

In one example, the transgene comprises a sequence having at least 80%, at least 85%, at least 90%, at least 95%, at least 97%, at least 98%, or at least 99% sequence identity to SEQ ID NO: 59, 62, 65, 68, 71, 74, 77, 80, 83, 89, and/or 92. In one example, the transgene comprises or consists of the sequence shown in SEQ ID NO: 59, 62, 65, 68, 71, 74, 77, 80, 83, 89, and/or 92.

G. Measuring Gene Expression

A ΔcadA fungus expressing panD, BAPAT, and/or HPDH can be identified using known methods. For example, PCR and nucleic acid hybridization techniques, such as Northern, RT-PCR, and Southern analysis, can be used to confirm that a fungus expresses panD, BAPAT, and/or HPDH such as an increase in the panD, BAPAT, and/or HPDH copy number. Immunohisto-chemical and biochemical techniques can also be used to determine if a cell expresses panD, BAPAT, and/or HPDH by detecting the expression of the panD, BAPAT, and/or HPDH peptide encoded by panD, BAPAT, and/or HPDH. For example, an antibody having specificity for panD, BAPAT, and/or HPDH can be used to determine whether or not a particular fungus has increased panD, BAPAT, and/or HPDH protein expression, respectively. Further, biochemical techniques can be used to determine if a cell has increased panD, BAPAT, and/or HPDH expression by detecting a product produced as a result of the expression of the peptide. For example, production of 3-HP by ΔcadA *A. terreus* or *A. pseudoterreus* can indicate that such a fungus expresses panD, BAPAT, and HPDH.

H. Measuring 3-HP Production

Methods of determining whether a genetic inactivation of cadA in combination with expression of panD, BAPAT, and HPDH in *Aspergillus* increases 3-HP production, for example relative to the same strain with a native cadA sequence, (such as a parental strain) include HPLC.

Methods of Producing Aconitic Acid

The recombinant ΔcadA fungi can be used to produce aconitic acid (for example for as a building block for other materials, such as polymers). Such fungi can be from any *Aspergillus* species, such as *Aspergillus terreus* or *pseudoterreus*. For example, the disclosure provides methods of making aconitic acid (such as cis-aconitic acid, trans-aconitic acid, or both), which can include culturing ΔcadA fungi under conditions that permit the fungus to make aconitic acid, for example in Riscaldati medium.

In some examples, the fungi are cultured at room temperature (e.g., 20-35° C.) at normal atmospheric pressure (e.g., 1 atm). In some examples, the method includes purifying or isolating the aconitic acid, for example from the culture media or from the cultured fungus. In some examples, the aconitic acid is isolated at least 2 days, at least 3 days, at least 5 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Methods of making aconitic acid include culturing ΔcadA fungi under conditions that permit the fungus to make aconitic acid. In general, the culture media and/or culture conditions can be such that the fungi grow to an adequate density and produce aconitic acid efficiently. In one example the ΔcadA fungi are cultured or grown in an acidic liquid medium, such as Riscaldati medium (100 g Glucose, 0.11 g $KH_2PO_4$, 2.36 g $(NH_4)_2SO_4$, 2.08 g $MgSO_4*7H_2O$, 0.074 g NaCl, 0.13 g $CaCl_2*2H_2O$, 1 ml of 1000× trace elements in 1000 ml DI water, adjust pH to 3.4 with $H_2SO_4$, 1000× trace elements contains 1.3 g/L $ZnSO_4*7H_2O$, 5.5 g/L $FeSO_4*7H_2O$, 0.2 g/L $CuSO_4*5H_2O$, 0.7 g/L $MnCl_2*4H_2O$). In one example the ΔcadA fungi are cultured or grown in a liquid medium having an initial pH of less than 4, such as less than 3.5, for example about pH 3 to 4, 3.5 to 4, 3.3 to 3.5, for example pH 2.8, 2.9, 3, 3.1, 3.2, 3.3, 3.4, 3.5, 3.6, 3.7, 3.8, 3.9 or 4. In some examples the ΔcadA fungi are cultured or grown in a liquid Riscaldati medium at about 20 to 35° C. (such as 20° C. to 30° C., 25° C. to 30° C., 28 to 32° C., or 30° C.) with rotation (such as at least 100 rpm, at least 120 rpm, such as 150 rpm) at normal pressure.

In one example, the fungi are grown in culture containers (such as baffled flasks, and in some examples are silanized (5% solution of dichlorodimethylsilane in heptane (Sigma, St. Louis, Mo.)). Each culture container is inoculated with spores (such as at least $10^6$ spores/ml [agree?]) and incubated for at least 3 days, at least 4 days, at least 5 days, or at least 10 days at 30° C. and 100 to 200 rpm to obtain aconitic acid.

In one example, the ΔcadA fungi produce more aconitic acid than a corresponding fungus with wild-type cadA. In specific examples, the ΔcadA fungi produce at least 1 g/l of total aconitic acid after 4 days, for example at least 2 g/l, at least 3 g/l, at least 4 g/l, at least 5 g/l, at least 6 g/l, at least 7 g/l, at least 8 g/l, at least 9 g/l or at least 10 g/l after at least 5 days, at least 6 days, at least 7 days, at least 8 days, or at least 10 days, such as after 4 to 6 days, 8 to 10 days, or 4 to 5 days) when grown in Riscaldati medium at 30° C. with 150 rpm shaking. In specific examples, the ΔcadA fungi produce at least 1 g/l of cis-aconitic acid after 4 days, for example at least 2 g/l after at least 5 days, at least 6 days, at least 7 days, at least 8 days, or at least 10 days, such as after 4 to 6 days, 8 to 10 days, or 4 to 5 days when grown in Riscaldati medium at 30° C. with 150 rpm shaking. In specific examples, the ΔcadA fungi produce at least 1 g/l of trans-aconitic acid after 6 days, for example at least 2 g/l, at least 3 g/l, at least 4 g/l, at least 5 g/l, at least 6 g/l, at least 7 g/l, at least 8 g/l, at least 9 g/l or at least 10 g/l after at least 7 days, at least 8 days, or at least 10 days, such as after 6 to 12 days, 5 to 10 days, or 6 to 10 days) when grown in Riscaldati medium at 30° C. with 150 rpm shaking.

In some examples, the method further includes isolating the aconitic acid made by the ΔcadA fungi. Once produced, any method can be used to isolate the aconitic acid. For example, separation techniques (such as filtration) can be used to remove the fungal biomass from the culture medium, and isolation procedures (e.g., filtration, distillation, precipitation, electrodialysis, and ion-exchange procedures) can be used to obtain the aconitic acid from the broth (such as a fungi-free broth). In addition, the aconitic acid can be isolated from the culture medium after the aconitic acid production phase has been terminated.

Methods of Producing 3-HP

The recombinant ΔcadA fungi that also express panD, BAPAT, and HPDH can be used to produce 3-HP

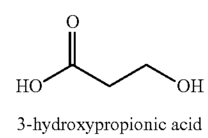

3-hydroxypropionic acid (for example for as a building block for other materials, such as acrylonitrile, acrylic acid by dehydration, malonic acid by oxidation, esters by esterification reactions with alcohols, and reduction to 1,3 propanediol). Such fungi can be from any *Aspergillus* species, such as *Aspergillus terreus* or *pseudoterreus*. For example, the disclosure provides methods of making 3-HP, which can include culturing ΔcadA fungi that also express panD, BAPAT, and HPDH under conditions that permit the fungus to make 3-HP, for example in Riscaldati medium (such as modified Riscaldati medium with 20× trace elements).

In some examples, the ΔcadA fungi that also express panD, BAPAT, and HPDH are cultured at room temperature (e.g., 20-35° C.) at normal atmospheric pressure (e.g., 1 atm). In some examples, the method includes purifying or isolating the 3-HP, for example from the culture media or from the cultured fungus. In some examples, the 3-HP is isolated at least 2 days, at least 3 days, at least 5 days, at least 7 days, at least 8 days or at least 10 days after the start of culturing, such as 2, 3, 4, 5, 6, 7, 8, 9, 10, 11, 12, 13, 14, 15, 16, 17, 18, 19 or 20 days after the start of culturing.

Methods of making 3-HP include culturing ΔcadA fungi that also express panD, BAPAT, and HPDH under conditions that permit the fungus to make 3-HP. In general, the culture media and/or culture conditions can be such that the fungi grow to an adequate density and produce 3-HP efficiently. In one example the ΔcadA fungi that also express panD, BAPAT, and HPDH are cultured or grown in an acidic liquid medium, such as Riscaldati medium (100 g Glucose, 0.11 g $KH_2PO_4$, 2.36 g $(NH_4)_2SO_4$, 2.08 g $MgSO_4*7H_2O$, 0.074 g NaCl, 0.13 g $CaCl_2*2H_2O$, 1 ml of 1000× trace elements in 1000 ml DI water, adjust pH to 3.4 with $H_2SO_4$, 1000× trace elements contains 1.3 g/L $ZnSO_4*7H_2O$, 5.5 g/L $FeSO_4*7H_2O$, 0.2 g/L $CuSO_4*5H_2O$, 0.7 g/L $MnCl_2*4H_2O$, which may include 20× trace elements). In one example the ΔcadA fungi are cultured or grown in a liquid medium having an initial pH of less than 4, such as less than 3.5, for example about pH 3 to 4, 3.5 to 4, 3.3 to 3.5, for example pH 2.8, 2.9, 3, 3.1, 3.2, 3.3, 3.4, 3.5, 3.6, 3.7, 3.8, 3.9 or 4. In some examples the ΔcadA fungi that also express panD, BAPAT, and HPDH are cultured or grown in a liquid modified Riscaldati medium with 20× trace elements at about 20 to 35° C. (such as 20° C. to 30° C., 25° C. to 30° C., 28 to 32° C., or 30° C.) with rotation (such as at least 100 rpm, at least 120 rpm, such as 150 or 200 rpm) at normal pressure.

In one example, the fungi are grown in culture containers (such as baffled flasks, and in some examples are silanized (5% solution of dichlorodimethylsilane in heptane (Sigma, St. Louis, Mo.)). Each culture container is inoculated with spores (such as at least $10^6$ spores/ml) and incubated for at least 3 days, at least 4 days, at least 5 days, or at least 10 days at 30° C. and 100 to 300 rpm (such as 150 or 200 rpm) to obtain 3-HP.

In one example, the cadA fungi that also express panD, BAPAT, and HPDH produce more 3-HP than a corresponding fungus with wild-type cadA (either with or without panD, BAPAT, and HPDH expression). In specific examples, the ΔcadA fungi that also express panD, BAPAT, and HPDH produce at least 0.1 g/l of 3-HP after at least 4 days, for example at least 0.2 g/1, at least 0.25 g/1, at least 0.3 g/1, at least 0.4 g/1, at least 0.5 g/1, at least 0.6 g/1, at least 0.7 g/1, at least 0.8 g/1, at least 0.9 g/1, at least 1.1 g/1, at least 1.2 g/1, at least 1.5 g/1, or at least 1.6 g/l after at least 5 days, at least 6 days, at least 7 days, at least 8 days, or at least 10 days, such as after 4 to 6 days, 8 to 10 days, or 4 to 5 days, when grown in Riscaldati medium (such as modified Riscaldati medium with 20× trace elements) at 30° C. with 150 rpm shaking.

In some examples, the method further includes isolating the 3-HP made by the ΔcadA fungi. Once produced, any method can be used to isolate the 3-HP. For example, separation techniques (such as filtration) can be used to remove the fungal biomass from the culture medium, and isolation procedures (e.g., filtration, distillation, precipitation, electrodialysis, and ion-exchange procedures) can be used to obtain the 3-HP from the broth (such as a fungi-free broth). In addition, the 3-HP can be isolated from the culture medium after the 3-HP production phase has been terminated.

Compositions and Kits

Also provided by the present disclosure are compositions that include isolated ΔcadA fungi (which in some examples also express panD, BAPAT, and HPDH, such as exogenous panD, BAPAT, and HPDH proteins), such as a medium for culturing, storing, or growing the fungus. In some examples, the ΔcadA fungi and ΔcadA fungi which express panD, BAPAT, and HPDH in the composition are freeze dried or lyophilized.

Also provided by the present disclosure are kits that include isolated ΔcadA fungi (which in some examples also express panD, BAPAT, and HPDH, such as exogenous panD, BAPAT, and HPDH proteins), such as a kit that includes a medium for culturing, storing, or growing the fungus. In some examples, the ΔcadA fungi and ΔcadA fungi which express panD, BAPAT, and HPDH in the kit are freeze dried or lyophilized.

Exemplary mediums include that can be in the disclosed compositions and kits include solid medium (such as those containing agar, for example complete medium (CM) or minimal medium (MM)) and liquid media (such as a fermentation broth, such as CM, MM, or CAP medium). In one example, the kit or composition includes Riscaldati medium (100 g Glucose, 0.11 g $KH_2PO_4$, 2.36 g $(NH_4)_2SO_4$, 2.08 g $MgSO_4*7H_2O$, 0.074 g NaCl, 0.13 g $CaCl_2*2H_2O$, 1 ml of 1000× trace elements in 1000 ml DI water, adjust pH to 3.4 with $H_2SO_4$, 1000× trace elements contains 1.3 g/L $ZnSO_4*7H_2O$, 5.5 g/L $FeSO_4*7H_2O$, 0.2 g/L $CuSO_4*5H_2O$, 0.7 g/L $MnCl_2*4H_2O$), for example

| | Conc. (g/L) | Amount | Notes |
|---|---|---|---|
| Glucose | 100 | 100 g | |
| $KH_2PO_4$ | 0.11 | 0.11 g | |
| $(NH_4)_2SO_4$ | 2.36 | 2.36 g | |
| $MgSO_4 * 7H_2O$ | 2.08 | 2.08 g | |
| NaCl | 0.074 | 0.074 g | |
| $CaCl_2$ * 2H2O | 0.13 | 0.13 g | |
| $ZnSO_4 * 7H_2O$ | 0.0013 | 0.0013 g | Use 1000 X soln. |
| $FeSO_4 * 7H_2O$ | 0.0055 | 0.0055 g | " |
| $CuSO_4$ * 5H2O | 0.0002 | 0.0002 g | " |
| $MnCl_2 * 4H_2O$ | 0.0007 | 0.0007 g | " |
| DI Water (L) | | 1 L | |
| Autoclave Time | 15 min for small flasks 30 min for large flasks 30-60 for fermenter | | |
| Comments: | Adjust to pH = 3.4 with $H_2SO_4$ | | |

In one example, the kit or composition includes a modified Riscaldati medium with 20× trace elements, for example 20 times of the following

| | | | |
|---|---|---|---|
| $ZnSO_4 * 7H_2O$ | 0.0013 | 0.0013 g | Use 1000 X soln. |
| $FeSO_4 * 7H_2O$ | 0.0055 | 0.0055 g | " |
| $CuSO_4$ * 5H2O | 0.0002 | 0.0002 g | " |
| $MnCl_2 * 4H_2O$ | 0.0007 | 0.0007 g | " |

Example 1

Materials and Methods

This example describes methods used in the experiments described in Examples 2-6 below.

Strains and Vector.

The parental wild type *A. pseudoterreus* strain ATCC 32359 was from ATCC. The hygromycin phosphotransferase (hph) marker cassette was amplified from vector pCB1003.

Growth Conditions.

All strains were maintained on complete medium (CM) agar and conidia of spore were harvested from cultures grown for five days on complete medium (CM) plate (10 g Glucose, 2 g Triptase peptone, 1 g yeast extract, 1 g casamino acids, 50 ml 20×$NO_3$ Salts, 1 ml of 1000×Trace elements, 1 ml of 1000× Vitamin stock, in 1000 ml DI water, pH to 6.5), 20×$NO_3$ Salts contains in g/1, $Na_2NO_3$, 120; KCL, 10.4 g; $MgSO_4.7H_2O$, 10.4 g; $KH_2PO_4$, 30.4 g. 1000× vitamin solution contains in per 100 ml $H_2O$: Biotin, 0.01 gm; pyridoxinHCL, 0.01 gm; thiamineHCl, 0.01 gm; riboflavin, 0.01 gm; paba, 0.01 gm; nicotinic acid, 0.01 gm, filtered and stock at 4° C. 1000× trace element contains in per 100 ml $H_2O$: $ZnSO_4.7H_2O$, 2.2 g; $H_3B03$, 1.1 g; $MnCl_2.4H_2O$, 0.5 g; $FeSO_4.7H_2O$, 0.5 g; $CoCl_2.6H_2O$, 0.17 g; $CuSO_4.5H_2O$, 0.16 g; $Na_2MoO_4.2H_2O$, 0.15 g; $Na_2EDTA$, 5 g, add the compounds in order, boil and cool to 60° C. Adjust pH to 6.5 with KOH. Cool to room temperature. Adjust volume to 100 ml with distilled water.

The transformants were selected for hygromycin resistance on minimum media (MM) (10 g Glucose, 50 ml 20×$NO_3$ Salts, 1 ml of 1000×Trace elements, 1 ml of 1000× Vitamin stock, 1000 ml DI water, pH to 6.25-6.5, hygromycin 100 ug/ml). $0.5\times10^8$ conidia were inoculated into 50 ml of production media for itaconic acid production (Riscaldati medium) as described previously (100 g Glucose, 0.11 g $KH_2PO_4$, 2.36 g $(NH_4)_2SO_4$, 2.08 g $MgSO_4.7H_2O$, 0.074 g NaCl, 0.13 g $CaCl_2.2H_2O$, 1 ml of 1000× trace elements in 1000 ml DI water, adjust pH to 3.4 with $H_2SO_4$, 1000× trace elements contains 1.3 g/L $ZnSO_4.7H_2O$, 5.5 g/L $FeSO_4.7H_2O$, 0.2 g/L $CuSO_4.5H_2O$, 0.7 g/L $MnCl_2.4H_2O$). Cultivation was performed at 30° C. on a rotary shaker at 150 rpm. At intervals during the incubation period, three single flasks were harvested for HPLC analysis, biomass measurement and RNA extraction. All experiments were replicated three times, and the standard deviation of the itaconic acid concentrations or dry weight was always less than 10% of the mean. For collecting samples for EST analysis, *A. pseudoterreus* was grown in 20 liter stirred tank bioreactor.

Construction of Deletion Mutants.

The deletion mutants were constructed by homologous double crossover with fusion PCR products. Synthetic oligos used for each construct are described in Table 1. Oligonucleotides were from IDT (Coraville, Iowa). Ex Taq polymerase (TaKaRa, Japan) was used to generate DNA constructs for making gene knockouts. Briefly, the 5' flanking region (~1.5 kb) of the target gene was amplified by primer pair F1 and R3. The 3' flanking region (~1.5 kb) of the target genes was amplified by primer pair F4 and R6. R3 and F4 carried 20-25 bases complementary to 5' and 3' ends of the hph cassette, respectively. The hph marker cassette was amplified from pCB1003 with the hphF and hphR primers that carried 30 bases complementary to the 3' end of the 5' flanking region and the 5' of the 3' flanking region, respectively. The three fragments, including the 5' flanking region, the hph marker cassette and the 3' flanking region were mixed in 1:3:1 molar ratio and combined by overlap PCR during the second round PCR. In the third round of PCR, the fusion PCR product was amplified with a nested primer pair (F2 and R5). This final PCR product carried a hygromycin marker cassette flanked by sequences homologous to the upstream and downstream regions of the target gene. 1-2 ug of the final product was used to transform strain *A. pseudoterreus* strain ATCC 32359.

TABLE 1

Primers for making deletion constructs

| gene targeted | primer name | primer sequence (SEQ ID NO) |
|---|---|---|
| tf | at tff1 | gagccatagccatgcaagcg (1) |
| | at tff2 | atagagtccttggatgagacg (2) |
| | at tfr5 | gtggatttcgaggttccttgc (3) |
| | at tfr6 | gaagtagaaccatgtggatcg (4) |
| | at hphf tfr3 | tgacctccactagctccagcactactagataggcccgtttagagagtgcc (5) |
| | at hphr tff4 | aatagagtagatgccgaccggccgcttcgacgacagctctgcactctcc (6) |
| | at tfr3hphf | ggcactctctaaacgggcctatctagtagtgctggagctagtggaggtca (7) |
| | at tftff4hphr | ggagagtgcagagctgtcgtcgaagcggccggtcggcatctactctatt (8) |
| mttA | at motf1 | gctgcatactcggattacgc (9) |
| | at motf2 | Gaaaaggtactcggagtacg (10) |
| | at motr5 | cagaccaaggagctttcctg (11) |
| | at motr6 | cattaagccacaggcttgcg (12) |
| | athphfmotr3 | tgacctccactagctccagcaatatggatgctgttcgttcgccgtgctgg (13) |
| | athphrmotf4 | aatagagtagatgccgaccgtgacgaggatgtgctgagtccaaacaaagc (14) |
| | at motr3hphf | ccagcacggcgaacgaacagcatccatattgctggagctagtggaggtca (15) |
| | at motf4hphr | gctttgtttggactcagcacatcctcgtcacggtcggcatctactctatt (16) |
| cadA | at cadf1 | ctccagtaacagaaccgacc (17) |
| | at cadf2 | gaacttcactgccgcattgg (18) |
| | at cadr5 | ggacactccaagaggataagg (19) |
| | at cadr6 | gctcatcacattgtttgccg (20) |
| | at hphfcadr3 | tgacctccactagctccagcggtcaatttaagaggacgatcttcgctgcg (21) |
| | at hphrcadf4 | Aatagagtagatgccgaccgtcagcctggacaggctcaccgacattagcc (22) |
| | at cadr3hphf | cgcagcgaagatcgtcctcttaaattgaccgctggagctagtggaggtca (23) |
| | at cadf4hphr | ggctaatgtcggtgagcctgtccaggctgacggtcggcatctactctatt (24) |

TABLE 1-continued

| Primers for making deletion constructs | | |
|---|---|---|
| gene targeted | primer name | primer sequence (SEQ ID NO) |
| mfsA | mfsf1 | tgatgagctgaattcgttgc (25) |
| | mfsf2 | tatagccagcttttgctgtg (26) |
| | mfsr5 | catagcgttcagagtgttg (27) |
| | mfsr6 | ccatttcaatgctttgtgcg (28) |
| | mfsr3hphf | ccataccacccttaccctcttggagtgtccgctggagctagtggaggtca (29) |
| | mfsf4hphr | gctgtggcctcctggcgattacgcaatattcggtcggcatctactctatt (30) |
| | hphfmfsr3 | tgacctccactagctccagcggacactccaagagggtaagggtggtatgg (31) |
| | hphrmfsf4 | aatagagtagatgccgaccgaatattgcgtaatcgccaggaggccacagc (32) |
| p450 | p450f1 | tctccaaatcatcgtcatcg (33) |
| | p450f2 | cttcaatcgcaccgacatcc (34) |
| | p450r5 | tcgtgtagacaagtccagtc (35) |
| | p450r6 | ctataccactctagtgatgg (36) |
| | p450r3hphf | cctctgctcaggttgttttcgaacaggagcgctggagctagtggaggtca (37) |
| | p450f4hphr | cggaatgcagataggcatcacagtccagaacggtcggcatctactctatt (38) |
| | hphfp450r3 | tgacctccactagctccagcgctcctgttcgaaaacaacctgagcagagg (39) |
| | hphrp450f4 | aatagagtagatgccgaccgttctggactgtgatgcctatctgcattccg (40) |

Transformation of *A. pseudoterreus* Protoplasts.

$10^8$ conidia of *A. pseudoterreus* ATCC 32359 were used to inoculate 300 ml Erlenmeyer baffle flasks containing 100 ml of complete media. The cultures were grown overnight (16-18 hrs) at 30° C. and 150 rpm. The mycelia were then harvested by filtering the culture through miracloth and rinsing the mycelia mat with sterile water. The protoplasts were prepared by treating mycelia (mass of approximately 1-2 beans) with 20 mg/ml lysing enzyme (L1412, Sigma) dissolved in 20 ml of osmotic wash buffer (0.5M KCl, 10 mM sodium phosphate, pH 5.8) for 2 h. Protoplasts were collected by filtering protoplasts through sterile miracloth into a 50 ml screw cap centrifuge tube and centrifuging at 1000×g for 10 min at 4° C. Protoplasts were then washed twice with 20 ml Washing Solution (0.6M KCl, 0.1M Tris/HCl, pH 7.0) and once in 10 ml Conditioning Solution (0.6M KCl, 50 mM $CaCl_2$, 10 mM Tris/HCl, pH 7.5). For transformation, 1-2 ug DNA was added to $2\times10^7$ protoplasts in 0.1 ml Conditioning Solution. A control reaction without added DNA was performed at the same time. 25 μl of PEG solution (25% PEG8000, 0.6M KCl, 50 mM $CaCl_2$, 10 mM Tris/HCl, and pH 7.5) was added and the protoplasts were incubated for 20 min on ice. An additional 500 ul of the PEG was added using a wide bore pipette tip and carefully mixed with the protoplasts by gently pipetting up and down 1-2 times. The protoplast solution was then incubated for 5 min on ice. 1 ml of cold Conditioning Solution was added and mixed by gently inverting the tube several times. Then the protoplast suspension was mixed with 12 ml of 50° C. selection agar (Minimal media+0.6M KCl+1.5% Agar+100 ug/ml hygromycin) contained in a 15 ml screwcap centrifuge tube. The tubes were then mixed by inverting the tubes 3-4 times and poured directly onto the petri dish plates. The control reaction was divided into a positive control plate (no selection antibiotics in the top agar and bottom plates) and a negative control (with selection hygromycin in top and bottom agar). The solidified plates were inverted and incubated overnight at 30° C. The next day, the plates were then overlaid with 15 ml of Minimal Medium (MM) containing 150 ug/ml hygromycin. Colonies should start to appear after 3-4 days. The transformants were excised and transferred to MM plate containing 100 ug/ml hygromycin. Correct transformants on the hygromycin plate were confirmed by PCR approaches and southern blot.

Dry Mass Measurement.

Dry mass at each time point was determined by harvesting the mycelium on miracloth by suction filtration and washed twice with 50 ml distilled water. Subsequently, the dry weight was determined by drying it overnight in pre-weighed tubes on lyophilizer.

HPLC.

The content of itaconic acid, aconitic acid, and glucose in each sample collected from filtration (0.22 um) was assayed by a high-pressure liquid chromatography (HPLC) on a Bio-Rad Aminex HPX-87H ion exclusion column (300 mm×7.8 mm). Columns were eluted with Sulfuric acid (0.005 M) at a flow rate of 0.55 mL/min. The sample volume was 10-100 ul, and IA was detected at 210 nm with a Waters 2414 refractive index detector.

RNA Isolation and Transcript Analysis by Quantitative Real Time RT-PCR.

Wild type and tf deletion strains were grown in Riscaldati medium at 30° C. After 3 days growth, mycelia were harvested, pressed dry between paper towels and immediately flash frozen in liquid nitrogen. The entire sample was then ground in a mortar and pestle with liquid nitrogen. Approximately 100 mg samples (about 0.1 ml) were extracted using Trizol® reagent (Chomczynski, *BioTechniques* 1993, 15(3):532-534, 536-537) and the resulting RNA was converted to cDNA using high capacity RNA-to-DNA kit (Applied Biosystems). Quantitative RT-PCR were performed in 50 ul reactions containing 25 ul of Power SYBR green PCR master mix (Applied Biosystems), 50 ng cDNA (from 50 ng RNA) and 0.2 uM forward and reverse primers. The RT-PCR primers used for analysis of the mttA, cadA, mfsA genes and benA (β-tubulin) as endogenous control gene are listed in Table 3. There are two additional controls, one is a no RT (without adding RT enzyme mix) control to estimate contamination from genomic DNA, and the other is no-template controls for each primer pair to measure effect from primer dimer formation. Amplification was performed using 7900HT Fast Real-Time PCR system (Applied Biosystems) programmed to initially hold at 95° C. for 10 min and then to complete 45 cycles of 95° C. for 15 s, 60° C., for 60 s. The data were analyzed using the comparative $C_T$ method (e.g., see Schmittgen et al., *Analytical biochemistry* 2000, 285(2):194-204)

Example 2

Expression Profile of Itaconic Acid Gene Cluster in *A. pseudoterreus*

Figure 2:
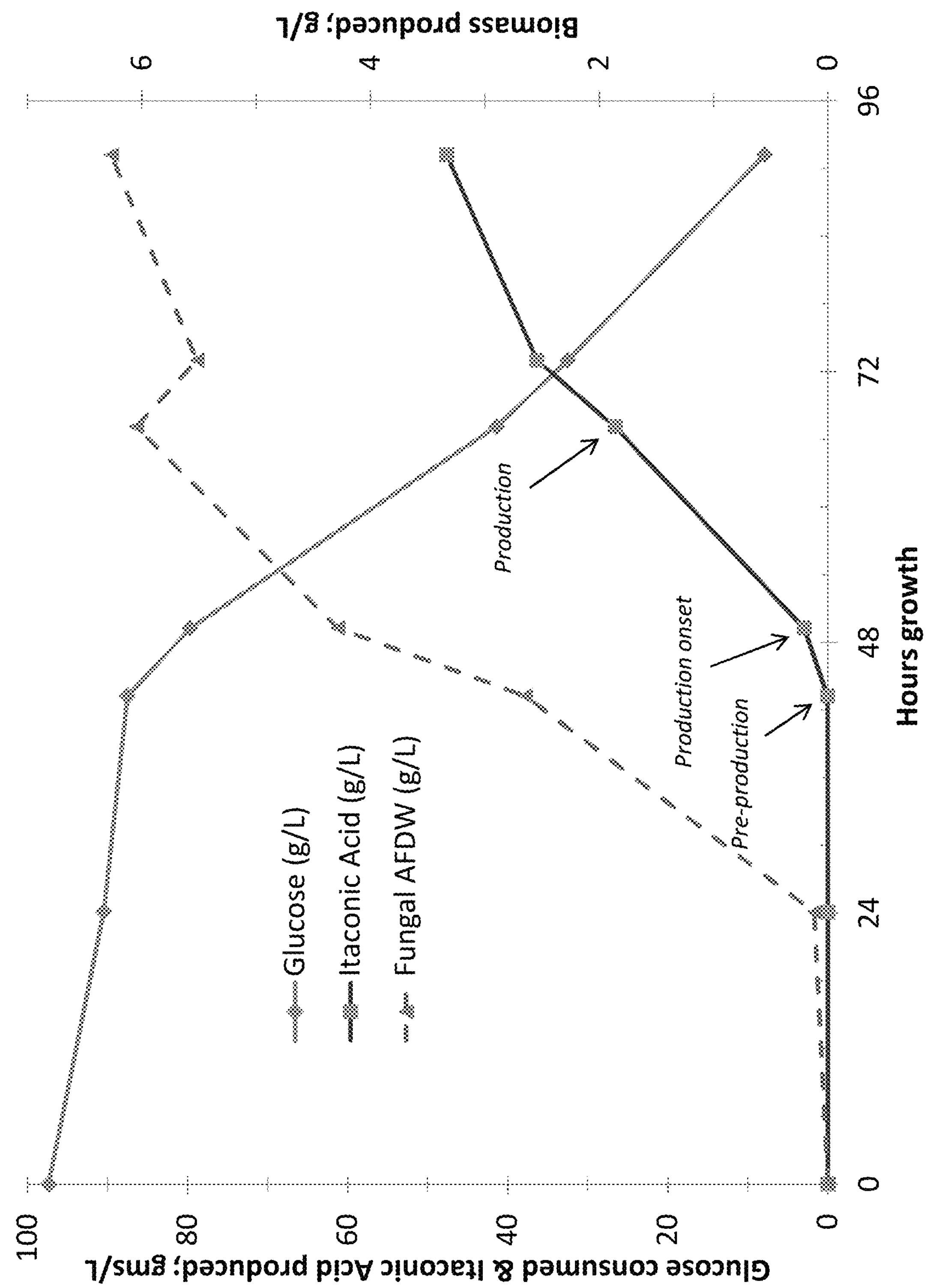
FIG. 2. *Aspergillus pseudoterreus* ATCC 32359 fermentation data for collecting samples for EST sequencing. A 20 L volume of Riscaldati production medium (see Riscaldati et al., *J Biotechnol* 2000, 83:219-230) in a 30 L working volume Sartorius fermenter was inoculated with $10^6$ *A. pseudoterreus* spores per ml. The three samples referred to as "preproduction, production onset and production" were collected at 40, 50 and 62 hours, respectively. Itaconic acid and glucose data are shown on the left y-axis and fungal ash free dry weight (AFDW) is shown on the right y-axis.

RNA samples were prepared from three different growth stages of *A. pseudoterreus* in the itaconic acid production process. The stages were 1) "pre-production," before itaconic acid production begins, 2) "production onset," the beginning of itaconic acid production correlated with phosphate depletion, and 3) "production," early in the phase of maximum itaconic acid production rate (FIG. 2). EST data revealed four genes in the cluster having high expression frequency both in the onset phase and production phase, but not in the pre-production phase (Table 2). These genes were tf, mttA, cadA, and mfsA.

TABLE 2

Number of ESTs per gene at three stages of itaconic acid production

| Broad Institute Gene No. | Gene Description | Pre-Production | Production Onset | Production |
|---|---|---|---|---|
| ATEG_09968.1 | upstream flanking gene; lovE | 0 | 0 | 0 |
| ATEG_09969.1 | tf | 0 | 4 | 4 |
| ATEG_09970.1 | mttA | 0 | 81 | 93 |
| ATEG_09971.1 | cadA | 0 | 77 | 110 |
| ATEG_09972.1 | mfsA | 0 | 6 | 7 |
| ATEG_09973.1 | p450 | 0 | 7 | 11 |
| ATEG_09974.1 | downstream flanking gene | 0 | 0 | 0 |
| ATEG_09817.1 | control; gapdh | 31 | 51 | 43 |

cadA has 77 ESTs at the beginning of itaconic acid (IA) production and 110 ESTs during the IA production, while mttA has 81 and 93 ESTs respectively in each stage. Both have no transcript detected before IA is produced. Transcription factor (tf) and mfsA, like cadA and mttA, did not show any expression before IA production, but had significant levels of transcription following the initiation of itaconic acid production (Table 2).

When genes upstream and downstream of tf, cadA, mttA and mfsA were examined, a similar expression pattern was not observed. No transcript was detected for either upstream or downstream genes in any stage of IA production except for p450. Control gene gpdh, which is far away from this region, showed high expression through the whole growth stage. This EST data clearly demonstrated that four genes tf, cadA, mttA and mfsA have the same expression pattern and are closely related to the IA production process. In addition, these four genes are in the same cluster. They are turned on strongly at the onset of IA production and persists through the production phase (FIG. 2).

Example 3

Effect of Tf, cadA, mttA and mfsA Deletion on Itaconic Acid Production in *A. pseudoterreus*

A transformation system was developed to allow for transformation of *A. pseudoterreus* (see Example 1). This system was used to generate recombinant knockout strains for each of the endogenous tf, cadA, mttA and mfsA genes. The KO mutant strains were confirmed by PCR and southern blot. The transformation protocol gave very high frequency of homologous deletion, 8 out 10 had the correct deletion. This high deletion frequency may be due to the presence of a ku gene mutation in the genome of wild-type *A. pseudoterreus.*

Biomass accumulation and itaconic acid (IA) production of each of the four knockout mutants and wild type *A. pseudoterreus* were measured at day 5. All strains, including wild type, had similar biomass accumulation (FIG. 3A). There is no significant difference in biomass among these five strains, indicating that deletion of these genes does not cause a noticeable growth defect.

However, the yield of IA was significantly lower in all four deletion strains (Δtf, ΔcadA, ΔmttA and ΔmfsAΔ) when compared to wild type *A. pseudoterreus*. After 5 days growth in the Riscaldati medium, the Δtf strain had only generated ~3 g/l IA, compared to the wild type strain, which generated ~24 g/l of IA (about an 8-fold decrease). No detectable IA was produced by the ΔcadA and ΔmttA strains. ΔmfsA produced around 16 g/L itaconic acid, about ⅔ of wild type *A. pseudoterreus.*

These observations demonstrate that tf, mttA, cadA and mfsA genes play a role in itaconic acid production.

Example 4

Production Kinetics of Itaconic Acid in Wild Type and Tf Deletion Strain

To test the production kinetics in the deletion strains, Δtf and wild type *A. pseudoterreus* strain ATCC 32359 were tested for IA production during the growth on a rotary shaker for 7 days. IA was analyzed by HPLC for 2, 4, 6 and 7 day cultures.

Figure 4:
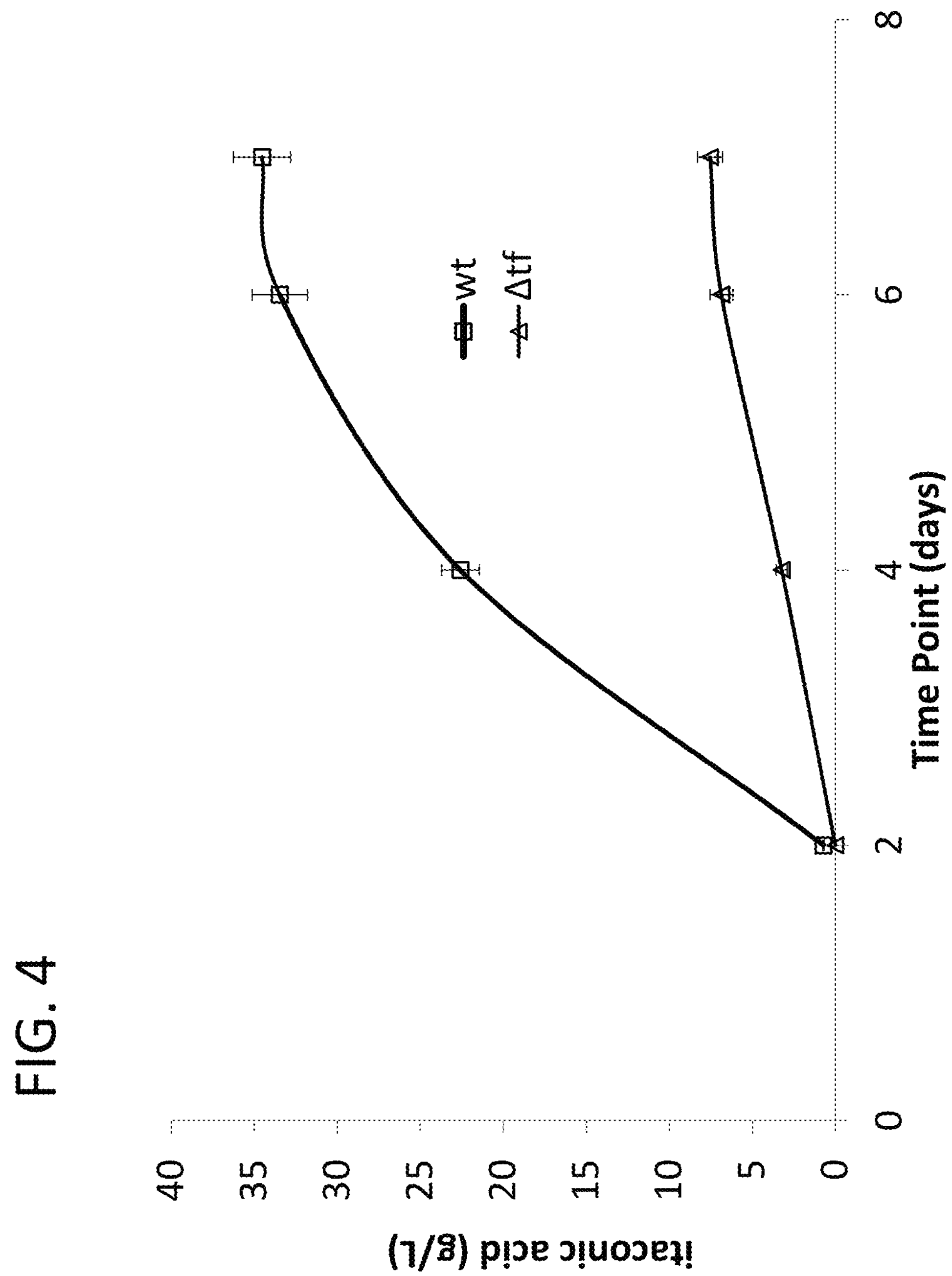
FIG. 4. Kinetics of itaconic acid production by wild type *A. pseudoterreus* and Δtf strains grown in production media at 30° C. Spores $0.5\times10^8$ were inoculated into 50 ml of production media for itaconic acid production as described in Riscaldati et al. (J Biotechnol 2000, 83:219-230). The cultivation was performed at 30° C. on a rotary shaker at 150 rpm. All experiments were done in three replicates. At day 2, 4, 6, and 7, HPLC analysis was performed to determine amount of IA produced. Each sample was measured in five replicates. Error bars represent standard deviation from the means.

As shown in FIG. 4, the IA yield plateaued at day 7 in both Δtf and wild type strains. Interestingly, the IA yield in Δtf (50) is much lower than that of wild type (35 g/1), a decrease of about 7-fold. Thus, the Δtf strain produces IA at slower rate with a lower maximum IA yield than the wild type strain.

Example 5

Tf Regulation

The effects of tf gene deletion on the transcription level of other genes in the cluster were investigated by real-time reverse transcription PCR (RT-PCR). In the both Δtf and wild type strains, expression level of each gene was analyzed by RT-PCR by measuring mttA, cadA, mfsA mRNA levels using primers specific for those genes (Table 3).

TABLE 3 primers for real-time RT-PCR analysis of cluster gene transcript level

| Gene targeted | Primer name | Primer sequence (SEQ ID NO:) |
|---|---|---|
| mttA | mttF | Gctttcaatgtggttcctac (41) |
| | mttR | ctccatcacctaccctttc (42) |
| cadA | cadF | gaagtgtgggatctggc (43) |
| | cadR | gggttcggtatttgtgaag (44) |
| mfsA | mfsF | caagaacagtttggcctgag (45) |
| | mfsR | gcggacatcatacaatctgg (46) |
| benA | β-tubulinF | ttgtcgatgttgttcgtcgc (47) |
| | β-tubulinR | tggcgttgtaaggctcaacc (48) |

Figure 5:
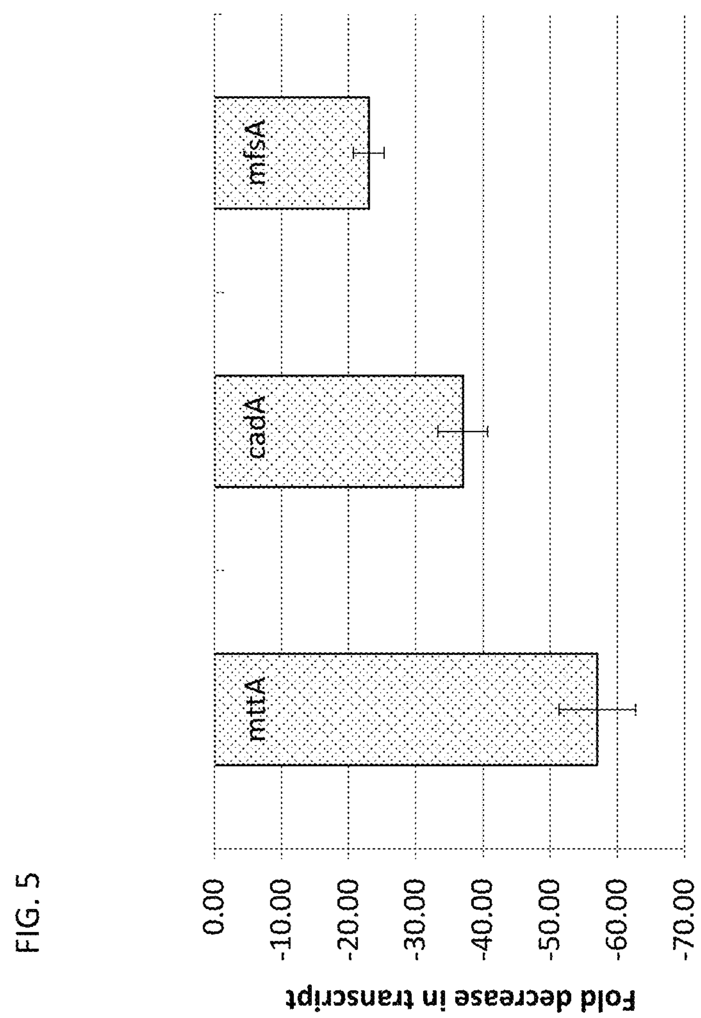
FIG. 5. Real-time (RT)-PCR analysis of the relative levels of mttA, cadA, mfsA mRNAs in wild type and Δtf strains. Spores $0.5\times10^8$ were inoculated into 50 ml of production media for itaconic acid production as described in Riscaldati et al. (*J Biotechnol* 2000, 83:219-230). The cultivation was performed at 30° C. on a rotary shaker at 150 rpm. All experiments were done in three biological replicates. At day 3, samples were collected and RNA was extracted for RT-PCR. The average of results obtained from five independent RNA preparations is shown. All transcript levels were measured in triplicate for each RNA preparation. Error bars represent standard deviations from the means. Compared to wild type, expression level of mttA, cadA and mfsA were decreased 57, 37 and 23 fold in the Δtf strain.

As shown in FIG. 5, in Δtf strains, mRNA level of mttA decreased 57 fold, cadA mRNA level decreased 37 fold, and mfsA decreased 23 fold, as compared to their expression in wild type *A. pseudoterreus* 32359. Thus, inactivation of the tf gene dramatically reduced the level of mRNA of other genes in the cluster. Within the itaconic acid biosynthesis cluster, the transcription factor potentially controls expression of other genes.

Example 6 cadA Deletion Creates a Novel Strain that Produces Aconitic Acid

Figure 3B:
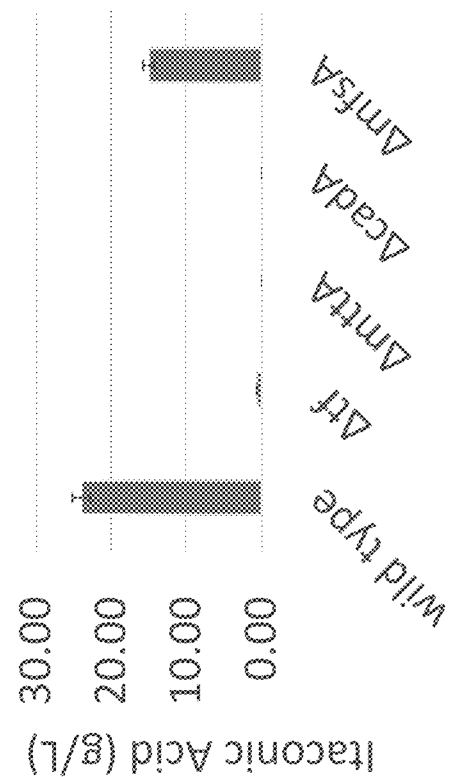
FIGS. 3A-3B. *Aspergillus pseudoterreus* IA Cluster Analysis after five days growth in Riscaldati medium. Spores $0.5\times10^8$ were inoculated into 50 ml of production media for IA production as described in Riscaldati et al. (*J Biotechnol* 2000, 83:219-230). The cultivation was performed at 30° C. on a rotary shaker at 150 rpm. At the end of five days, samples were obtained for HPLC analysis and biomass measurement. (A) Dry mass measurement of wild type and mutant strains (B) Itaconic acid production of wild type and mutant strains. The average obtained from three independent experiments are shown. Error bars represent standard deviations from the means.
Figure 3A:
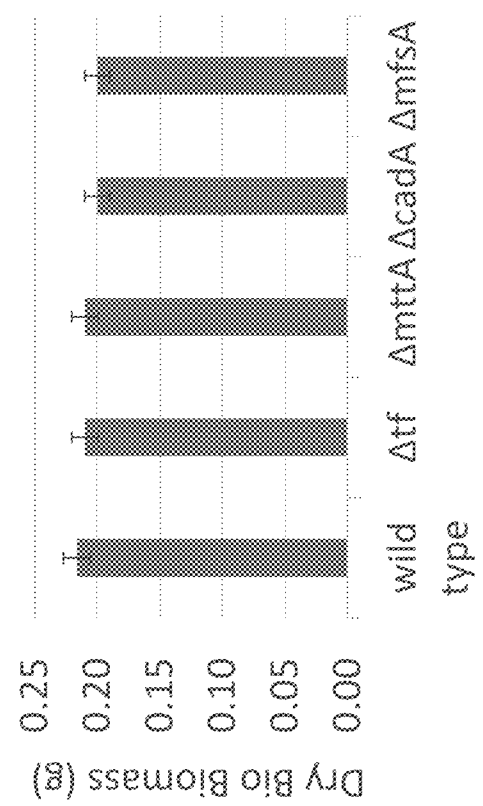
Figures 6A, 6B:
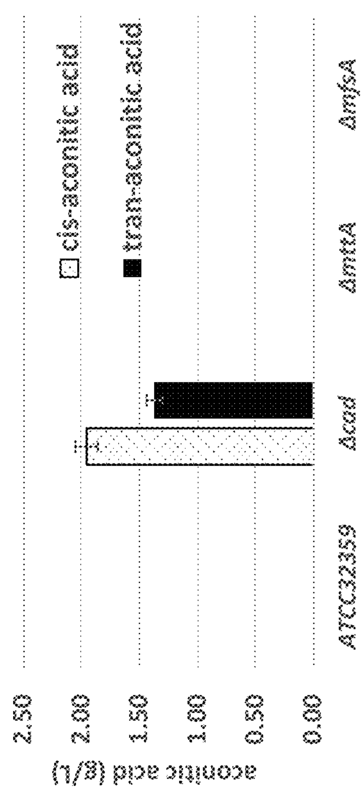
FIGS. 6A-6C. Aconitic acid production in ΔcadA strain. The cultivation was performed at 30° C. on a rotary shaker at 150 rpm. All experiments were done in three biological replicates. (A) at day 5, only ΔcadA produced cis-aconitic and trans-aconitic acid, while wild type and other mutants did not. (B) Time course of cis- and trans-aconitic acid production in Δcad strain over 10 days. (C) Comparison of total aconitic acid production between wild type and ΔcadA mutant strains.
Figure 6C:
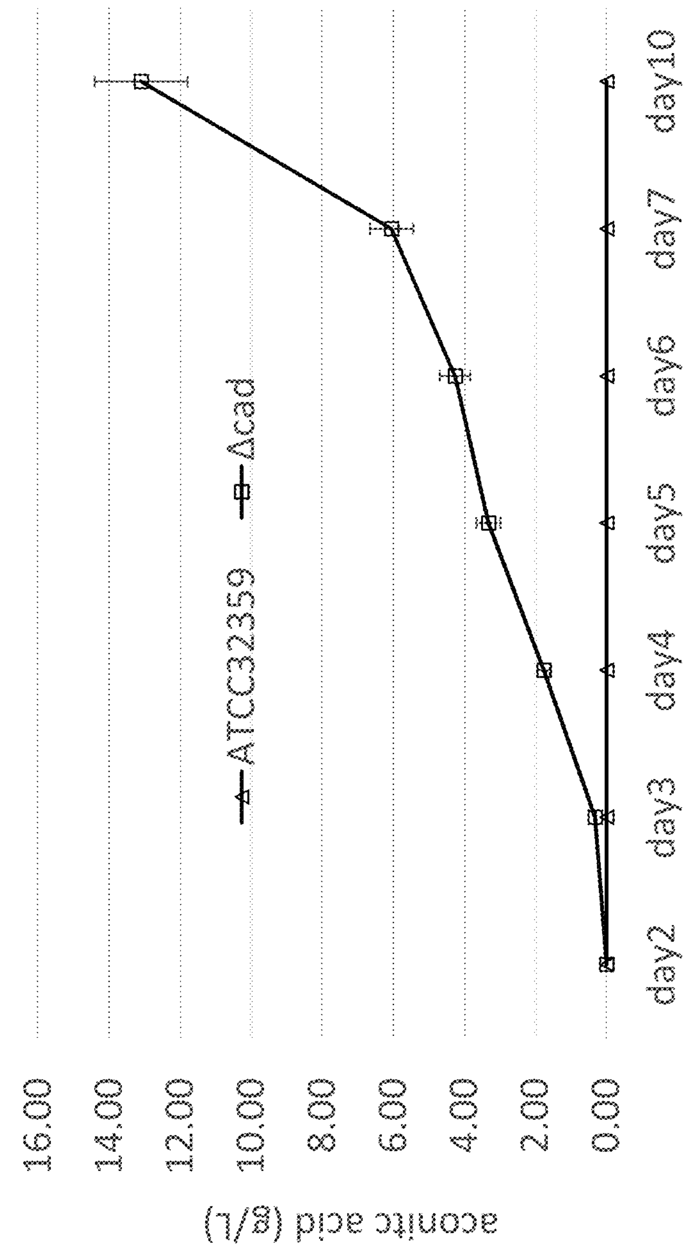

In *A. pseudoterreus*, when cadA was deleted, itaconic acid production was completely abolished (FIG. 3B). However, 3.5 g per liter aconitic acid in the ΔcadA strain was detected at day 5 (FIG. 6A). Aconitic acid was not produced by the wild type, ΔmttA or ΔmfsA strains (FIG. 6A). A time course analysis showed that aconitic acid started to appear in the supernatant at day 3, similar as IA in the wild type strain (FIG. 6B). At day 3, only cis-aconitic acid was detected in the supernatant. At day 4, both cis-aconitic acid and trans-aconitic acid were detected. From day 5 onward, cis-aconitic acid remained consistent at about 2 g/L, while trans-aconitic acid yield continued to increase (FIG. 6B). By day 10, 10 g/L trans-aconitic acid was detected in the supernatant from the ΔcadA strain (FIG. 6B). FIG. 6C shows a comparison of total aconitic acid production between wild type and ΔcadA fungi. Thus, ΔcadA stains of *A. pseudoterreus* and *A. terreus* can be used to produce cis- and trans-aconitic acid.

Example 7

Materials and Methods

This example describes methods used in the experiments described in Example 8.

Transgene Expression Vector for 3-HP Production

Isolation of DNA Fragments:

Fragment 1*: A. pseudoterreus* 5'-cadA gene, 987 bp (SEQ ID NO: 59) isolated by PCR with the oligo pair 1969 and 1970 (SEQ ID NOS: 60 and 61, respectively) and *A. pseudoterreus* genomic DNA;

Fragment 2: *A. niger* gpdA promoter, 813 bp (SEQ ID NO: 62) isolated by PCR with oligo pair of 1971 and 1972 (SEQ ID NOS: 63 and 64, respectively) and *A. niger* genomic DNA;

Fragment 3: aspartate 1-decarboxylase (panD) cDNA of *Tribolium castaneum* with codon optimization for *A. pseudoterreus,* 1617 bp (SEQ ID NO: 65) was isolated by PCR with the oligo pair of 1973 and 1974 (SEQ ID NOS: 66 and 67, respectively) and the plasmid DNA containing the synthesized panD cDNA;

Fragment 4: bidirectional terminator from *A. niger* elf3/multifunctional chaperone (SEQ ID NO: 68) was isolated by PCR with oligo pair of 1975 and 1976 (SEQ ID NOS: 69 and 70, respectively) and the genomic DNA of *A. niger;*

Fragment 5: codon optimized synthetic cDNA of β-alanine-pyruvate aminotransferase (BAPAT) of *Bacillus cereus,* 1350 bp (SEQ ID NO: 71) was isolated by PCR with oligo pair of 1977 and 1978 (SEQ ID NOS: 72 and 73, respectively) and the plasmid DNA containing the synthesized BABAT cDNA;

Fragment 6: *A. niger* enol promoter, 704 bp (SEQ ID NO: 74) isolated by PCR with oligo pair of 1979 and 1980 (SEQ ID NOS: 75 and 76, respectively) and *A. niger* genomic DNA;

Fragment 7: *A. nidulans* gpdA promoter, 885 bp (SEQ ID NO: 77) was isolated by PCR with the oligo pair of 2002 and 1982 (SEQ ID NOS: 78 and 79, respectively) and *A. nidulans* genomic DNA;

Fragment 8: the codon optimized synthetic cDNA of *E. coli* 3-hydroxypropionate dehydrogenase (HPDH), 741 bp (SEQ ID NO: 80) was isolated by PCR with oligo pair of 1983 and 1984 (SEQ ID NOS: 81 and 82, respectively) and the plasmid DNA containing the codon-optimized synthesized HPDH DNA of *E. coli;*

Fragment 9: trpC terminator of *A. nidulans,* 473 bp (SEQ ID NO: 83) isolated by PCR with oligo pair of 1985 and 2004 (SEQ ID NOS: 84 and 85, respectively) and plasmid DNA of pAN7.1;

Fragment 10: trpC terminator of *A. nidulans,* 473 bp (SEQ ID NO: 86) isolated by PCR with the oligo pair of 2005 and 1986 (SEQ ID NOS: 87 and 88, respectively) and plasmid DNA of pAN7.1;

Fragment 11: *A. oryzae* ptrA selection marker gene, 2005 bp; SEQ ID NO: 89) isolated by PCR with the oligo pair of 1987 and 1988 (SEQ ID NOS: 90 and 91, respectively) and *A. oryzae* genomic DNA;

Fragment 12*: A. pseudoterreus* 3'-cadA gene, 908 bp (SEQ ID NO: 92) isolated by PCR with the oligo pair 1989 and 2003 (SEQ ID NOS: 93 and 94, respectively) and *A. oryzae* genomic DNA;

Fragment 13 (SEQ ID NO: 95): Combination of Fragments 7 to 9 (SEQ ID NOS: 77, 80, and 83, respectively), 2099 bp isolated by PCR with oligo pair of 1981 and 1986 (SEQ ID NOS: 96 and 88, respectively) and plasmid DNA of pZD-2; and Fragment 14 (SEQ ID NO: 97): Combination of Fragments 11 to 12 (SEQ ID NOS: 89 and 92, respectively), 2913 bp was isolated by PCR with the oligo pair of 1987 and 1990 (SEQ ID NOS: 90 and 98, respectively) and plasmid DNA of pZD-3.

The oligonucleotide primers used are shown in Table 4.

TABLE 4

Primers used to generate vector for 3-HP production

| Name | Sequence (SEQ ID NO:) |
|---|---|
| 1969cad1 | ccctcgaggtcgacggtatcgata**GATATC**GGTTGTAGCA GCGTAAACAC (60) |
| 1970cad2 | tctttcatagtagCCTTGGTGAACATCTTGAGG (61) |
| 1971gpdA1 | atgttcaccaaggCTACTATGAAAGACCGCGATG (63) |
| 1972gpdA2 | cgccggtggcgggCATTGTTTAGATGTGTCTATGTG (64) |
| 1973pan1 | catctaaacaatgCCCGCCACCGGCGAGGACCA (66) |
| 1974pan2 | atccaacccatcaGAGGTCGGAGCCCAGGCGTTCG (67) |
| 1975ter1 | gggctccgacctcTGATGGGTTGGATGACGATG (69) |
| 1976ter2 | tctggcccagctcTGAGTCCTAGATGGGTGGTG (70) |
| 1977bap1 | catctaggactcaGAGCTGGGCCAGACATTCCTTC (72) |
| 1978bap2 | gtccatcaacatgGAACTGATGATCGTCCAGGTCAC (73) |
| 1979eno1 | cgatcatcagttcCATGTTGATGGACTGGAGGG (75) |
| 1980eno2 | gaactagtggatcccccgggctgc**GttaaC**TCGAGCTTAC AAGAAGTAGCC (76) |

TABLE 4-continued

| Primers used to generate vector for 3-HP production | |
|---|---|
| Name | Sequence (SEQ ID NO:) |
| 1981gpdA1 | acaggctacttcttgtaagctcgagttTCTGTACAGTGACCGGTGAC (96) |
| 1982gpdA2 | tgaccagcacgatCATGGTGATGTCTGCTCAAG (79) |
| 1983hpd1 | agacatcaccatgATCGTGCTGGTCACGGGCGC (81) |
| 1984hpd2 | gccatcggtcctaTTGGCGGTGGACGTTCAGGC (82) |
| 1985trp1 | cgtccaccgccaaTAGGACCGATGGCTGTGTAG (84) |
| 1986trp2 | cccgtctgtcagaGAGCGGATTCCTCAGTCTCG (88) |
| 1987ptrA1 | gaggaatccgctcTCTGACAGACGGGCAATTGATTAC (90) |
| 1988ptrA2 | gaatgttgctgagGAGCCGCTCTTGCATCTTTG (91) |
| 1989cad3 | gcaagagcggctcCTCAGCAACATTCGCCATGTTC (93) |
| 1990cad4 | actaaagggaacaaaagctggagctCAGCTCCACTGCTCATAGTCTTTG(98) |
| 2002gpdA5 | ccctcgaggtcgacggtatcgataGTTAACTCTGTACAGTGACCGGTGAC (78) |
| 2003cad3 | gaactagtggatcccccgggctgcaCAGCTCCACTGCTCATAGTCTTTG (94) |
| 2004trpR | gaactagtggatcccccgggctgcaGAGCGGATTCCTCAGTCTCG (85) |
| 2005trpF | ccctcgaggtcgacggtatcgataTAGGACCGATGGCTGTGTAG (87) |

Figure 7:
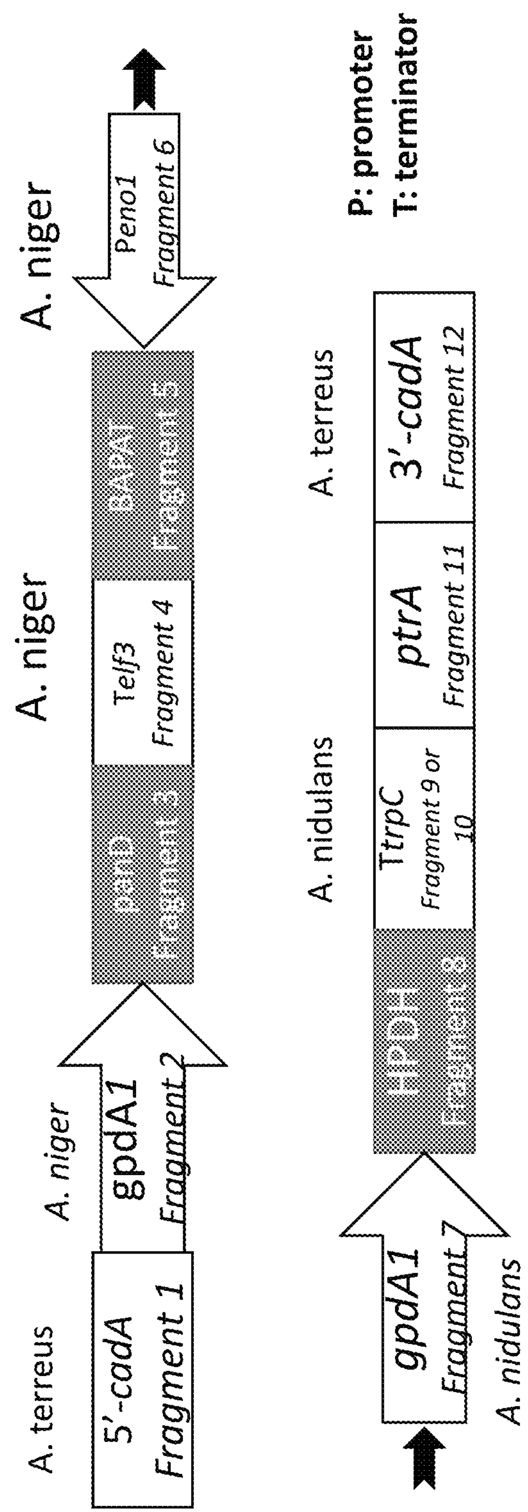
FIG. 7. Arrangement of transgene expression cassette for 3-HP Production in *A. pseudoterreus* with a synthetic beta-alanine pathway. A description of each Fragment is described in Example 8. The relevant fragments were cloned into pBlueScript SK(−) vector linearized with restriction enzyme H3/PstI. The whole expression cassette was linearized with restriction enzyme XhoI for the protoplast transformation for homologous recombination at cadA locus.

An overview of the arrangement of the Fragments is shown in FIG. 7. Fragments 1 to 6 (SEQ ID NOS: 59, 62, 65, 68, 71 and 74, respectively) were assembled into the plasmid DNA pBlueScript SK (−) linearized with HindIII and PstI via Gibson Assembly master kit to form plasmid pZD-1. A restriction enzyme site HpaI was introduced at the end of the fragment 6 for further cloning.

Fragments 7 to 9 (SEQ ID NOS: 77, 80, and 83, respectively) were assembled into the plasmid DNA pBlueScript SK (−) linearized with HindIII and PstI via Gibson Assembly master kit to form plasmid DNA pZD-2.

Fragments 10 to 12 (SEQ ID NOS: 86, 89, and 92, respectively) were assembled into the pBlueScript SK(−) vector linearized with restriction enzyme HindIII and PstI by Gibson assembly to form the plasmid vector ZD-3. (Only fragments 11 and 12 were used in the next step; SEQ ID NOS: 89 and 92).

Fragments 13 and 14 (SEQ ID NOS: 95 and 97) were assembled together into the plasmid DNA vector ZD-1 linearized with restriction enzyme HpaI/SacI via Gibson Assembly master kit to form pZD-4.

Genomic DNA isolation and Southern blotting analysis were performed as described in Example 1 (and see Dai et al., 2017*, Appl Microbiol Biotechnol* 101:6099-6110).

Detection of 3-HP

The extracellular 3-HP in the culture supernatants was quantified with HPLC method as described in Example 1.

Example 8

Production of 3-HP

The constructs generated in Example 7 (FIG. 7) were transformed into wild type *A. pseudoterreus* strain ATCC 32359 using the methods describe in Example 1, thereby inactivating/disrupting the cadA gene in some examples.

Figure 8:
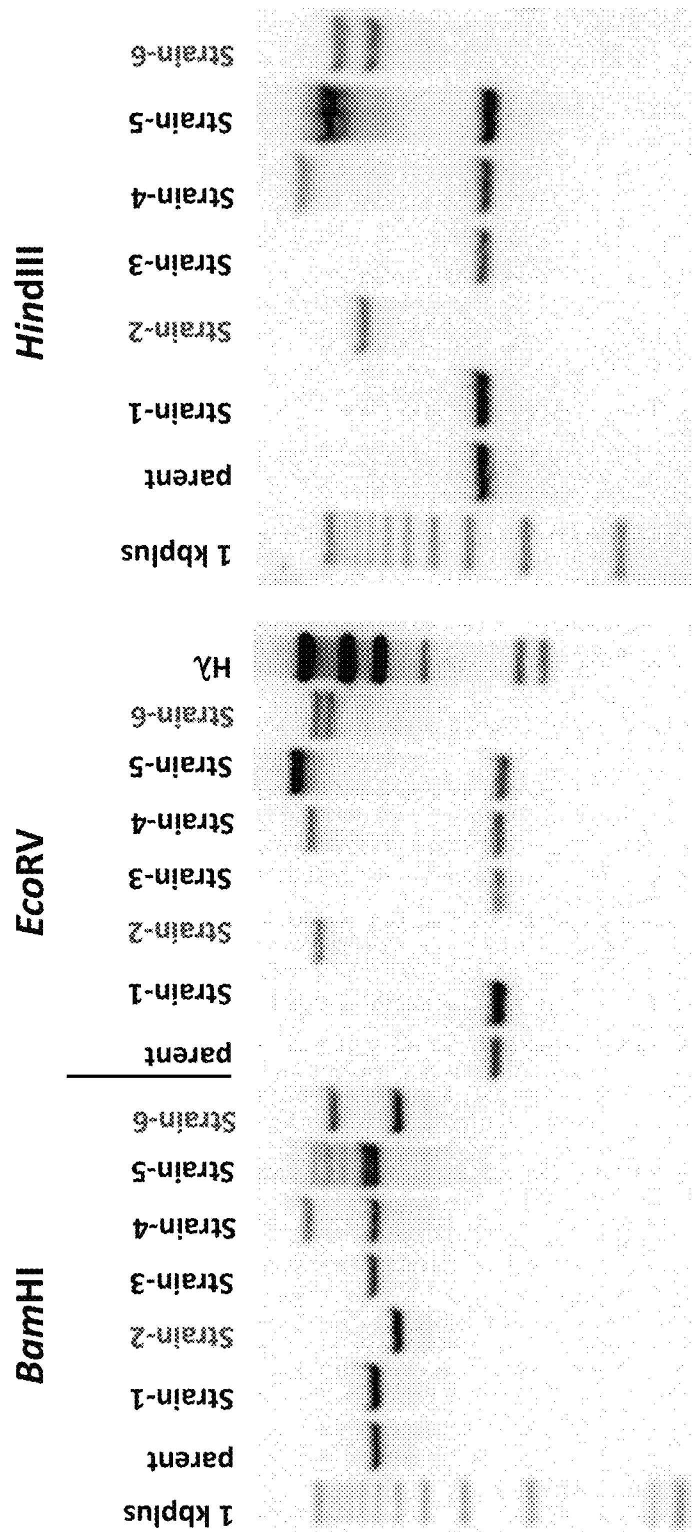
FIG. 8. Southern blot confirmation of cadA gene interruption by 3HP transgene expression cassette (FIG. 7). The cadA gene in the transgenic strains #2 (3HP-2) and #6 (3HP-6) was disrupted by the homologous recombination, while the random integration occurred in the strains #4 (3HP-4) and #5 (3HP-5). No insertion was observed in strains #1 and #3.

As shown in FIG. 8, restriction fragment length polymorphism of selected transgenic strains show that the transgene expression cassette was inserted into the cadA locus in strain-2 (with one copy) and strain-6 (two copies), while the strain-4 and strain-5 carry the transgene expression cassette with random integration. No integration of transgene expression cassette was observed in strain-1 and strain-3.

Figure 9B:
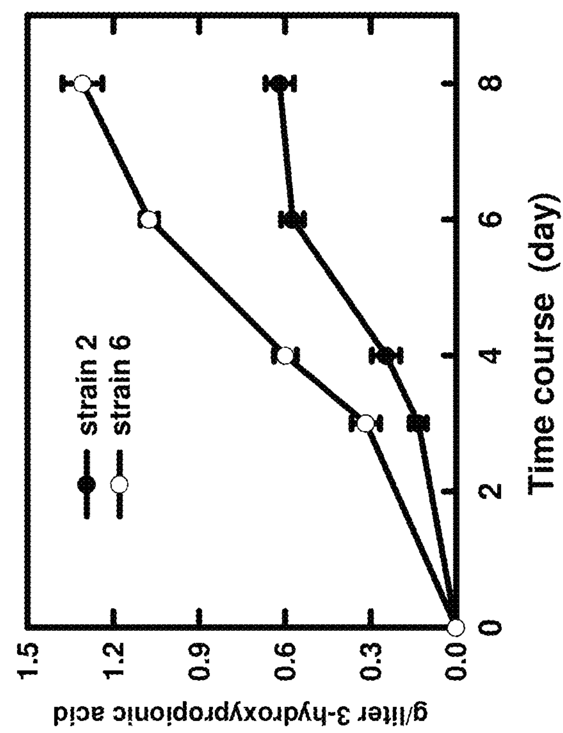
FIGS. 9A-9B. 3-HP production. *A. pseudoterreus* having a genetically inactivated cadA locus alone (cad1Δ), or additionally expressing panD, BAPAT, and HPDH (3HP-2, 3HP-4, 3HP-5, and 3-HP6), were grown at 30° C. on a rotary shaker at 200 rpm for (A) 7 days, or (B) over 8 days, in the Riscaldati media with 20× TE, and 3-HP present in the supernatant measured using HPLC.
Figure 9A:
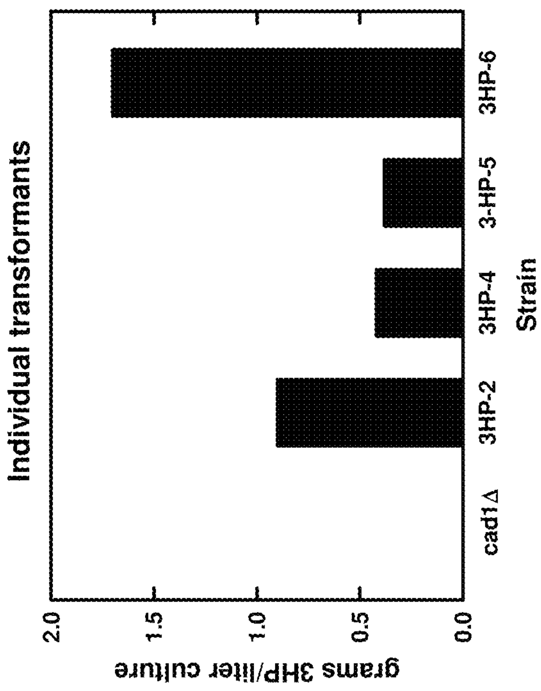

3-HP production was measured in several transformants. As shown in FIG. 9A, the ΔcadA strain did not produce 3-HP, while insertion of the transgene expression cassette that allowed for expression of panD, BAPAT, and HPDH, into the cadA locus with one copy or two copies and resulted in 0.9 or 1.7 g/13-HP accumulation in the strains 3HP-2 or 3HP-6. In contrast, when the transgene expression cassette was randomly inserted into the chromosome, 3HP production was substantially lower (Strains 3HP-4 and 3HP-5). FIG. 9B shows 3-HP production over 8 days in Strains 3HP-2 and 3HP-6 (strains 2 and 6, respectively). Thus, genetically inactivating cadA can increase 3-HP production.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. An isolated recombinant *Aspergillus* fungus capable of producing 3-hydroxypropionic acid (3-HP), comprising:

a genetic inactivation of an endogenous cis-aconitic acid decarboxylase (cadA) gene, an exogenous nucleic acid molecule encoding aspartate 1-decarboxylase (panD), an exogenous nucleic acid molecule encoding β-alanine-pyruvate aminotransferase (BAPAT), and an exogenous nucleic acid molecule encoding 3-hydroxypropionate dehydrogenase (HPDH).

2. The isolated recombinant *Aspergillus* fungus of claim 1, wherein the *Aspergillus* fungus is *Aspergillus pseudoterreus.*

3. The isolated recombinant *Aspergillus* fungus of claim 1, wherein the *Aspergillus* fungus is *Aspergillus* terreus.

4. The isolated recombinant *Aspergillus* fungus of claim 1, wherein the endogenous cadA gene is genetically inactivated by complete or partial deletion mutation or by insertional mutation.

5. The isolated recombinant *Aspergillus* fungus of claim 1, wherein the cadA gene prior to its genetic inactivation encodes a cis-aconitic acid decarboxylase with an amino acid sequence having at least 80% sequence identity to the amino acid sequence of SEQ ID NO: 50 or 52.

6. The isolated recombinant *Aspergillus* fungus of claim 1, wherein the cadA gene prior to its genetic inactivation comprises a coding sequence having at least 80% sequence identity to the nucleotide sequence of SEQ ID NO:49, 51, 59 or 92.

7. The isolated recombinant *Aspergillus* fungus of claim 1, wherein the exogenous nucleic acid molecule encoding panD comprises a nucleotide sequence having at least 80% sequence identity to the nucleotide sequence of SEQ ID NO: 53 or 65, and/or encodes an amino acid sequence having at least 80% sequence identity to the amino acid sequence of SEQ ID NO: 54.

8. The isolated recombinant *Aspergillus* fungus of claim 1, wherein the exogenous nucleic acid molecule encoding BAPAT comprises a nucleotide sequence having at least 80% sequence identity to the nucleotide sequence of SEQ ID NO: 55 or 71, and/or encodes an amino acid sequence having at least 80% sequence identity to the amino acid sequence of SEQ ID NO: 56.

9. The isolated recombinant *Aspergillus* fungus of claim 1, wherein the exogenous nucleic acid molecule encoding HPDH comprises a nucleotide sequence having at least 80% sequence identity to the nucleotide sequence of SEQ ID NO: 57 or 80, and/or encodes an amino acid sequence having at least 80% sequence identity to the amino acid sequence of SEQ ID NO: 58.

10. The isolated recombinant *Aspergillus* fungus of claim 1, wherein the exogenous nucleic acid molecule encoding panD, the exogenous nucleic acid molecule encoding BAPAT, and the exogenous nucleic acid molecule encoding HPDH are part of a single exogenous nucleic acid molecule.

11. A composition comprising the isolated recombinant *Aspergillus* fungus of claim 1.

12. A kit, comprising:

the isolated recombinant *Aspergillus* fungus of claim 1; and a medium for culturing the fungus.

13. A method of making 3-hydroxypropionic acid (3-HP), comprising:

culturing the isolated *Aspergillus* fungus of claim 1 in a culture media under conditions that permit the isolated *Aspergillus* fungus to make 3-HP; thereby making 3-HP.

14. The method of claim 13, wherein the isolated *Aspergillus* fungus is cultured in Riscaldati medium or modified Riscaldati medium comprising 20× trace elements.

15. The method of claim 13, further comprising isolating the 3-HP from the culture media or from the isolated *Aspergillus* fungus.

* * * * *

SEQUENCE LISTING

```
<160> NUMBER OF SEQ ID NOS: 98

<210> SEQ ID NO 1
<211> LENGTH: 20
<212> TYPE: DNA
<213> ORGANISM: Artificial Sequence
<220> FEATURE:
<223> OTHER INFORMATION: primer used to delete tf gene in A.
      pseudoterreus

<400> SEQUENCE: 1

gagccatagc catgcaagcg                                                20


<210> SEQ ID NO 2
```

<211> LENGTH: 21
<212> TYPE: DNA
<213> ORGANISM: Artificial Sequence
<220> FEATURE:
<223> OTHER INFORMATION: primer used to delete tf gene in A. pseudoterreus

<400> SEQUENCE: 2
atagagtcct tggatgagac g 21

<210> SEQ ID NO 3
<211> LENGTH: 21
<212> TYPE: DNA
<213> ORGANISM: Artificial Sequence
<220> FEATURE:
<223> OTHER INFORMATION: primer used to delete tf gene in A. pseudoterreus

<400> SEQUENCE: 3
gtggatttcg aggttccttg c 21

<210> SEQ ID NO 4
<211> LENGTH: 21
<212> TYPE: DNA
<213> ORGANISM: Artificial Sequence
<220> FEATURE:
<223> OTHER INFORMATION: primer used to delete tf gene in A. pseudoterreus

<400> SEQUENCE: 4
gaagtagaac catgtggatc g 21

<210> SEQ ID NO 5
<211> LENGTH: 50
<212> TYPE: DNA
<213> ORGANISM: Artificial Sequence
<220> FEATURE:
<223> OTHER INFORMATION: primer used to delete tf gene in A. pseudoterreus

<400> SEQUENCE: 5
tgacctccac tagctccagc actactagat aggcccgttt agagagtgcc 50

<210> SEQ ID NO 6
<211> LENGTH: 49
<212> TYPE: DNA
<213> ORGANISM: Artificial Sequence
<220> FEATURE:
<223> OTHER INFORMATION: primer used to delete tf gene in A. pseudoterreus

<400> SEQUENCE: 6
aatagagtag atgccgaccg gccgcttcga cgacagctct gcactctcc 49

<210> SEQ ID NO 7
<211> LENGTH: 50
<212> TYPE: DNA
<213> ORGANISM: Artificial Sequence
<220> FEATURE:
<223> OTHER INFORMATION: primer used to delete tf gene in A. pseudoterreus

<400> SEQUENCE: 7
ggcactctct aaacgggcct atctagtagt gctggagcta gtggaggtca 50

<210> SEQ ID NO 8
<211> LENGTH: 49

<212> TYPE: DNA
<213> ORGANISM: Artificial Sequence
<220> FEATURE:
<223> OTHER INFORMATION: primer used to delete tf gene in A. pseudoterreus

<400> SEQUENCE: 8
ggagagtgca gagctgtcgt cgaagcggcc ggtcggcatc tactctatt 49

<210> SEQ ID NO 9
<211> LENGTH: 20
<212> TYPE: DNA
<213> ORGANISM: Artificial Sequence
<220> FEATURE:
<223> OTHER INFORMATION: primer used to delete mttA gene in A. pseudoterreus

<400> SEQUENCE: 9
gctgcatact cggattacgc 20

<210> SEQ ID NO 10
<211> LENGTH: 20
<212> TYPE: DNA
<213> ORGANISM: Artificial Sequence
<220> FEATURE:
<223> OTHER INFORMATION: primer used to delete mttA gene in A. pseudoterreus

<400> SEQUENCE: 10
gaaaaggtac tcggagtacg 20

<210> SEQ ID NO 11
<211> LENGTH: 20
<212> TYPE: DNA
<213> ORGANISM: Artificial Sequence
<220> FEATURE:
<223> OTHER INFORMATION: primer used to delete mttA gene in A. pseudoterreus

<400> SEQUENCE: 11
cagaccaagg agctttcctg 20

<210> SEQ ID NO 12
<211> LENGTH: 20
<212> TYPE: DNA
<213> ORGANISM: Artificial Sequence
<220> FEATURE:
<223> OTHER INFORMATION: primer used to delete mttA gene in A. pseudoterreus

<400> SEQUENCE: 12
cattaagcca caggcttgcg 20

<210> SEQ ID NO 13
<211> LENGTH: 50
<212> TYPE: DNA
<213> ORGANISM: Artificial Sequence
<220> FEATURE:
<223> OTHER INFORMATION: primer used to delete mttA gene in A. pseudoterreus

<400> SEQUENCE: 13
tgacctccac tagctccagc aatatggatg ctgttcgttc gccgtgctgg 50

<210> SEQ ID NO 14
<211> LENGTH: 50
<212> TYPE: DNA

<213> ORGANISM: Artificial Sequence
<220> FEATURE:
<223> OTHER INFORMATION: primer used to delete mttA gene in A. pseudoterreus

<400> SEQUENCE: 14
aatagagtag atgccgaccg tgacgaggat gtgctgagtc caaacaaagc 50

<210> SEQ ID NO 15
<211> LENGTH: 50
<212> TYPE: DNA
<213> ORGANISM: Artificial Sequence
<220> FEATURE:
<223> OTHER INFORMATION: primer used to delete mttA gene in A. pseudoterreus

<400> SEQUENCE: 15
ccagcacggc gaacgaacag catccatatt gctggagcta gtggaggtca 50

<210> SEQ ID NO 16
<211> LENGTH: 50
<212> TYPE: DNA
<213> ORGANISM: Artificial Sequence
<220> FEATURE:
<223> OTHER INFORMATION: primer used to delete mttA gene in A. pseudoterreus

<400> SEQUENCE: 16
gctttgtttg gactcagcac atcctcgtca cggtcggcat ctactctatt 50

<210> SEQ ID NO 17
<211> LENGTH: 20
<212> TYPE: DNA
<213> ORGANISM: Artificial Sequence
<220> FEATURE:
<223> OTHER INFORMATION: primer used to delete cadA gene in A. pseudoterreus

<400> SEQUENCE: 17
ctccagtaac agaaccgacc 20

<210> SEQ ID NO 18
<211> LENGTH: 20
<212> TYPE: DNA
<213> ORGANISM: Artificial Sequence
<220> FEATURE:
<223> OTHER INFORMATION: primer used to delete cadA gene in A. pseudoterreus

<400> SEQUENCE: 18
gaacttcact gccgcattgg 20

<210> SEQ ID NO 19
<211> LENGTH: 21
<212> TYPE: DNA
<213> ORGANISM: Artificial Sequence
<220> FEATURE:
<223> OTHER INFORMATION: primer used to delete cadA gene in A. pseudoterreus

<400> SEQUENCE: 19
ggacactcca agaggataag g 21

<210> SEQ ID NO 20
<211> LENGTH: 20
<212> TYPE: DNA
<213> ORGANISM: Artificial Sequence
<220> FEATURE:
<223> OTHER INFORMATION: primer used to delete cadA gene in A. pseudoterreus

<400> SEQUENCE: 20
gctcatcaca ttgtttgccg 20

<210> SEQ ID NO 21
<211> LENGTH: 50
<212> TYPE: DNA
<213> ORGANISM: Artificial Sequence
<220> FEATURE:
<223> OTHER INFORMATION: primer used to delete cadA gene in A. pseudoterreus

<400> SEQUENCE: 21
tgacctccac tagctccagc ggtcaattta agaggacgat cttcgctgcg 50

<210> SEQ ID NO 22
<211> LENGTH: 50
<212> TYPE: DNA
<213> ORGANISM: Artificial Sequence
<220> FEATURE:
<223> OTHER INFORMATION: primer used to delete cadA gene in A. pseudoterreus

<400> SEQUENCE: 22
aatagagtag atgccgaccg tcagcctgga caggctcacc gacattagcc 50

<210> SEQ ID NO 23
<211> LENGTH: 50
<212> TYPE: DNA
<213> ORGANISM: Artificial Sequence
<220> FEATURE:
<223> OTHER INFORMATION: primer used to delete cadA gene in A. pseudoterreus

<400> SEQUENCE: 23
cgcagcgaag atcgtcctct taaattgacc gctggagcta gtggaggtca 50

<210> SEQ ID NO 24
<211> LENGTH: 50
<212> TYPE: DNA
<213> ORGANISM: Artificial Sequence
<220> FEATURE:
<223> OTHER INFORMATION: primer used to delete cadA gene in A. pseudoterreus

<400> SEQUENCE: 24
ggctaatgtc ggtgagcctg tccaggctga cggtcggcat ctactctatt 50

<210> SEQ ID NO 25
<211> LENGTH: 20
<212> TYPE: DNA
<213> ORGANISM: Artificial Sequence
<220> FEATURE:
<223> OTHER INFORMATION: primer used to delete mfsA gene in A. pseudoterreus

<400> SEQUENCE: 25
tgatgagctg aattcgttgc 20

<210> SEQ ID NO 26
<211> LENGTH: 20
<212> TYPE: DNA
<213> ORGANISM: Artificial Sequence
<220> FEATURE:

<223> OTHER INFORMATION: primer used to delete mfsA gene in A. pseudoterreus

<400> SEQUENCE: 26
tatagccagc ttttgctgtg 20

<210> SEQ ID NO 27
<211> LENGTH: 19
<212> TYPE: DNA
<213> ORGANISM: Artificial Sequence
<220> FEATURE:
<223> OTHER INFORMATION: primer used to delete mfsA gene in A. pseudoterreus

<400> SEQUENCE: 27
catagcgttc agagtgttg 19

<210> SEQ ID NO 28
<211> LENGTH: 20
<212> TYPE: DNA
<213> ORGANISM: Artificial Sequence
<220> FEATURE:
<223> OTHER INFORMATION: primer used to delete mfsA gene in A. pseudoterreus

<400> SEQUENCE: 28
ccatttcaat gctttgtgcg 20

<210> SEQ ID NO 29
<211> LENGTH: 50
<212> TYPE: DNA
<213> ORGANISM: Artificial Sequence
<220> FEATURE:
<223> OTHER INFORMATION: primer used to delete mfsA gene in A. pseudoterreus

<400> SEQUENCE: 29
ccataccacc cttaccctct tggagtgtcc gctggagcta gtggaggtca 50

<210> SEQ ID NO 30
<211> LENGTH: 50
<212> TYPE: DNA
<213> ORGANISM: Artificial Sequence
<220> FEATURE:
<223> OTHER INFORMATION: primer used to delete mfsA gene in A. pseudoterreus

<400> SEQUENCE: 30
gctgtggcct cctggcgatt acgcaatatt cggtcggcat ctactctatt 50

<210> SEQ ID NO 31
<211> LENGTH: 50
<212> TYPE: DNA
<213> ORGANISM: Artificial Sequence
<220> FEATURE:
<223> OTHER INFORMATION: primer used to delete mfsA gene in A. pseudoterreus

<400> SEQUENCE: 31
tgacctccac tagctccagc ggacactcca agagggtaag ggtggtatgg 50

<210> SEQ ID NO 32
<211> LENGTH: 50
<212> TYPE: DNA
<213> ORGANISM: Artificial Sequence
<220> FEATURE:
<223> OTHER INFORMATION: primer used to delete mfsA gene in A.

```
      pseudoterreus

<400> SEQUENCE: 32

aatagagtag atgccgaccg aatattgcgt aatcgccagg aggccacagc                  50


<210> SEQ ID NO 33
<211> LENGTH: 20
<212> TYPE: DNA
<213> ORGANISM: Artificial Sequence
<220> FEATURE:
<223> OTHER INFORMATION: primer used to delete p450 gene in A.
      pseudoterreus

<400> SEQUENCE: 33

tctccaaatc atcgtcatcg                                                   20


<210> SEQ ID NO 34
<211> LENGTH: 20
<212> TYPE: DNA
<213> ORGANISM: Artificial Sequence
<220> FEATURE:
<223> OTHER INFORMATION: primer used to delete p450 gene in A.
      pseudoterreus

<400> SEQUENCE: 34

cttcaatcgc accgacatcc                                                   20


<210> SEQ ID NO 35
<211> LENGTH: 20
<212> TYPE: DNA
<213> ORGANISM: Artificial Sequence
<220> FEATURE:
<223> OTHER INFORMATION: primer used to delete p450 gene in A.
      pseudoterreus

<400> SEQUENCE: 35

tcgtgtagac aagtccagtc                                                   20


<210> SEQ ID NO 36
<211> LENGTH: 20
<212> TYPE: DNA
<213> ORGANISM: Artificial Sequence
<220> FEATURE:
<223> OTHER INFORMATION: primer used to delete p450 gene in A.
      pseudoterreus

<400> SEQUENCE: 36

ctataccact ctagtgatgg                                                   20


<210> SEQ ID NO 37
<211> LENGTH: 50
<212> TYPE: DNA
<213> ORGANISM: Artificial Sequence
<220> FEATURE:
<223> OTHER INFORMATION: primer used to delete p450 gene in A.
      pseudoterreus

<400> SEQUENCE: 37

cctctgctca ggttgttttc gaacaggagc gctggagcta gtggaggtca                  50


<210> SEQ ID NO 38
<211> LENGTH: 50
<212> TYPE: DNA
<213> ORGANISM: Artificial Sequence
<220> FEATURE:
<223> OTHER INFORMATION: primer used to delete p450 gene in A.
      pseudoterreus
```

<400> SEQUENCE: 38
cggaatgcag ataggcatca cagtccagaa cggtcggcat ctactctatt 50

<210> SEQ ID NO 39
<211> LENGTH: 50
<212> TYPE: DNA
<213> ORGANISM: Artificial Sequence
<220> FEATURE:
<223> OTHER INFORMATION: primer used to delete p450 gene in A. pseudoterreus

<400> SEQUENCE: 39
tgacctccac tagctccagc gctcctgttc gaaaacaacc tgagcagagg 50

<210> SEQ ID NO 40
<211> LENGTH: 50
<212> TYPE: DNA
<213> ORGANISM: Artificial Sequence
<220> FEATURE:
<223> OTHER INFORMATION: primer used to delete p450 gene in A. pseudoterreus

<400> SEQUENCE: 40
aatagagtag atgccgaccg ttctggactg tgatgcctat ctgcattccg 50

<210> SEQ ID NO 41
<211> LENGTH: 20
<212> TYPE: DNA
<213> ORGANISM: Artificial Sequence
<220> FEATURE:
<223> OTHER INFORMATION: primer used to amplify mttA in A. pseudoterreus

<400> SEQUENCE: 41
gctttcaatg tggttcctac 20

<210> SEQ ID NO 42
<211> LENGTH: 19
<212> TYPE: DNA
<213> ORGANISM: Artificial Sequence
<220> FEATURE:
<223> OTHER INFORMATION: primer used to amplify mttA in A. pseudoterreus

<400> SEQUENCE: 42
ctccatcacc taccctttc 19

<210> SEQ ID NO 43
<211> LENGTH: 17
<212> TYPE: DNA
<213> ORGANISM: Artificial Sequence
<220> FEATURE:
<223> OTHER INFORMATION: primer used to amplify cadA in A. pseudoterreus

<400> SEQUENCE: 43
gaagtgtggg atctggc 17

<210> SEQ ID NO 44
<211> LENGTH: 19
<212> TYPE: DNA
<213> ORGANISM: Artificial Sequence
<220> FEATURE:
<223> OTHER INFORMATION: primer used to amplify cadA in A. pseudoterreus

<400> SEQUENCE: 44
gggttcggta tttgtgaag 19

<210> SEQ ID NO 45
<211> LENGTH: 20
<212> TYPE: DNA
<213> ORGANISM: Artificial Sequence
<220> FEATURE:
<223> OTHER INFORMATION: primer used to amplify mfsA in A. pseudoterreus

<400> SEQUENCE: 45
caagaacagt ttggcctgag 20

<210> SEQ ID NO 46
<211> LENGTH: 20
<212> TYPE: DNA
<213> ORGANISM: Artificial Sequence
<220> FEATURE:
<223> OTHER INFORMATION: primer used to amplify mfsA in A. pseudoterreus

<400> SEQUENCE: 46
gcggacatca tacaatctgg 20

<210> SEQ ID NO 47
<211> LENGTH: 20
<212> TYPE: DNA
<213> ORGANISM: Artificial Sequence
<220> FEATURE:
<223> OTHER INFORMATION: primer used to amplify beta-tubulin in A. pseudoterreus

<400> SEQUENCE: 47
ttgtcgatgt tgttcgtcgc 20

<210> SEQ ID NO 48
<211> LENGTH: 20
<212> TYPE: DNA
<213> ORGANISM: Artificial Sequence
<220> FEATURE:
<223> OTHER INFORMATION: primer used to amplify beta-tubulin in A. pseudoterreus

<400> SEQUENCE: 48
tggcgttgta aggctcaacc 20

<210> SEQ ID NO 49
<211> LENGTH: 2206
<212> TYPE: DNA
<213> ORGANISM: Aspergillus terreus

<400> SEQUENCE: 49
gtgggtcttg aaatcgtatg ccacacttgc tccggatgaa acacattccg gagcgcgcat 60
cgatattgct acacagtata gacccaatgg tctgcagatg ccctaaatgg tagttctcac 120
tggcctgcat taagttctgg ttgcagatca ttgtcggcct aacatcagtg taggttacgg 180
tgtgagattt acttgcatag aagattccag accacaaggt tctagatcct ttgacggcgg 240
actcccctcg aggtgccggg cgccgacgtg tgcgttgctc cgggatttgt aggacgcagc 300
tcggatacct agccgttatg ggaatcggag gttgtagcag cgtaaacaca tggatagtta 360
aataatcgga tgtacaccca ctgttggaaa tgacgggggc ctacaacacg agattatctg 420
atccaatttc tgttcgttgg cattctatca ttcgcagcga aaattgtcct attaaattga 480

```
ccatgaccaa acaatctgcg gacagcaacg caaagtcagg agttacgtcc gaaatatgtc    540

attgggcatc caacctggcc actgacgaca tcccttcgga cgtattagaa agagcaaaat    600

accttattct cgacggtatt gcatgtgcct gggttggtgc aagagtgcct tggtcagaga    660

agtatgttca ggcaacgatg agctttgagc cgccgggggc ctgcagggtg attggatatg    720

gacaggtaaa ttttattcac tctagacggt ccacaaagta tactgacgat ccttcgtata    780

gaaactgggg cctgttgcag cagccatgac caattccgct ttcatacagg ctacggagct    840

tgacgactac cacagcgaag ccccccctaca ctctgcaagc attgtccttc ctgcggtctt    900

tgcagcaagt gaggtcttag ccgagcaggg caaaacaatt tccggtatag atgttattct    960

agccgccatt gtggggtttg aatctggccc acggatcggc aaagcaatct acggatcgga   1020

cctcttgaac aacggctggc attgtggagc tgtgtatggc gctccagccg gtgcgctggc   1080

cacaggaaag ctcctcggtc taactccaga ctccatggaa gatgctctcg gaattgcgtg   1140

cacgcaagcc tgtggtttaa tgtcggcgca atacggaggc atggtaaagc gtgtgcaaca   1200

cggattcgca gcgcgtaatg gtcttcttgg gggactgttg gcccatggtg ggtacgaggc   1260

aatgaaaggt gtcctggaga gatcttacgg cggtttcctc aagatgttca ccaagggcaa   1320

cggcagagag cctccctaca aagaggagga agtggtggct ggtctcggtt cattctggca   1380

tacctttact attcgcatca agctctatgc ctgctgcgga cttgtccatg gtccagtcga   1440

ggctatcgaa aaccttcagg ggagataccc cgagctcttg aatagagcca acctcagcaa   1500

cattcgccat gttcatgtac agctttcaac ggcctcgaac agtcactgtg gatggatacc   1560

agaggagaga cccatcagtt caatcgcagg gcagatgagt gtcgcataca ttctcgccgt   1620

ccagctggtc gaccagcaat gtcttttgtc ccagttttct gagtttgatg acaacctgga   1680

gaggccagaa gtttgggatc tggccaggaa ggttacttca tctcaaagcg aagagtttga   1740

tcaagacggc aactgtctca gtgcgggtcg cgtgaggatt gagttcaacg atggttcttc   1800

tattacggaa agtgtcgaga agcctcttgg tgtcaaagag cccatgccaa acgaacggat   1860

tctccacaaa taccgaaccc ttgctggtag cgtgacggac gaatcccggg tgaaagagat   1920

tgaggatctt gtcctcggcc tggacaggct caccgacatt agcccattgc tggagctgct   1980

gaattgcccc gtgaaatcgc cactggtata aatgggaagc gatatggaaa catttcatgt   2040

cacgggcaca aattctaggt catatcgtac ctggatggtg aaaccaccag cggtttagca   2100

gatagaagat agactccttc tgctctgcgt tgcgtcttga atttagttcg ttcactggct   2160

taagaactta gaatgcaata cagtctctct tatttcttat taaaat                  2206
```

<210> SEQ ID NO 50
<211> LENGTH: 490
<212> TYPE: PRT
<213> ORGANISM: Aspergillus terreus

<400> SEQUENCE: 50

```
Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60
```

-continued

```
Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
    290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
        355                 360                 365

Leu Leu Ser Gln Phe Ser Glu Phe Asp Asp Asn Leu Glu Arg Pro Glu
    370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Ile Thr Glu Ser Val Glu Lys Pro Leu Gly Val
            420                 425                 430

Lys Glu Pro Met Pro Asn Glu Arg Ile Leu His Lys Tyr Arg Thr Leu
        435                 440                 445

Ala Gly Ser Val Thr Asp Glu Ser Arg Val Lys Glu Ile Glu Asp Leu
    450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
```

485 490

<210> SEQ ID NO 51
<211> LENGTH: 1862
<212> TYPE: DNA
<213> ORGANISM: Aspergillus vadensis

<400> SEQUENCE: 51
gttttctgtg tgtctttggg gggttataaa tagggtgtcg aatatctgga agatagggaa 60
ttctttctct ttcaatcaat caatcaagaa ttcttttagg gagtttctat actacatccg 120
atatggtcgc catcaccgct aaatctgaag cggcttctgc tacttcgccc attcctacca 180
attctaatac taccatgact actaccctca acggggtaga tggttcaaaa gagaaagaaa 240
aagaccagat acccccaaac aaagaggaag gaacaaaagc agaagagaaa gaaaccgaag 300
catacaactc ctccaacggc gtcaccagcc aactctgcaa ctggatcgcc tctctccagc 360
tagaagacat tccagactct gtccgcaccc gcgccaagta cctctttctc gatggcatcg 420
cctgcgcact cgtcggtgcg cgcgtcccat ggtcgcagaa ggcttttgat gcgatggctg 480
ttttcgagga gaagggaaag catgtggtta ttgggtatga agagcgcctt ggtgctatcg 540
ccgccgcaac cctcaacggc tcctggatcc aagcctgcga agtagacgac taccacagcg 600
tggcgcccct gcactcgcag gccgtggtca tccctcctct cttcgctgcc gccgtcagtg 660
cgcggaacca tccgaccgca ccgcgcatca tcgacgggcg aacacttctt ctcgcctccg 720
tggtagggtt cgaggttggt ccgcgcgtgg gcatggcgct acacggcacc gagatgctcg 780
cgaagggatg gcactgcggg tctgtgtttg gtggacccgc ggccgcaggc agttctgcaa 840
aactactcgg tttgtcggcg ggtcaagtcg aagacgcgat cggagtagca gcgacacaag 900
catgcggact catggcggcg cagtacgacg ggatggtgaa gcggatgcat catggcttcg 960
cggcaaggaa tggactgttg ggcacgatgt tagcgtgggg aggttatgaa gggatcaaga 1020
aggtgtttga gcggccgtat ggaggatttc tggcaatgtt tggcctaggg tcgaagcaca 1080
cgcctagttc gaagccggag gaggtggcaa aggatttggg gacgttctgg cacacggcgg 1140
agtggattcg gttgaagttg catgcgtgct gtggggggat tcatggcacg attgagtgtt 1200
tggcggagat gcaggagatg tatccagagc gatttggacg ggagaaacta ggagagatca 1260
aggagattcg gatccagttg agtgatgcgg tgtttcatca ttgtggatgg gcgccggaga 1320
cgaggccgtt gaccccgacg gggcgcaga tgaatacggc gtttgtggcg gcctcgcagt 1380
tggtggatgg acaagtgttg ttggagcagt tctcgtcggg gaagttggat cgggatgagg 1440
tttgggaatt gattgggaag acgagttgta ttcatacggc ggagttggac aagccgaata 1500
ttggttgtgg tgcgttgatc tccatcacgt ttgcggatgg cagtcaggtt cagcattcgt 1560
tgttgaagcc gaagggggtg gatgaaccca tttcgaatga ggagatcttg gagaagtttc 1620
gtcggttgac gggcgggttg attggggtgg agaggcagga gaagattgaa aaggccgtgc 1680
tggggatgga ggagttgcag gatgtggatg agttgattga gttgctgagt gtgaatgtgg 1740
tcaatccgtt gcagtagtat actagtcatc tgttttgatg cttctggcgt tggtcgtgtt 1800
gggatagtat ctcataattt tgaattaata aatcattcaa catggtgaaa atcatatttg 1860
tg 1862

<210> SEQ ID NO 52
<211> LENGTH: 544
<212> TYPE: PRT
<213> ORGANISM: Aspergillus vadensis

<400> SEQUENCE: 52

```
Met Val Ala Ile Thr Ala Lys Ser Glu Ala Ala Ser Ala Thr Ser Pro
1               5                   10                  15

Ile Pro Thr Asn Ser Asn Thr Thr Met Thr Thr Thr Leu Asn Gly Val
            20                  25                  30

Asp Gly Ser Lys Glu Lys Glu Lys Asp Gln Ile Pro Pro Asn Lys Glu
        35                  40                  45

Glu Gly Thr Lys Ala Glu Glu Lys Glu Thr Glu Ala Tyr Asn Ser Ser
    50                  55                  60

Asn Gly Val Thr Ser Gln Leu Cys Asn Trp Ile Ala Ser Leu Gln Leu
65                  70                  75                  80

Glu Asp Ile Pro Asp Ser Val Arg Thr Arg Ala Lys Tyr Leu Phe Leu
                85                  90                  95

Asp Gly Ile Ala Cys Ala Leu Val Gly Ala Arg Val Pro Trp Ser Gln
            100                 105                 110

Lys Ala Phe Asp Ala Met Ala Val Phe Glu Glu Lys Gly Lys His Val
        115                 120                 125

Val Ile Gly Tyr Glu Glu Arg Leu Gly Ala Ile Ala Ala Ala Thr Leu
    130                 135                 140

Asn Gly Ser Trp Ile Gln Ala Cys Glu Val Asp Asp Tyr His Ser Val
145                 150                 155                 160

Ala Pro Leu His Ser Gln Ala Val Val Ile Pro Pro Leu Phe Ala Ala
                165                 170                 175

Ala Val Ser Ala Arg Asn His Pro Thr Ala Pro Arg Ile Ile Asp Gly
            180                 185                 190

Arg Thr Leu Leu Leu Ala Ser Val Val Gly Phe Glu Val Gly Pro Arg
        195                 200                 205

Val Gly Met Ala Leu His Gly Thr Glu Met Leu Ala Lys Gly Trp His
    210                 215                 220

Cys Gly Ser Val Phe Gly Gly Pro Ala Ala Ala Gly Ser Ser Ala Lys
225                 230                 235                 240

Leu Leu Gly Leu Ser Ala Gly Gln Val Glu Asp Ala Ile Gly Val Ala
                245                 250                 255

Ala Thr Gln Ala Cys Gly Leu Met Ala Ala Gln Tyr Asp Gly Met Val
            260                 265                 270

Lys Arg Met His His Gly Phe Ala Ala Arg Asn Gly Leu Leu Gly Thr
        275                 280                 285

Met Leu Ala Trp Gly Gly Tyr Glu Gly Ile Lys Lys Val Phe Glu Arg
    290                 295                 300

Pro Tyr Gly Gly Phe Leu Ala Met Phe Gly Leu Gly Ser Lys His Thr
305                 310                 315                 320

Pro Ser Ser Lys Pro Glu Glu Val Ala Lys Asp Leu Gly Thr Phe Trp
                325                 330                 335

His Thr Ala Glu Trp Ile Arg Leu Lys Leu His Ala Cys Cys Gly Gly
            340                 345                 350

Ile His Gly Thr Ile Glu Cys Leu Ala Glu Met Gln Glu Met Tyr Pro
        355                 360                 365

Glu Arg Phe Gly Arg Glu Lys Leu Gly Glu Ile Lys Glu Ile Arg Ile
    370                 375                 380

Gln Leu Ser Asp Ala Val Phe His His Cys Gly Trp Ala Pro Glu Thr
385                 390                 395                 400

Arg Pro Leu Thr Pro Thr Gly Ala Gln Met Asn Thr Ala Phe Val Ala
```

```
                405                 410                 415

Ala Ser Gln Leu Val Asp Gly Gln Val Leu Leu Glu Gln Phe Ser Ser
            420                 425                 430

Gly Lys Leu Asp Arg Asp Glu Val Trp Glu Leu Ile Gly Lys Thr Ser
        435                 440                 445

Cys Ile His Thr Ala Glu Leu Asp Lys Pro Asn Ile Gly Cys Gly Ala
    450                 455                 460

Leu Ile Ser Ile Thr Phe Ala Asp Gly Ser Gln Val Gln His Ser Leu
465                 470                 475                 480

Leu Lys Pro Lys Gly Val Asp Glu Pro Ile Ser Asn Glu Glu Ile Leu
                485                 490                 495

Glu Lys Phe Arg Arg Leu Thr Gly Gly Leu Ile Gly Val Glu Arg Gln
            500                 505                 510

Glu Lys Ile Glu Lys Ala Val Leu Gly Met Glu Glu Leu Gln Asp Val
        515                 520                 525

Asp Glu Leu Ile Glu Leu Leu Ser Val Asn Val Val Asn Pro Leu Gln
    530                 535                 540


<210> SEQ ID NO 53
<211> LENGTH: 1797
<212> TYPE: DNA
<213> ORGANISM: Tribolium castaneum
<220> FEATURE:
<221> NAME/KEY: CDS
<222> LOCATION: (41)..(1663)

<400> SEQUENCE: 53

acttgtgaat cagtcgtgcc cccacgagga tccacacacg atg ccg gcc aca ggc       55
                                            Met Pro Ala Thr Gly
                                            1               5

gaa gac caa gac ctg gtg caa gac ctc atc gag gag ccc gcc acc ttc      103
Glu Asp Gln Asp Leu Val Gln Asp Leu Ile Glu Glu Pro Ala Thr Phe
                10                  15                  20

agc gac gcc gtc ctc tcc tcc gac gag gaa ctc ttc cac cag aag tgc      151
Ser Asp Ala Val Leu Ser Ser Asp Glu Glu Leu Phe His Gln Lys Cys
            25                  30                  35

ccc aaa ccc gcc ccc att tac tcc ccg gtc tcg aaa ccg gtc tcc ttc      199
Pro Lys Pro Ala Pro Ile Tyr Ser Pro Val Ser Lys Pro Val Ser Phe
        40                  45                  50

gag agc ctc ccc aac agg cgc ctc cac gag gag ttc ctc cgc agc tcg      247
Glu Ser Leu Pro Asn Arg Arg Leu His Glu Glu Phe Leu Arg Ser Ser
    55                  60                  65

gtg gac gtc ctc ctc cag gag gcg gtg ttc gag gga acg aac cgc aag      295
Val Asp Val Leu Leu Gln Glu Ala Val Phe Glu Gly Thr Asn Arg Lys
70                  75                  80                  85

aac cgg gtg ctg caa tgg cgg gag ccg gag gag ttg agg cgt ctg atg      343
Asn Arg Val Leu Gln Trp Arg Glu Pro Glu Glu Leu Arg Arg Leu Met
                90                  95                  100

gac ttt ggg gtg cgg agt gcg ccc tcc acg cac gag gag ttg ttg gag      391
Asp Phe Gly Val Arg Ser Ala Pro Ser Thr His Glu Glu Leu Leu Glu
            105                 110                 115

gtg ttg aag aag gtt gta act tat tcg gtt aaa acc gga cat ccg tac      439
Val Leu Lys Lys Val Val Thr Tyr Ser Val Lys Thr Gly His Pro Tyr
        120                 125                 130

ttc gtg aac cag ttg ttc tcg gcg gtg gat ccg tac ggt ttg gtg gca      487
Phe Val Asn Gln Leu Phe Ser Ala Val Asp Pro Tyr Gly Leu Val Ala
    135                 140                 145

caa tgg gcc acg gat gcg ctc aat ccg agt gtt tac acc tac gag gtt      535
Gln Trp Ala Thr Asp Ala Leu Asn Pro Ser Val Tyr Thr Tyr Glu Val
```

```
150                 155                 160                 165

tcg ccg gtt ttt gtt ctg atg gag gaa gtg gtt ttg agg gag atg agg       583
Ser Pro Val Phe Val Leu Met Glu Glu Val Val Leu Arg Glu Met Arg
                170                 175                 180

gcc att gtg ggg ttc gag ggg gga aag ggc gat ggg att ttt tgc cca       631
Ala Ile Val Gly Phe Glu Gly Gly Lys Gly Asp Gly Ile Phe Cys Pro
            185                 190                 195

gga ggg tcc att gcc aat gga tat gcc atc agt tgt gcc aga tac agg       679
Gly Gly Ser Ile Ala Asn Gly Tyr Ala Ile Ser Cys Ala Arg Tyr Arg
        200                 205                 210

ttt atg ccc gat att aag aaa aaa ggc ctc cac tct ctc ccc cgt ttg       727
Phe Met Pro Asp Ile Lys Lys Lys Gly Leu His Ser Leu Pro Arg Leu
    215                 220                 225

gtc ctc ttc acc tct gaa gat gcc cac tat tcc atc aaa aaa ctc gcc       775
Val Leu Phe Thr Ser Glu Asp Ala His Tyr Ser Ile Lys Lys Leu Ala
230                 235                 240                 245

tct ttc caa ggc atc ggc acc gac aac gtc tac ttg ata cga acg gac       823
Ser Phe Gln Gly Ile Gly Thr Asp Asn Val Tyr Leu Ile Arg Thr Asp
                250                 255                 260

gcc cga ggt cgc atg gac gtc tcg cac ctg gtg gag gaa atc gag cgt       871
Ala Arg Gly Arg Met Asp Val Ser His Leu Val Glu Glu Ile Glu Arg
            265                 270                 275

tcg ctc cgt gaa ggc gcc gct cct ttc atg gtc agt gcc acc gct gga       919
Ser Leu Arg Glu Gly Ala Ala Pro Phe Met Val Ser Ala Thr Ala Gly
        280                 285                 290

acc aca gtg att ggt gcc ttt gac ccc atc gaa aaa atc gca gat gtg       967
Thr Thr Val Ile Gly Ala Phe Asp Pro Ile Glu Lys Ile Ala Asp Val
    295                 300                 305

tgc caa aaa tac aaa ctg tgg ttg cac gtg gat gcc gcc tgg gga ggt      1015
Cys Gln Lys Tyr Lys Leu Trp Leu His Val Asp Ala Ala Trp Gly Gly
310                 315                 320                 325

ggc gcg ctt gtc tct gcc aaa cac cgc cac ctc ctc aaa ggg att gag      1063
Gly Ala Leu Val Ser Ala Lys His Arg His Leu Leu Lys Gly Ile Glu
                330                 335                 340

agg gcc gac tcg gtc acc tgg aac cct cac aaa ctc cta aca gcc ccc      1111
Arg Ala Asp Ser Val Thr Trp Asn Pro His Lys Leu Leu Thr Ala Pro
            345                 350                 355

cag caa tgt tcc aca ctt tta ctg cga cat gag ggt gtc ctc gcc gag      1159
Gln Gln Cys Ser Thr Leu Leu Leu Arg His Glu Gly Val Leu Ala Glu
        360                 365                 370

gcg cat tcc acg aac gcc gct tac ctc ttc caa aaa gac aaa ttc tac      1207
Ala His Ser Thr Asn Ala Ala Tyr Leu Phe Gln Lys Asp Lys Phe Tyr
    375                 380                 385

gac acc aaa tac gac acg ggc gac aag cac atc cag tgc ggc cgc agg      1255
Asp Thr Lys Tyr Asp Thr Gly Asp Lys His Ile Gln Cys Gly Arg Arg
390                 395                 400                 405

gcc gac gtc ctc aag ttc tgg ttc atg tgg aag gcg aag gga aca tca      1303
Ala Asp Val Leu Lys Phe Trp Phe Met Trp Lys Ala Lys Gly Thr Ser
                410                 415                 420

ggg ttg gag aaa cac gtc gat aaa gtg ttc gaa aat gcg aga ttt ttc      1351
Gly Leu Glu Lys His Val Asp Lys Val Phe Glu Asn Ala Arg Phe Phe
            425                 430                 435

acc gat tgt ata aaa aat cgg gaa ggg ttt gaa atg gtg ata gcg gag      1399
Thr Asp Cys Ile Lys Asn Arg Glu Gly Phe Glu Met Val Ile Ala Glu
        440                 445                 450

ccc gaa tac aca aac atc tgc ttt tgg tac gtg ccg aag agt ctg agg      1447
Pro Glu Tyr Thr Asn Ile Cys Phe Trp Tyr Val Pro Lys Ser Leu Arg
    455                 460                 465

ggg cgc aag gac gaa gcc gat tac aaa gac aag ctg cat aag gtg gcc      1495
```

```
Gly Arg Lys Asp Glu Ala Asp Tyr Lys Asp Lys Leu His Lys Val Ala
470                 475                 480                 485

ccc agg att aag gag agg atg atg aag gag ggc tcc atg atg gtc acg     1543
Pro Arg Ile Lys Glu Arg Met Met Lys Glu Gly Ser Met Met Val Thr
                490                 495                 500

tac cag gcg caa aag gga cac ccg aat ttt ttc agg att gtg ttc cag     1591
Tyr Gln Ala Gln Lys Gly His Pro Asn Phe Phe Arg Ile Val Phe Gln
            505                 510                 515

aat tcg ggg ctt gac aag gct gat atg gtg cac ctt gtt gag gag att     1639
Asn Ser Gly Leu Asp Lys Ala Asp Met Val His Leu Val Glu Glu Ile
        520                 525                 530

gag cgg ttg ggg agc gat ctt taa ggccttgaat ggtgctagtt gtagattgtg    1693
Glu Arg Leu Gly Ser Asp Leu
    535                 540

taattaatgt aaaaagtatt atttaaaaaa tgtaaatttt gatgtattta ttctcattag   1753

ttgtagttta ttcaaataaa agtttaaaaa aaaaaaaaaa aaaa                    1797


<210> SEQ ID NO 54
<211> LENGTH: 540
<212> TYPE: PRT
<213> ORGANISM: Tribolium castaneum

<400> SEQUENCE: 54

Met Pro Ala Thr Gly Glu Asp Gln Asp Leu Val Gln Asp Leu Ile Glu
1               5                   10                  15

Glu Pro Ala Thr Phe Ser Asp Ala Val Leu Ser Ser Asp Glu Glu Leu
            20                  25                  30

Phe His Gln Lys Cys Pro Lys Pro Ala Pro Ile Tyr Ser Pro Val Ser
        35                  40                  45

Lys Pro Val Ser Phe Glu Ser Leu Pro Asn Arg Arg Leu His Glu Glu
    50                  55                  60

Phe Leu Arg Ser Ser Val Asp Val Leu Leu Gln Glu Ala Val Phe Glu
65                  70                  75                  80

Gly Thr Asn Arg Lys Asn Arg Val Leu Gln Trp Arg Glu Pro Glu Glu
                85                  90                  95

Leu Arg Arg Leu Met Asp Phe Gly Val Arg Ser Ala Pro Ser Thr His
            100                 105                 110

Glu Glu Leu Leu Glu Val Leu Lys Lys Val Val Thr Tyr Ser Val Lys
        115                 120                 125

Thr Gly His Pro Tyr Phe Val Asn Gln Leu Phe Ser Ala Val Asp Pro
    130                 135                 140

Tyr Gly Leu Val Ala Gln Trp Ala Thr Asp Ala Leu Asn Pro Ser Val
145                 150                 155                 160

Tyr Thr Tyr Glu Val Ser Pro Val Phe Val Leu Met Glu Glu Val Val
                165                 170                 175

Leu Arg Glu Met Arg Ala Ile Val Gly Phe Glu Gly Gly Lys Gly Asp
            180                 185                 190

Gly Ile Phe Cys Pro Gly Gly Ser Ile Ala Asn Gly Tyr Ala Ile Ser
        195                 200                 205

Cys Ala Arg Tyr Arg Phe Met Pro Asp Ile Lys Lys Lys Gly Leu His
    210                 215                 220

Ser Leu Pro Arg Leu Val Leu Phe Thr Ser Glu Asp Ala His Tyr Ser
225                 230                 235                 240

Ile Lys Lys Leu Ala Ser Phe Gln Gly Ile Gly Thr Asp Asn Val Tyr
                245                 250                 255
```

```
Leu Ile Arg Thr Asp Ala Arg Gly Arg Met Asp Val Ser His Leu Val
            260                 265                 270

Glu Glu Ile Glu Arg Ser Leu Arg Glu Gly Ala Ala Pro Phe Met Val
        275                 280                 285

Ser Ala Thr Ala Gly Thr Thr Val Ile Gly Ala Phe Asp Pro Ile Glu
    290                 295                 300

Lys Ile Ala Asp Val Cys Gln Lys Tyr Lys Leu Trp Leu His Val Asp
305                 310                 315                 320

Ala Ala Trp Gly Gly Gly Ala Leu Val Ser Ala Lys His Arg His Leu
                325                 330                 335

Leu Lys Gly Ile Glu Arg Ala Asp Ser Val Thr Trp Asn Pro His Lys
            340                 345                 350

Leu Leu Thr Ala Pro Gln Gln Cys Ser Thr Leu Leu Leu Arg His Glu
        355                 360                 365

Gly Val Leu Ala Glu Ala His Ser Thr Asn Ala Ala Tyr Leu Phe Gln
    370                 375                 380

Lys Asp Lys Phe Tyr Asp Thr Lys Tyr Asp Thr Gly Asp Lys His Ile
385                 390                 395                 400

Gln Cys Gly Arg Arg Ala Asp Val Leu Lys Phe Trp Phe Met Trp Lys
                405                 410                 415

Ala Lys Gly Thr Ser Gly Leu Glu Lys His Val Asp Lys Val Phe Glu
            420                 425                 430

Asn Ala Arg Phe Phe Thr Asp Cys Ile Lys Asn Arg Glu Gly Phe Glu
        435                 440                 445

Met Val Ile Ala Glu Pro Glu Tyr Thr Asn Ile Cys Phe Trp Tyr Val
    450                 455                 460

Pro Lys Ser Leu Arg Gly Arg Lys Asp Glu Ala Asp Tyr Lys Asp Lys
465                 470                 475                 480

Leu His Lys Val Ala Pro Arg Ile Lys Glu Arg Met Met Lys Glu Gly
                485                 490                 495

Ser Met Met Val Thr Tyr Gln Ala Gln Lys Gly His Pro Asn Phe Phe
            500                 505                 510

Arg Ile Val Phe Gln Asn Ser Gly Leu Asp Lys Ala Asp Met Val His
        515                 520                 525

Leu Val Glu Glu Ile Glu Arg Leu Gly Ser Asp Leu
    530                 535                 540
```

<210> SEQ ID NO 55
<211> LENGTH: 1356
<212> TYPE: DNA
<213> ORGANISM: Bacillus cereus

<400> SEQUENCE: 55

```
ttaaagttga gctaaacatt ctttcattgt tttaacgata aaagtaaagt cttcctctgt      60

gatgcttaat ggaggtgcaa gctgcaaaat attattgtaa cctgcaacag tgtcaccatt     120

tttaccaata attagacctt tttctttaca agcattgatg actttgttca tcttttcaat     180

ggaagccggt tcttttgttt gcttatcttc cactagttca atacctaaaa gaaggccttt     240

tccgcgaaca tctcctacgt ttggatgctc ttttacatct tctagttcat ataacagtcg     300

ttcacccaat tctttggaac gttcaatgag tttctcattc tccataattt ctaaattctt     360

caaagctaag gcgcaagcag caggatttcc tccaaacgta tttacatggc ggaagcgatc     420

ataatcatca ctgcctacga atgcctcata aacctctcgt ctaactgctg ttgctgacaa     480

aggaagatac gcacttgtaa tacctttttgc cattgtaatg atatctggtt tgacgccata     540
```

```
attcataaat ccaaacggct tccctgttcg tccaaatcca catataactt catcacaaat    600

gagcaacgca ccatgcttct cgcaaatttc ttttactttt tccatatatc catcaggagg    660

cattaaaatt ccgcccccag taatgattgg ctccataatc acaccggcta ctgtttggct    720

taactcccat gtcatgacac gatcgatttc ctcagcactt gccagtgtat gaacatcctc    780

tggattgcga tacgtatcag gcggtgctac atgcaaaaaa ccttgtccta atggctcata    840

tttatacttt ctttgtgctt gccctgttgc tgcaagagca cccattgagt taccgtgata    900

agcgcggtag cgggaaataa acttatagcg tccatgatca ccttttttgct gatgatattg    960

acgagcaatt ttaaatgctg tttcatttgc ttctgatcca ctgttagaaa agaaaatgac   1020

gtattcatca tccagccatt cattcaattt ctctgctaat ttaatggcag gaacatgact   1080

ttgtgtcaga gggaaatatg gcatttcttc aagttgctca aatgccgctc ttgcaagctc   1140

ttttcggccg tatccaacat tcacacacca aagaccagac ataccgtcta aataacggtt   1200

tccatcaata tccgtcaccc atgccccttc tgcttttgtg ataattaaat tcgttggact   1260

aggggccgct cctctcatcg catgccaaag gtacttttca tctgtttttt tcaaactttg   1320

tgtttgctct gtcacttgca caatcatcag ctccat                             1356
```

<210> SEQ ID NO 56
<211> LENGTH: 451
<212> TYPE: PRT
<213> ORGANISM: Bacillus cereus

<400> SEQUENCE: 56

```
Met Glu Leu Met Ile Val Gln Val Thr Glu Gln Thr Gln Ser Leu Lys
1               5                   10                  15

Lys Thr Asp Glu Lys Tyr Leu Trp His Ala Met Arg Gly Ala Ala Pro
            20                  25                  30

Ser Pro Thr Asn Leu Ile Ile Thr Lys Ala Glu Gly Ala Trp Val Thr
        35                  40                  45

Asp Ile Asp Gly Asn Arg Tyr Leu Asp Gly Met Ser Gly Leu Trp Cys
    50                  55                  60

Val Asn Val Gly Tyr Gly Arg Lys Glu Leu Ala Arg Ala Ala Phe Glu
65                  70                  75                  80

Gln Leu Glu Glu Met Pro Tyr Phe Pro Leu Thr Gln Ser His Val Pro
                85                  90                  95

Ala Ile Lys Leu Ala Glu Lys Leu Asn Glu Trp Leu Asp Asp Glu Tyr
            100                 105                 110

Val Ile Phe Phe Ser Asn Ser Gly Ser Glu Ala Asn Glu Thr Ala Phe
        115                 120                 125

Lys Ile Ala Arg Gln Tyr His Gln Gln Lys Gly Asp His Gly Arg Tyr
    130                 135                 140

Lys Phe Ile Ser Arg Tyr Arg Ala Tyr His Gly Asn Ser Met Gly Ala
145                 150                 155                 160

Leu Ala Ala Thr Gly Gln Ala Gln Arg Lys Tyr Lys Tyr Glu Pro Leu
                165                 170                 175

Gly Gln Gly Phe Leu His Val Ala Pro Pro Asp Thr Tyr Arg Asn Pro
            180                 185                 190

Glu Asp Val His Thr Leu Ala Ser Ala Glu Glu Ile Asp Arg Val Met
        195                 200                 205

Thr Trp Glu Leu Ser Gln Thr Val Ala Gly Val Ile Met Glu Pro Ile
    210                 215                 220
```

```
Ile Thr Gly Gly Gly Ile Leu Met Pro Pro Asp Gly Tyr Met Glu Lys
225                 230                 235                 240

Val Lys Glu Ile Cys Glu Lys His Gly Ala Leu Leu Ile Cys Asp Glu
                245                 250                 255

Val Ile Cys Gly Phe Gly Arg Thr Gly Lys Pro Phe Gly Phe Met Asn
            260                 265                 270

Tyr Gly Val Lys Pro Asp Ile Ile Thr Met Ala Lys Gly Ile Thr Ser
        275                 280                 285

Ala Tyr Leu Pro Leu Ser Ala Thr Ala Val Arg Arg Glu Val Tyr Glu
    290                 295                 300

Ala Phe Val Gly Ser Asp Asp Tyr Asp Arg Phe Arg His Val Asn Thr
305                 310                 315                 320

Phe Gly Gly Asn Pro Ala Ala Cys Ala Leu Ala Leu Lys Asn Leu Glu
                325                 330                 335

Ile Met Glu Asn Glu Lys Leu Ile Glu Arg Ser Lys Glu Leu Gly Glu
            340                 345                 350

Arg Leu Leu Tyr Glu Leu Glu Asp Val Lys Glu His Pro Asn Val Gly
        355                 360                 365

Asp Val Arg Gly Lys Gly Leu Leu Leu Gly Ile Glu Leu Val Glu Asp
    370                 375                 380

Lys Gln Thr Lys Glu Pro Ala Ser Ile Glu Lys Met Asn Lys Val Ile
385                 390                 395                 400

Asn Ala Cys Lys Glu Lys Gly Leu Ile Ile Gly Lys Asn Gly Asp Thr
                405                 410                 415

Val Ala Gly Tyr Asn Asn Ile Leu Gln Leu Ala Pro Pro Leu Ser Ile
            420                 425                 430

Thr Glu Glu Asp Phe Thr Phe Ile Val Lys Thr Met Lys Glu Cys Leu
        435                 440                 445

Ala Gln Leu
    450
```

```
<210> SEQ ID NO 57
<211> LENGTH: 747
<212> TYPE: DNA
<213> ORGANISM: Escherichia coli

<400> SEQUENCE: 57

atgatcgttt tagtaactgg agcaacggca ggttttggtg aatgcattac tcgtcgtttt      60

attcaacaag ggcataaagt tatcgccact ggccgtcgcc aggagcggtt gcaggagtta     120

aaagacgaac tgggagataa tctgtatatc gcccaactgg acgttcgcaa ccgcgccgct     180

attgaagaga tgctggcatc gcttcctgcc gagtggtgca atattgatat cctggtaaat     240

aatgccggct tggcgttggg catggagcct gcgcataaag ccagcgttga agactgggaa     300

acgatgattg ataccaacaa caaaggcctg gtatatatga cgcgcgccgt cttaccgggt     360

atggttgaac gtaatcatgg tcatattatt aacattggct caacggcagg tagctggccg     420

tatgccggtg gtaacgttta cggtgcgacg aaagcgtttg ttcgtcagtt tagcctgaat     480

ctgcgtacgg atctgcatgg tacggcggtg cgcgtcaccg acatcgaacc gggtctggtg     540

ggtggcaccg agttttccaa tgtccgcttt aaaggcgatg acggtaaagc ggaaaaaacc     600

tatcaaaata ccgttgcatt gacgccagaa gatgtcagcg aagccgtctg gtgggtgtca     660

acgctgcctg ctcacgtcaa tatcaatacc ctggaaatga tgccggttac ccaaagctat     720

gccggactga atgtccaccg tcagtaa                                         747
```

<210> SEQ ID NO 58
<211> LENGTH: 248
<212> TYPE: PRT
<213> ORGANISM: Proteobacteria

<400> SEQUENCE: 58

```
Met Ile Val Leu Val Thr Gly Ala Thr Ala Gly Phe Gly Glu Cys Ile
1               5                   10                  15

Thr Arg Arg Phe Ile Gln Gln Gly His Lys Val Ile Ala Thr Gly Arg
            20                  25                  30

Arg Gln Glu Arg Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245
```

<210> SEQ ID NO 59
<211> LENGTH: 987
<212> TYPE: DNA
<213> ORGANISM: Aspergillus pseudoterreus

<400> SEQUENCE: 59

```
ggttgtagca gcgtaaacac atggatagtt aaataatcgg atgtacaccc actgttggaa     60

atgacggggg cctacaacac gagattatct gatccaattt ctgttcgttg gcattctatc    120

attcgcagcg aaaattgtcc tattaaattg accatgacca aacaatctgc ggacagcaac    180

gcaaagtcag gagttacgtc cgaaatatgt cattgggcat ccaacctggc cactgacgac    240

atcccttcgg acgtattaga aagagcaaaa taccttattc tcgacggtat tgcatgtgcc    300

tgggttggtg caagagtgcc ttggtcagag aagtatgttc aggcaacgat gagctttgag    360

ccgccggggg cctgcagggt gattggatat ggacaggtaa attttattca ctctagacgg    420

tccacaaagt atactgacga tccttcgtat agaaactggg gcctgttgca gcagccatga    480
```

```
ccaattccgc tttcatacag gctacggagc ttgacgacta ccacagcgaa gccccccctac    540

actctgcaag cattgtcctt cctgcggtct ttgcagcaag tgaggtctta gccgagcagg    600

gcaaaacaat ttccggtata gatgttattc tagccgccat tgtggggttt gaatctggcc    660

cacggatcgg caaagcaatc tacggatcgg acctcttgaa caacggctgg cattgtggag    720

ctgtgtatgg cgctccagcc ggtgcgctgg ccacaggaaa gctcctcggt ctaactccag    780

actccatgga agatgctctc ggaattgcgt gcacgcaagc ctgtggttta atgtcggcgc    840

aatacggagg catggtaaag cgtgtgcaac acggattcgc agcgcgtaat ggtcttcttg    900

ggggactgtt ggcccatggt gggtacgagg caatgaaagg tgtcctggag agatcttacg    960

gcggtttcct caagatgttc accaagg                                         987
```

```
<210> SEQ ID NO 60
<211> LENGTH: 50
<212> TYPE: DNA
<213> ORGANISM: Artificial Sequence
<220> FEATURE:
<223> OTHER INFORMATION: primer used to isolate A. pseudoterreus 5'-cadA
      gene

<400> SEQUENCE: 60

ccctcgaggt cgacggtatc gatagatatc ggttgtagca gcgtaaacac                 50
```

```
<210> SEQ ID NO 61
<211> LENGTH: 33
<212> TYPE: DNA
<213> ORGANISM: Artificial Sequence
<220> FEATURE:
<223> OTHER INFORMATION: primer used to isolate A. pseudoterreus 5'-cadA
      gene

<400> SEQUENCE: 61

tctttcatag tagccttggt gaacatcttg agg                                   33
```

```
<210> SEQ ID NO 62
<211> LENGTH: 813
<212> TYPE: DNA
<213> ORGANISM: Aspergillus niger

<400> SEQUENCE: 62

ctactatgaa agaccgcgat gggccgatag tagtagttac ttccattaca tcatctcatc     60

cgcccggttc ctcgcctccg cggcagtcta cgggtaggat cgtagcaaaa acccggggga    120

tagacccgtc gtcccgagct ggagttccgt ataacctagg tagaaggtat caattgaacc    180

cgaacaactg gcaaaacatt ctcgagatcg taggagtgag tacccggcgt gatggagggg    240

gagcacgctc attggtccgt acggcagctg ccgagggggga gcaggagatc caaatatcgt    300

gagtctcctg ctttgcccgg tgtatgaaac cggaaaggac tgctggggaa ctggggagcg    360

gcgcaagccg ggaatcccag ctgacaattg acccatcctc atgccgtggc agagcttgag    420

gtagcttttg ccccgtctgt ctccccggtg tgcgcattcg actgggcgcg gcatctgtgc    480

ctcctccagg agcggaggac ccagtagtaa gtaggcctga cctggtcgtt gcgtcagtcc    540

agaggttccc tcccctaccc tttttctact tcccctcccc cgccgctcaa cttttctttc    600

ccttttactt tctctctctc ttcctcttca tccatcctct cttcatcact tccctcttcc    660

cttcatccaa ttcatcttcc aagtgagtct tcctccccat ctgtccctcc atctttccca    720

tcatcatctc ccttcccagc tcctcccctc ctctcgtctc ctcacgaagc ttgactaacc    780
```

attaccccgc cacatagaca catctaaaca atg 813

<210> SEQ ID NO 63
<211> LENGTH: 34
<212> TYPE: DNA
<213> ORGANISM: Artificial Sequence
<220> FEATURE:
<223> OTHER INFORMATION: primer used to isolate an A. niger gpdA promoter

<400> SEQUENCE: 63
atgttcacca aggctactat gaaagaccgc gatg 34

<210> SEQ ID NO 64
<211> LENGTH: 36
<212> TYPE: DNA
<213> ORGANISM: Artificial Sequence
<220> FEATURE:
<223> OTHER INFORMATION: primer used to isolate an A. niger gpdA promoter

<400> SEQUENCE: 64
cgccggtggc gggcattgtt tagatgtgtc tatgtg 36

<210> SEQ ID NO 65
<211> LENGTH: 1617
<212> TYPE: DNA
<213> ORGANISM: Artificial Sequence
<220> FEATURE:
<223> OTHER INFORMATION: panD cDNA of Tribolium castaneum with codon optimization for A. pseudoterreus

<400> SEQUENCE: 65
cccgccaccg gcgaggacca ggacctggtg caggacctga tcgaggaacc cgccaccttc 60
tccgacgccg tcctgtcctc cgacgaggaa ctgttccacc agaagtgccc caagccggct 120
ccgatctaca gccccgtcag caagcccgtc agcttcgagt ccctgccgaa ccgccgcctg 180
cacgaagagt tcctccgctc ctccgtcgac gtcctgctgc aagaggccgt gttcgagggc 240
accaaccgca agaaccgcgt cctgcagtgg cgcgagcccg aagaactgcg ccgcctgatg 300
gacttcggcg tccgcagcgc cccgtccacg catgaggaac tgctcgaggt cctgaagaag 360
gtcgtcacct actccgtcaa gaccggccat ccgtacttcg tcaaccagct gttctccgcc 420
gtcgatccct acggcctggt cgcccagtgg gccaccgacg cgctgaaccc ctccgtctac 480
acctacgagg tcagccccgt gttcgtcctg atggaagagg tcgtcctgcg cgagatgcgc 540
gccatcgtcg gcttcgaagg cggcaaaggc gacggcatct tctgccctgg cggctcgatc 600
gccaacggct acgccatcag ctgcgcccgc taccgcttca tgcccgacat caagaagaag 660
ggcctgcact ccctgccgcg cctggtcctg ttcacctccg aggacgccca ctactcgatc 720
aagaagctgg cctcgttcca aggcatcggc accgacaacg tctacctgat ccgcaccgac 780
gctcgcggtc gcatggacgt cagccacctg gtcgaagaga tcgagcgctc cctccgcgag 840
ggcgctgccc cgttcatggt cagcgccacc gccggcacca ccgtcatcgg cgccttcgat 900
cccatcgaga agatcgccga cgtctgccag aagtacaagc tctggctgca cgtcgacgcc 960
gcctggggcg gaggcgctct ggtgtccgcc aagcaccgcc atctgctgaa gggcatcgag 1020
cgcgccgact ccgtcacctg gaatccccac aagctgctga ccgctccgca gcagtgcagc 1080
accctgctgc tgcgccacga gggcgtcctg gccgaggcgc actccaccaa cgccgcctac 1140
ctgttccaga aggacaagtt ctacgacacc aagtacgaca ccggcgacaa gcacatccag 1200

```
tgcggccgtc gcgccgacgt gctgaagttc tggttcatgt ggaaggccaa gggcacctcc   1260

ggcctcgaga agcacgtgga caaggtgttc gagaacgccc gcttcttcac cgactgcatc   1320

aagaaccgtg agggcttcga gatggtgatc gccgagcctg agtacaccaa catctgtttc   1380

tggtacgtcc ccaagagcct gcgcggacgc aaggacgagg ccgactacaa ggacaagctg   1440

cacaaggtcg cccctcgcat caaagaacgc atgatgaagg aaggctccat gatggtcacc   1500

taccaggcgc agaagggcca tccgaatttc ttccgcatcg tctttcagaa ctccggcctg   1560

gacaaggccg acatggtcca tctggtcgag gaaatcgaac gcctgggctc cgacctc      1617
```

<210> SEQ ID NO 66
<211> LENGTH: 33
<212> TYPE: DNA
<213> ORGANISM: Artificial Sequence
<220> FEATURE:
<223> OTHER INFORMATION: primer used to isolate panD cDNA of Tribolium castaneum with codon optimization for A. pseudoterreus

<400> SEQUENCE: 66

```
catctaaaca atgcccgcca ccggcgagga cca                                  33
```

<210> SEQ ID NO 67
<211> LENGTH: 35
<212> TYPE: DNA
<213> ORGANISM: Artificial Sequence
<220> FEATURE:
<223> OTHER INFORMATION: primer used to isolate panD cDNA of Tribolium castaneum with codon optimization for A. pseudoterreus

<400> SEQUENCE: 67

```
atccaaccca tcagaggtcg gagcccaggc gttcg                                35
```

<210> SEQ ID NO 68
<211> LENGTH: 1040
<212> TYPE: DNA
<213> ORGANISM: Aspergillus niger

<400> SEQUENCE: 68

```
tgatgggttg gatgacgatg acttcatgtg attttgttat ttagaatatt ttatatttcc     60

ttttcttctt ctcaccaccg atccccttaa cactcttgct tcatttgctt cagatttctc    120

ggtttcttct tttttcttct ccccagttat ccactatatc tttgctagac cggcctgcgc    180

cctggcatgc atcataaaat catgtccgtt ggtcatcatc tgttttgtat atccgtcata    240

taaagtattc ttttattccc tccccccctcg gtcgtctttc gctgtcccgc ttcctacctc    300

cggtttatag agcatggttc atctcttccg tacatttccg ttggtactag catttatgtc    360

ttcagctagt atagaagctg ccgcagttgt tcgcttacta cctgcctaag tccttaactt    420

tttaaagtgt ttaacctata cgtagtgtta aacgagtact gggaggtggt gaggtagaaa    480

atgttctgca cgggcagtgg gtatttggta gtgtgtaagg cggttattta tcaggctgac    540

gctaaagact tctatgggag cagtatggga tcgcggctca tagaagtaca caaaatctaa    600

gagtcgtttg ataattaatt gattcccggc agggtcttct tgggattgag agaactggtt    660

actttgattt gagatattgt aaagcttaag gctcttaaca cgtacgagcg aaacagcagg    720

ggggaaatcg ggaaaagggg cgtggggtga ataaaaaagt tgaaataaga cactgtatct    780

tgctgggggt gaataaagag agaataaaag agaggtaaat tccactcagc ccctttttctt    840

cgctctccaa acatcaaact ccgccggccg acccacagga tcccgaacaa gtggaagata    900

tgtgccggtc cagacccttc gcacagctaa aagcagacct tcataagcgt ttccgggtag    960
```

tattcgcaca cctgaactgg cacgtcgggg acacaactgt ttttgataca caagaacaca 1020
caccacccat ctaggactca 1040

<210> SEQ ID NO 69
<211> LENGTH: 33
<212> TYPE: DNA
<213> ORGANISM: Artificial Sequence
<220> FEATURE:
<223> OTHER INFORMATION: primer used to isolate bidirectional terminator from A. niger elf3/multifunctional chaperone

<400> SEQUENCE: 69
gggctccgac ctctgatggg ttggatgacg atg 33

<210> SEQ ID NO 70
<211> LENGTH: 33
<212> TYPE: DNA
<213> ORGANISM: Artificial Sequence
<220> FEATURE:
<223> OTHER INFORMATION: primer used to isolate bidirectional terminator from A. niger elf3/multifunctional chaperone

<400> SEQUENCE: 70
tctggcccag ctctgagtcc tagatgggtg gtg 33

<210> SEQ ID NO 71
<211> LENGTH: 1350
<212> TYPE: DNA
<213> ORGANISM: Artificial Sequence
<220> FEATURE:
<223> OTHER INFORMATION: codon optimized synthetic cDNA of beta-alanine-pyruvate aminotransferase (BAPAT) of Bacillus cereus

<400> SEQUENCE: 71
gagctgggcc agacattcct tcatagtctt gacgatgaag gtgaagtcct cttcggtgat 60
ggacagcgga ggggcgagct gcaggatgtt gttgtagccg gccacggtgt cgccgttctt 120
gccgatgatc agacccttct ctttgcaggc gttgatgacc ttgttcatct tttcgatgga 180
ggcgggctct ttggtctgct tatcctcgac gagttcgata cccagcagga ggcccttgcc 240
gcggacgtcc ccgacgttgg ggtgctcttt gacgtcctcc aactcgtaca gcaggcgctc 300
gcccagttct ttggaccgct cgatgagctt ctcgttttcc atgatctcga ggttcttcag 360
ggccagcgcg caggcggcag ggttgccgcc gaaggtgttg acatggcgga agcggtcgta 420
gtcgtcggag ccgacgaagg cctcgtagac ctcgcggcgg accgcggtgg cagacagcgg 480
caggtaggcc gaggtgatac ccttggccat ggtgataatg tcgggcttga cgccgtagtt 540
catgaagccg aagggcttgc cggtgcgacc gaagccgcag atgacctcgt cgcagatcag 600
cagggcgccg tgcttttcgc agatctcttt gaccttttcc atgtagccgt ccggcggcat 660
caggatgcca ccaccggtga tgatgggttc catgatgacg ccggcgacgg tctgggacag 720
ctcccaggtc atgacgcggt cgatttcttc ggcggaggcc agggtgtgca cgtcctcggg 780
gttgcgatag gtgtccggag gggccacgtg caggaagccc tgaccgaggg gctcgtactt 840
gtacttgcgc tgggcctgac cggtcgcggc cagggcaccc atggagttgc cgtggtaggc 900
gcggtagcga gagatgaact tgtagcggcc gtggtcaccc ttctgctggt ggtactggcg 960
ggcgatcttg aaggcggttt cgttggcctc cgagccggag ttggagaaga agatgacgta 1020
ctcgtcgtcc agccactcgt tcagcttctc ggccagcttg atggcgggga cgtgcgactg 1080
cgtcagcggg aagtacggca tctcttccag ctgctcgaag gcagcgcgag ccagctcttt 1140

```
gcggccgtag ccgacgttga cgcaccacag gccggacatg ccgtccaggt agcggttgcc   1200

gtcgatgtcg gtgacccacg cgccttcggc cttggtgatg atcaggttgg tcggactcgg   1260

agcggcaccg cgcatggcgt gccacaggta cttctcgtcg gttttcttca ggctctgggt   1320

ctgctcggtg acctggacga tcatcagttc                                    1350


<210> SEQ ID NO 72
<211> LENGTH: 35
<212> TYPE: DNA
<213> ORGANISM: Artificial Sequence
<220> FEATURE:
<223> OTHER INFORMATION: primer used to isolate codon optimized
      synthetic cDNA of beta-alanine-pyruvate aminotransferase (BAPAT)
      of Bacillus cereus

<400> SEQUENCE: 72

catctaggac tcagagctgg gccagacatt ccttc                                35


<210> SEQ ID NO 73
<211> LENGTH: 36
<212> TYPE: DNA
<213> ORGANISM: Artificial Sequence
<220> FEATURE:
<223> OTHER INFORMATION: primer used to isolate codon optimized
      synthetic cdna of beta-alanine-pyruvate aminotransferase (bapat)
      of bacillus cereus

<400> SEQUENCE: 73

gtccatcaac atggaactga tgatcgtcca ggtcac                               36


<210> SEQ ID NO 74
<211> LENGTH: 704
<212> TYPE: DNA
<213> ORGANISM: Aspergillus niger

<400> SEQUENCE: 74

catgttgatg gactggaggg ggatgagtta tggatcagtg aaactgggag aaaacaaaga     60

tggcaaaggg agaacatggc ccagatatag gaaaaaacgg aggaggcaaa aatgtaagcg    120

ctccggactt gctgtttcgg tgtgcactag cagcagcggg ggggaaggtg gtgagtgttc    180

accgaggacc caaaaagaat gagcggatgg cggatgagtg acggagaagg gaaggacggg    240

gggggaatta gaggtggaga ggtccgatcc atcaaataga ccaggctcgg cacagccaag    300

tttcccaaat gatcaactaa tcaatgggac ttggtgctaa atccggagat gccagatcat    360

tgatagacag acaggatgga gtgatggcat atagacagga ggatggatgg atggatagat    420

ggaggggtca agcacaacat ggtgggatga tggcggggtc atgactagca gctaagagga    480

agaagaggag gatgaaatgg acagagaaag atgggagggg tgataaaatg agtatatggg    540

acaagtcata cttacaggac cttgaagatg gtggttgtac tatctaagaa aggctttttt    600

tgagagtact cttaacacaa gaggaggagg gaggaggggg aagtagtaga taaataataa    660

acacgaccac agacttgcta caggctactt cttgtaagct cgag                     704


<210> SEQ ID NO 75
<211> LENGTH: 33
<212> TYPE: DNA
<213> ORGANISM: Artificial Sequence
<220> FEATURE:
<223> OTHER INFORMATION: primer used to isolate an A. niger eno1
      promoter

<400> SEQUENCE: 75
```

cgatcatcag ttccatgttg atggactgga ggg 33

<210> SEQ ID NO 76
<211> LENGTH: 51
<212> TYPE: DNA
<213> ORGANISM: Artificial Sequence
<220> FEATURE:
<223> OTHER INFORMATION: primer used to isolate an A. niger eno1 promoter

<400> SEQUENCE: 76
gaactagtgg atcccccggg ctgcgttaac tcgagcttac aagaagtagc c 51

<210> SEQ ID NO 77
<211> LENGTH: 885
<212> TYPE: DNA
<213> ORGANISM: Aspergillus nidulans

<400> SEQUENCE: 77
tctgtacagt gaccggtgac tctttctggc atgcggagag acggacggac gcagagagaa 60
gggctgagta ataagccact ggccagacag ctctggcggc tctgaggtgc agtggatgat 120
tattaatccg ggaccggccg cccctccgcc ccgaagtgga aaggctggtg tgcccctcgt 180
tgaccaagaa tctattgcat catcggagaa tatggagctt catcgaatca ccggcagtaa 240
gcgaaggaga atgtgaagcc aggggtgtat agccgtcggc gaaatagcat gccattaacc 300
taggtacaga agtccaattg cttccgatct ggtaaaagat tcacgagata gtaccttctc 360
cgaagtaggt agagcgagta cccggcgcgt aagctcccta attggcccat ccggcatctg 420
tagggcgtcc aaatatcgtg cctctcctgc tttgcccggt gtatgaaacc ggaaaggccg 480
ctcaggagct ggccagcggc gcagaccggg aacacaagct ggcagtcgac ccatccggtg 540
ctctgcactc gacctgctga ggtccctcag tccctggtag gcagctttgc cccgtctgtc 600
cgcccggtgt gtcggcgggg ttgacaaggt cgttgcgtca gtccaacatt tgttgccata 660
ttttcctgct ctccccacca gctgctcttt tcttttctct ttcttttccc atcttcagta 720
tattcatctt cccatccaag aacctttatt tcccctaagt aagtactttg ctacatccat 780
actccatcct tcccatccct tattcctttg aacctttcag ttcgagcttt cccacttcat 840
cgcagcttga ctaacagcta ccccgcttga gcagacatca ccatg 885

<210> SEQ ID NO 78
<211> LENGTH: 50
<212> TYPE: DNA
<213> ORGANISM: Artificial Sequence
<220> FEATURE:
<223> OTHER INFORMATION: primer used to isolate an A. nidulans gpdA promoter

<400> SEQUENCE: 78
ccctcgaggt cgacggtatc gatagttaac tctgtacagt gaccggtgac 50

<210> SEQ ID NO 79
<211> LENGTH: 33
<212> TYPE: DNA
<213> ORGANISM: Artificial Sequence
<220> FEATURE:
<223> OTHER INFORMATION: primer used to isolate an A. nidulans gpdA promoter

<400> SEQUENCE: 79
tgaccagcac gatcatggtg atgtctgctc aag 33

<210> SEQ ID NO 80
<211> LENGTH: 741
<212> TYPE: DNA
<213> ORGANISM: Artificial Sequence
<220> FEATURE:
<223> OTHER INFORMATION: codon optimized synthetic cDNA of E. coli HPDH

<400> SEQUENCE: 80
atcgtgctgg tcacgggcgc gaccgccggt ttcggcgagt gcatcacccg ccgcttcatc 60
cagcagggcc acaaggtgat cgctaccgga cgccgccaag agcgcctcca agagctgaag 120
gatgagctgg gcgacaacct gtacattgcc cagctggacg tgcgcaaccg ggctgccatc 180
gaagaaatgc tcgcctcgct gcccgccgag tggtgcaaca tcgacatcct ggtcaacaac 240
gccggtctgg ccctcggcat ggaaccggcg cacaaggcca gcgtcgagga ctgggaaacc 300
atgatcgaca ccaacaacaa gggactcgtc tacatgaccc gcgctgtgct gcccggcatg 360
gtcgagcgca accacggcca catcatcaac atcggctcca ccgctggcag ctggccctac 420
gctggcggca acgtctatgg cgcgaccaag gcgttcgtcc gccagttctc cctgaacctg 480
cgcaccgacc tgcacggcac cgccgtccgc gtgaccgaca ttgagcccgg tctggtcggc 540
ggcaccgagt tcagcaacgt ccgcttcaag ggcgacgacg gcaaggccga gaaaacctac 600
cagaacaccg tcgctctgac ccctgaggat gtcagcgagg ccgtctggtg ggtcagcact 660
ctgcccgcgc acgtcaacat caacaccctc gagatgatgc ccgtcacgca gtcctacgcc 720
ggcctgaacg tccaccgcca a 741

<210> SEQ ID NO 81
<211> LENGTH: 33
<212> TYPE: DNA
<213> ORGANISM: Artificial Sequence
<220> FEATURE:
<223> OTHER INFORMATION: primer used to isolate a codon optimized synthetic cDNA of E. coli HPDH

<400> SEQUENCE: 81
agacatcacc atgatcgtgc tggtcacggg cgc 33

<210> SEQ ID NO 82
<211> LENGTH: 33
<212> TYPE: DNA
<213> ORGANISM: Artificial Sequence
<220> FEATURE:
<223> OTHER INFORMATION: primer used to isolate a codon optimized synthetic cDNA of E. coli HPDH

<400> SEQUENCE: 82
gccatcggtc ctattggcgg tggacgttca ggc 33

<210> SEQ ID NO 83
<211> LENGTH: 473
<212> TYPE: DNA
<213> ORGANISM: Aspergillus nidulans

<400> SEQUENCE: 83
taggaccgat ggctgtgtag aagtactcgc cgatagtgga aaccgacgcc ccagcactcg 60
tccgagggca aaggaataga gtagatgccg accgcgggat ccacttaacg ttactgaaat 120
catcaaacag cttgacgaat ctggatataa gatcgttggt gtcgatgtca gctccggagt 180
tgagacaaat ggtgttcagg atctcgataa gatacgttca tttgtccaag cagcaaagag 240

```
tgccttctag tgatttaata gctccatgtc aacaagaata aaacgcgttt tcgggtttac    300

ctcttccaga tacagctcat ctgcaatgca ttaatgcatt gactgcaacc tagtaacgcc    360

ttcaggctcc ggcgaagaga agaatagctt agcagagcta ttttcatttt cgggagacga    420

gatcaagcag atcaacggtc gtcaagagac ctacgagact gaggaatccg ctc           473


<210> SEQ ID NO 84
<211> LENGTH: 33
<212> TYPE: DNA
<213> ORGANISM: Artificial Sequence
<220> FEATURE:
<223> OTHER INFORMATION: primer used to isolate the trpC terminator of
      A. nidulans

<400> SEQUENCE: 84

cgtccaccgc caataggacc gatggctgtg tag                                  33


<210> SEQ ID NO 85
<211> LENGTH: 45
<212> TYPE: DNA
<213> ORGANISM: Artificial Sequence
<220> FEATURE:
<223> OTHER INFORMATION: primer used to isolate the trpC terminator of
      A. nidulans

<400> SEQUENCE: 85

gaactagtgg atcccccggg ctgcagagcg gattcctcag tctcg                     45


<210> SEQ ID NO 86
<211> LENGTH: 510
<212> TYPE: DNA
<213> ORGANISM: Aspergillus nidulans

<400> SEQUENCE: 86

ccctcgaggt cgacggtatc gatataggac cgatggctgt gtagaagtac tcgccgatag     60

tggaaaccga cgccccagca ctcgtccgag ggcaaaggaa tagagtagat gccgaccgcg    120

ggatccactt aacgttactg aaatcatcaa acagcttgac gaatctggat ataagatcgt    180

tggtgtcgat gtcagctccg gagttgagac aaatggtgtt caggatctcg ataagatacg    240

ttcatttgtc caagcagcaa agagtgcctt ctagtgattt aatagctcca tgtcaacaag    300

aataaaacgc gttttcgggt ttacctcttc cagatacagc tcatctgcaa tgcattaatg    360

cattgactgc aacctagtaa cgccttcagg ctccggcgaa gagaagaata gcttagcaga    420

gctattttca ttttcgggag acgagatcaa gcagatcaac ggtcgtcaag agacctacga    480

gactgaggaa tccgctctct gacagacggg                                     510


<210> SEQ ID NO 87
<211> LENGTH: 44
<212> TYPE: DNA
<213> ORGANISM: Artificial Sequence
<220> FEATURE:
<223> OTHER INFORMATION: primer used to isolate a trpC terminator of A.
      nidulans

<400> SEQUENCE: 87

ccctcgaggt cgacggtatc gatataggac cgatggctgt gtag                      44


<210> SEQ ID NO 88
<211> LENGTH: 33
<212> TYPE: DNA
<213> ORGANISM: Artificial Sequence
<220> FEATURE:
```

<223> OTHER INFORMATION: primer used to isolate a trpC terminator of A. nidulans

<400> SEQUENCE: 88
cccgtctgtc agagagcgga ttcctcagtc tcg 33

<210> SEQ ID NO 89
<211> LENGTH: 2005
<212> TYPE: DNA
<213> ORGANISM: Aspergillus oryzae

<400> SEQUENCE: 89
tctgacagac gggcaattga ttacgggatc ccattggtaa cgaaatgtaa aagctaggag 60
atcgtccgcc gatgtcagga tgatttcact tgtttcttgt ccggctcacc ggtcaaagct 120
aaagaggagc aaaaggaacg gatagaatcg ggtgccgctg atctatacgg tatagtgccc 180
ttatcacgtt gactcaaccc atgctattta actcaacccc tccttctgaa ccccaccatc 240
ttcttccttt tcctctcatc ccacacaatt ctctatctca gatttgaatt ccaaaagtcc 300
tcggacgaaa ctgaacaagt cttcctccct tcgataaacc tttggtgatt ggaataactg 360
accatcttct atagttccca aaccaaccga caatgtaaat acactcctcg attagccctc 420
tagagggcat acgatggaag tcatggaata cttttggctg gactctcaca atgatcaagg 480
tatcttaggt aacgtctttg gcgtgggccg gtgttcgttc ccagtcatcg atgcattcac 540
atgccctccc taagctgggc cctagactct aggatcctag tctagaagga catggcatcg 600
atggactggg ttcgttctga gattatacgg ctaaaacttg atctggataa taccagcgaa 660
aagggtcatg ccttctctcg ttcttcctgt tgatggaatg gctaacagat gatagtcatt 720
gcaacttgaa acatgtctcc tccagctgcc atctacgaac ccactgtggc cgctaccggc 780
ctcaagggta aggtcgtggt ttctgagacc gtccccgttg agggagcttc tcagaccaag 840
ctgttggacc atttcggtgg caagtgggac gagttcaagt tcgcccctat ccgcgaaagc 900
caggtctctc gtgccatgac cagacgttac tttgaggacc tggacaagta cgctgaaagt 960
gacgttgtca ttgttggtgc tggttcctgc ggtctgagca ctgcgtacgt cttggccaag 1020
gctcgtccgg acctgaagat tgctatcgtc gaggccagcg tctctcctgg tcagtagtcc 1080
atgatggatt gccttgcact cagctttccg gaactaacgt gcaataggtg gcggtgcctg 1140
gttgggtggc caactctttt ctgctatggt catgcgccgt cccgcggaag tcttcctgaa 1200
cgagctgggt gttccttacg aagaggacgc aaaccccaac tacgttgtcg tcaagcacgc 1260
ctccctgttt acctcgacac tcatgtcgaa ggttctctcc ttccccaatg tcaagctctt 1320
caatgctacc gctgttgagg acttgatcac ccgtccgacc gagaacggca acccccagat 1380
tgctggtgtt gtcgtcaact ggacgctggt cacccttcac cacgatgatc actcctgcat 1440
ggaccccaac actatcaacg ctcctgtcat catcagtacc actggtcacg atgggccatt 1500
cggcgccttc tgtgcgaagc gcttggtgtc catgggcagc gtcgacaagc taggtggcat 1560
gcgtggtctc gacatgaact cggccgagga tgccatcgtc aagaacaccc gcgaggttac 1620
taagggcttg ataatcggcg gtatggagct gtctgaaatt gatggcttta accgcatggg 1680
ccctaccttc ggtgccatgg ttctcagtgg tgtcaaggct gccgaggagg cattgaaggt 1740
gttcgacgag cgtcagcgcg agtgtgctga gtaaatgact cactacccga atgggttcag 1800
tgcatgaacc ggatttgtct tacggtcttt gacgataggg gaatgatgat tatgtgatag 1860
ttctgagatt tgaatgaact cgttagctcg taatccacat gcatatgtaa atggctgtgt 1920

```
cccgtatgta acggtggggc attctagaat aattatgtgt aacaagaaag acagtataat   1980

acaaacaaag atgcaagagc ggctc                                         2005
```

<210> SEQ ID NO 90
<211> LENGTH: 37
<212> TYPE: DNA
<213> ORGANISM: Artificial Sequence
<220> FEATURE:
<223> OTHER INFORMATION: primer used to isolate the A. oryzae ptrA selection marker gene

<400> SEQUENCE: 90

```
gaggaatccg ctctctgaca gacgggcaat tgattac                              37
```

<210> SEQ ID NO 91
<211> LENGTH: 33
<212> TYPE: DNA
<213> ORGANISM: Artificial Sequence
<220> FEATURE:
<223> OTHER INFORMATION: primer used to isolate the A. oryzae ptrA selection marker gene

<400> SEQUENCE: 91

```
gaatgttgct gaggagccgc tcttgcatct ttg                                  33
```

<210> SEQ ID NO 92
<211> LENGTH: 908
<212> TYPE: DNA
<213> ORGANISM: Aspergillus pseudoterreus

<400> SEQUENCE: 92

```
ctcagcaaca ttcgccatgt tcatgtacag ctttcaacgg cctcgaacag tcactgtgga     60

tggataccag aggagagacc catcagttca atcgcagggc agatgagtgt cgcatacatt    120

ctcgccgtcc agctggtcga ccagcaatgt cttttgtccc agttttctga gtttgatgac    180

aacctggaga ggccagaagt ttgggatctg gccaggaagg ttacttcatc tcaaagcgaa    240

gagtttgatc aagacggcaa ctgtctcagt gcgggtcgcg tgaggattga gttcaacgat    300

ggttcttcta ttacggaaag tgtcgagaag cctcttggtg tcaaagagcc catgccaaac    360

gaacggattc tccacaaata ccgaaccctt gctggtagcg tgacggacga atcccgggtg    420

aaagagattg aggatcttgt cctcggcctg gacaggctca ccgacattag cccattgctg    480

gagctgctga attgccccgt gaaatcgcca ctggtataaa tgggaagcga tatggaaaca    540

tttcatgtca cgggcacaaa ttctaggtca tatcgtacct ggatggtgaa accaccagcg    600

gtttagcaga tagaagatag actccttctg ctctgcgttg cgtcttgaat ttagttcgtt    660

cactggctta agaacttaga atgcaataca gtctctctta tttcttatta aaatcacgta    720

ttcccacatt cggcgactgg aggatacgaa agcagtgttg gtggtgctcc ccgtaatgga    780

tatgattttg ctgactggac tattctatga ccattccctc caacggagat cctttctcga    840

cactttagat gttgacgctg tctggaggaa ctacttttgc gctgcaaaga ctatgagcag    900

tggagctg                                                             908
```

<210> SEQ ID NO 93
<211> LENGTH: 35
<212> TYPE: DNA
<213> ORGANISM: Artificial Sequence
<220> FEATURE:
<223> OTHER INFORMATION: primer used to isolate an A. pseudoterreus 3'-cad1 gene fragment

<400> SEQUENCE: 93
gcaagagcgg ctcctcagca acattcgcca tgttc 35

<210> SEQ ID NO 94
<211> LENGTH: 49
<212> TYPE: DNA
<213> ORGANISM: Artificial Sequence
<220> FEATURE:
<223> OTHER INFORMATION: primer used to isolate an A. pseudoterreus 3'-
cad1 gene fragment

<400> SEQUENCE: 94
gaactagtgg atcccccggg ctgcacagct ccactgctca tagtctttg 49

<210> SEQ ID NO 95
<211> LENGTH: 2099
<212> TYPE: DNA
<213> ORGANISM: Artificial Sequence
<220> FEATURE:
<223> OTHER INFORMATION: combination of SEQ ID NOS: 77, 80, and 83

<400> SEQUENCE: 95
tctgtacagt gaccggtgac tctttctggc atgcggagag acggacggac gcagagagaa 60
gggctgagta ataagccact ggccagacag ctctggcggc tctgaggtgc agtggatgat 120
tattaatccg ggaccggccg cccctccgcc ccgaagtgga aaggctggtg tgcccctcgt 180
tgaccaagaa tctattgcat catcggagaa tatggagctt catcgaatca ccggcagtaa 240
gcgaaggaga atgtgaagcc aggggtgtat agccgtcggc gaaatagcat gccattaacc 300
taggtacaga agtccaattg cttccgatct ggtaaaagat tcacgagata gtaccttctc 360
cgaagtaggt agagcgagta cccggcgcgt aagctcccta attggcccat ccggcatctg 420
tagggcgtcc aaatatcgtg cctctcctgc tttgcccggt gtatgaaacc ggaaaggccg 480
ctcaggagct ggccagcggc gcagaccggg aacacaagct ggcagtcgac ccatccggtg 540
ctctgcactc gacctgctga ggtccctcag tccctggtag gcagctttgc cccgtctgtc 600
cgcccggtgt gtcggcgggg ttgacaaggt cgttgcgtca gtccaacatt tgttgccata 660
ttttcctgct ctccccacca gctgctcttt tcttttctct ttcttttccc atcttcagta 720
tattcatctt cccatccaag aacctttatt tcccctaagt aagtactttg ctacatccat 780
actccatcct tcccatccct tattcctttg aacctttcag ttcgagcttt cccacttcat 840
cgcagcttga ctaacagcta ccccgcttga gcagacatca ccatgatcgt gctggtcacg 900
ggcgcgaccg ccggtttcgg cgagtgcatc acccgccgct tcatccagca gggccacaag 960
gtgatcgcta ccggacgccg ccaagagcgc ctccaagagc tgaaggatga gctgggcgac 1020
aacctgtaca ttgcccagct ggacgtgcgc aaccgggctg ccatcgaaga aatgctcgcc 1080
tcgctgcccg ccgagtggtg caacatcgac atcctggtca acaacgccgg tctggccctc 1140
ggcatggaac cggcgcacaa ggccagcgtc gaggactggg aaaccatgat cgacaccaac 1200
aacaagggac tcgtctacat gacccgcgct gtgctgcccg gcatggtcga gcgcaaccac 1260
ggccacatca tcaacatcgg ctccaccgct ggcagctggc cctacgctgg cggcaacgtc 1320
tatggcgcga ccaaggcgtt cgtccgccag ttctccctga acctgcgcac cgacctgcac 1380
ggcaccgccg tccgcgtgac cgacattgag cccggtctgg tcggcggcac cgagttcagc 1440
aacgtccgct tcaagggcga cgacggcaag gccgagaaaa cctaccagaa caccgtcgct 1500
ctgacccctg aggatgtcag cgaggccgtc tggtgggtca gcactctgcc cgcgcacgtc 1560
aacatcaaca ccctcgagat gatgcccgtc acgcagtcct acgccggcct gaacgtccac 1620
cgccaatagg accgatggct gtgtagaagt actcgccgat agtggaaacc gacgccccag 1680
cactcgtccg agggcaaagg aatagagtag atgccgaccg cgggatccac ttaacgttac 1740
tgaaatcatc aaacagcttg acgaatctgg atataagatc gttggtgtcg atgtcagctc 1800
cggagttgag acaaatggtg ttcaggatct cgataagata cgttcatttg tccaagcagc 1860
aaagagtgcc ttctagtgat ttaatagctc catgtcaaca agaataaaac gcgttttcgg 1920
gtttacctct tccagataca gctcatctgc aatgcattaa tgcattgact gcaacctagt 1980
aacgccttca ggctccggcg aagagaagaa tagcttagca gagctatttt cattttcggg 2040
agacgagatc aagcagatca acggtcgtca agagacctac gagactgagg aatccgctc 2099

<210> SEQ ID NO 96
<211> LENGTH: 47
<212> TYPE: DNA
<213> ORGANISM: Artificial Sequence
<220> FEATURE:
<223> OTHER INFORMATION: primer to isolate Fragments 7 to 9

<400> SEQUENCE: 96
acaggctact tcttgtaagc tcgagtttct gtacagtgac cggtgac 47

<210> SEQ ID NO 97
<211> LENGTH: 2913
<212> TYPE: DNA
<213> ORGANISM: Artificial Sequence
<220> FEATURE:
<223> OTHER INFORMATION: combination of SEQ ID NOS: 89 and 92

<400> SEQUENCE: 97
tctgacagac gggcaattga ttacgggatc ccattggtaa cgaaatgtaa aagctaggag 60
atcgtccgcc gatgtcagga tgatttcact tgtttcttgt ccggctcacc ggtcaaagct 120
aaagaggagc aaaaggaacg gatagaatcg ggtgccgctg atctatacgg tatagtgccc 180
ttatcacgtt gactcaaccc atgctattta actcaacccc tccttctgaa ccccaccatc 240
ttcttccttt tcctctcatc ccacacaatt ctctatctca gatttgaatt ccaaaagtcc 300
tcggacgaaa ctgaacaagt cttcctccct tcgataaacc tttggtgatt ggaataactg 360
accatcttct atagttccca aaccaaccga caatgtaaat acactcctcg attagccctc 420
tagagggcat acgatggaag tcatggaata cttttggctg gactctcaca atgatcaagg 480
tatcttaggt aacgtctttg gcgtgggccg gtgttcgttc ccagtcatcg atgcattcac 540
atgccctccc taagctgggc cctagactct aggatcctag tctagaagga catggcatcg 600
atggactggg ttcgttctga gattatacgg ctaaaacttg atctggataa taccagcgaa 660
aagggtcatg ccttctctcg ttcttcctgt tgatggaatg gctaacagat gatagtcatt 720
gcaacttgaa acatgtctcc tccagctgcc atctacgaac ccactgtggc cgctaccggc 780
ctcaagggta aggtcgtggt ttctgagacc gtccccgttg agggagcttc tcagaccaag 840
ctgttggacc atttcggtgg caagtgggac gagttcaagt tcgcccctat ccgcgaaagc 900
caggtctctc gtgccatgac cagacgttac tttgaggacc tggacaagta cgctgaaagt 960
gacgttgtca ttgttggtgc tggttcctgc ggtctgagca ctgcgtacgt cttggccaag 1020
gctcgtccgg acctgaagat tgctatcgtc gaggccagcg tctctcctgg tcagtagtcc 1080
atgatggatt gccttgcact cagctttccg gaactaacgt gcaataggtg gcggtgcctg 1140
gttgggtggc caactctttt ctgctatggt catgcgccgt cccgcggaag tcttcctgaa 1200

```
cgagctgggt gttccttacg aagaggacgc aaaccccaac tacgttgtcg tcaagcacgc   1260

ctccctgttt acctcgacac tcatgtcgaa ggttctctcc ttccccaatg tcaagctctt   1320

caatgctacc gctgttgagg acttgatcac ccgtccgacc gagaacggca acccccagat   1380

tgctggtgtt gtcgtcaact ggacgctggt caccottcac cacgatgatc actcctgcat   1440

ggaccccaac actatcaacg ctcctgtcat catcagtacc actggtcacg atgggccatt   1500

cggcgccttc tgtgcgaagc gcttggtgtc catgggcagc gtcgacaagc taggtggcat   1560

gcgtggtctc gacatgaact cggccgagga tgccatcgtc aagaacaccc gcgaggttac   1620

taagggcttg ataatcggcg gtatggagct gtctgaaatt gatggcttta accgcatggg   1680

ccctaccttc ggtgccatgg ttctcagtgg tgtcaaggct gccgaggagg cattgaaggt   1740

gttcgacgag cgtcagcgcg agtgtgctga gtaaatgact cactacccga atgggttcag   1800

tgcatgaacc ggatttgtct tacggtcttt gacgataggg gaatgatgat tatgtgatag   1860

ttctgagatt tgaatgaact cgttagctcg taatccacat gcatatgtaa atggctgtgt   1920

cccgtatgta acggtggggc attctagaat aattatgtgt aacaagaaag acagtataat   1980

acaaacaaag atgcaagagc ggctcctcag caacattcgc catgttcatg tacagctttc   2040

aacggcctcg aacagtcact gtggatggat accagaggag agacccatca gttcaatcgc   2100

agggcagatg agtgtcgcat acattctcgc cgtccagctg gtcgaccagc aatgtctttt   2160

gtcccagttt tctgagtttg atgacaacct ggagaggcca gaagtttggg atctggccag   2220

gaaggttact tcatctcaaa gcgaagagtt tgatcaagac ggcaactgtc tcagtgcggg   2280

tcgcgtgagg attgagttca acgatggttc ttctattacg gaaagtgtcg agaagcctct   2340

tggtgtcaaa gagcccatgc caaacgaacg gattctccac aaataccgaa cccttgctgg   2400

tagcgtgacg gacgaatccc gggtgaaaga gattgaggat cttgtcctcg gcctggacag   2460

gctcaccgac attagcccat tgctggagct gctgaattgc cccgtgaaat cgccactggt   2520

ataaatggga agcgatatgg aaacatttca tgtcacgggc acaaattcta ggtcatatcg   2580

tacctggatg gtgaaaccac cagcggttta gcagatagaa gatagactcc ttctgctctg   2640

cgttgcgtct tgaatttagt tcgttcactg gcttaagaac ttagaatgca atacagtctc   2700

tcttatttct tattaaaatc acgtattccc acattcggcg actggaggat acgaaagcag   2760

tgttggtggt gctccccgta atggatatga ttttgctgac tggactattc tatgaccatt   2820

ccctccaacg gagatccttt ctcgacactt tagatgttga cgctgtctgg aggaactact   2880

tttgcgctgc aaagactatg agcagtggag ctg                                2913
```

<210> SEQ ID NO 98
<211> LENGTH: 49
<212> TYPE: DNA
<213> ORGANISM: Artificial Sequence
<220> FEATURE:
<223> OTHER INFORMATION: primer used to isolate Fragments 11-12

<400> SEQUENCE: 98

```
actaaaggga acaaaagctg gagctcagct ccactgctca tagtctttg                 49
```